United States Patent [19]
Voytas et al.

[11] Patent Number: 5,976,795
[45] Date of Patent: Nov. 2, 1999

[54] RETROTRANSPOSON AND METHODS

[75] Inventors: Daniel F. Voytas; Sige Zou, both of Ames, Iowa

[73] Assignee: Iowa State University Research Foundation, Inc., Ames, Iowa

[21] Appl. No.: 08/771,602

[22] Filed: Dec. 20, 1996

Related U.S. Application Data

[60] Provisional application No. 60/010,869, Jan. 31, 1996.

[51] Int. Cl.$^6$ .............................. C12Q 1/68; C12N 15/87; C12N 1/16; C07H 21/04
[52] U.S. Cl. ......................... 435/6; 435/254.11; 435/325; 435/462; 536/23.1; 536/23.2
[58] Field of Search .............................. 435/6, 69.1, 91.1, 435/254.11, 325, 462; 536/23.1, 23.2

[56] References Cited

PUBLICATIONS

Marshall. Gene therapy's growing pains. Science 269:1050–1055, Aug. 25, 1995.
Verma et al. Gene therapy—promises, problems and prospects. Nature. vol. 389:239–242, Sep. 18, 1997.
Weatherall, D. J. Scope and limitations of gene therapy. British Medical Bull. vol. 51(1):1–11, Jan. 1995.
Orkin et al. Report and recomendations or the panel to assess the NIH investment in research on gene therapy, Dec. 7, 1995.
Atwood et al., The Retrotransposon Tf1 Assembles Virus–Like Particles That contain excess Gag Relative to Integrase because of a Regulated Degradation Process, *Mol. Cell. Biol.* (1966) 16:338–346.
Bell et al., Yeast Origin Recognition Complex Functions in Transcription Silencing and DNA Replication, *Science* (1993) 262:1844–1849.
Biessmann, et al., Addition of Telomere–Associated HeT DNA Sequences "Heals" Broken Chromosome Ends in Drosophila, *Cell* (1990) 61:663–673.
Boeke et al., A General Method for the Chromosomal Amplification of Genes in Yeast, *Science* (1988) 239:280–282.
Boeke et al., Yeast Transposable Elements, *The Molecular and Cellular Biology of the Yeast Saccharomyces* (1991) Cold Spring Harbor Laboratory Press, Cold Spring Harbor, New York, pp. 193–261.
Brand et al., Characterization of a "Silencer" in Yeast: A DNA Sequence with Propeprties Opposite to Those of a Transcriptional Enhancer, *Cell* (1985) 41:41–48.
Brown et al., The Human XIST Gene: Analysis of a 17 kb Inactive X–Specific RNA That Contains Conserved Repeats and Is Highly Localized within the Nucleus, *Cell* (1992) 71:527–542.
Curcio et al., Single–step selection for Ty1 element retrotransposition, *Proc. Natl. Acad. Sci. USA* (1991) 88:936–940.
Diffley et al., Purification of a yeast protein that binds to origins of DNA replication and a transcriptional silencer, *Proc. Natl. Acad. Sci. USA* (1988) 85:2120–2124.
Dujon et al., Complete DNA sequence of yeast chromosome XI, *Nature* (1994) 369:371–378.
Ji et al., Hotspots for Unselected Ty1 Transposition Events on Yeast Chromosome III are near tRNA Genes and LTR Sequences, *Cell* (1993) 73:1007–1018.
Karpen et al., Analysis of Subtelomeric heterochromatin in the Drosophila Minichromosome Dp1187 by Single P Element Insertional Mutagenesis, *Genetics* (1992) 132:737–753.
Keeney etr al., Multiple Molecular Determinants for Retrotransposition in a Primer tRNA, *Molecular and Cellular Biology* (1995) 15:217–226.
Kikuchi et al., Unusual priming mechanism of RNA–directed DNA Synthesis in copia retrovirus–like particles of Drosophila, *Nature* (1995) 323:824–826.
Laurenson et al., Silencers, Silencing, and Heritable Transcriptional States, *Microbiological Reviews* (1992) 56:543–560.
Levis et al., Transposons in Place of Telomeric Repeats at a Drosophila Telomere, *Cell* (1993) 75:1083–1093.
Loo et al., Silencers and Domains of Generalized Repression, *Science* (1994) 264:1768–1771.
Oliver et al., The complete DNA sequence of yeast chromosome III, *Nature* (1992) 357:38–46.
Pimpinelli et al., Transposable elements are stable structural components of *Drosophila Melanogaster* heterochromatin, *Proc. Natl. Acad. Sci. USA*. (1995) 92:3804–3808.
Roth, S., Chromatin–mediated transcriptional repression in yeast, *Curr. Opin. Genet. Dev.* (1995)5:168–173.
SanMiguel et al., Nested Retrotransposons in the Intergenic Regions of the Maize Genome, *Science* (1996) 274:765–768.
Varmus et al., Retroviruses, In *Mobile DNA* (ed. D.E. Berg and M.M. Howe), pp. 53–108. American Society for Microbiology, Washington, D.C.
Voytas et al., A copia–like transposable element family in *Arabidopsis thaliana, Nature* (1988) 336:242–244.
Voytas et al. Yeast retrotransposon revealed, *Nature* (1992) 358:717.
Voytas et al., Yeast retrotransposons and tRNAs, *Trends Genet.* (1993) 9:421–417.
Xiong et al., Origin and evolution of retroelements based upon their reverse transcriptase sequences, *EMBO J.* (1990) 9:3353–3362.
Zou et al., The Saccharomyces Ty5 retrotransposon family is associated with origins of DNA replication at the telomeres and the silent mating locus HMR, *Proc. Natl. Acad. Sci. USA*. (1995) 92:920–924.

*Primary Examiner*—Nancy Degen
*Assistant Examiner*—William Sandals
*Attorney, Agent, or Firm*—Greenlee, Winner and Sullivan, P.C.

[57] ABSTRACT

The present disclosure provides retrotransposons and retrotransposon derivatives and methods for their uses. Specifically, the present invention provides Ty5-6p and derivatives. Ty5-6p and its derivatives integrate preferentially in the genome of eukaryotes in silent chromatin and in regions like silent chromatin. Ty5-6p insertions can be used to regulate the life span of cells, to genetically mark cells, to deliver gene therapy and to identify genes involved in development and in senescence.

13 Claims, 15 Drawing Sheets

RNA Binding

```
Ty5-6  CMICGAD.HRLSNC
Tal-3  CWYCKKEGHVKKDC
copia  CHHCGREGHIKKDC
+++
```

Integrase

```
Ty5-6  PLQMVQADLCG <63> DNGTEFVNKNLHAFFKSKGI <12> NGAVERAHRTIEERTR <12> WSEA
Ty1H3  PFQYLHTDIFG <61> DRGSEYTNRTLHKFLEKNGI <12> HGVAERLNRTLDDCR <12> MFSA
Tal-1  VLRYHADLWG <60> DNGLEFCNLKFDAYCKEHGI <12> NGVAERMNRTIMEKVR <12> WAEA
copia  PLFVHSDVCG <59> DNGREYLSNEMRQFCVKKGI <12> NGVSERMIRTITEKAR <12> WGEA
```

Reverse Transcriptase

```
Ty5-6  KARLVAQGHTQKAGIDYQETFAPV <21> QMDVDTAFLNSKMNEPVYVKQP <61> YIAL VDDL
Ty1H3  KARFVARGDIQHPDTYDSGMQSNT <21> QLDISSAYLYADIKEELYIRPP <55> TICLFVDDM
Tal-3  KAQLVAKGYTHREGVDYQEIFALV <21> QMDVKTAFLHGELEEELYMEQP <62> YLLLYVDDM
copia  KARLVARGFTQKYQIDYEETFAPV <21> QMDVKTAFLNGTLKEEIYMRLP <61> YVLLYVDDV
```

RNase H

```
Ty5-6  SSTEAEYITASETVMEIEW <24> IKLSKHPVFHT.RTKHIALRYHK <16> TKRQVADIFTKIL
Ty1H3  STTEAEIHAISESVPLLNN <24> ISIIKSTNEEKFRNRFFGTKAMR <16> TKKNIADVMTKPL
Tal-3  STTEAFMALTEAAKEALW <24> ICLFKNSTHHE.RTKHIDVRYNF <16> TSRNPADALTKSI
copia  SSTEAEYMALFEAVREALW <25> HSIANNPSCHK.RAKHIDIKYHF <16> TENQLADIFTKPL
```

FIG. 1B

FIG. 3A
1. *HIS3* marker gene inactivated by intron in opposite orientation
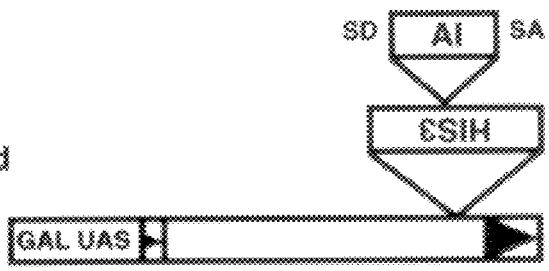
Transcription and Splicing
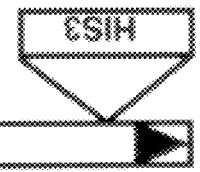
Reverse Transcription and Integration
2. *HIS3* gene active due to intron removal from Ty5 transcript
FIG. 3B   Ty5-5p (ySZ127)   Ty5-6p (ySZ128)
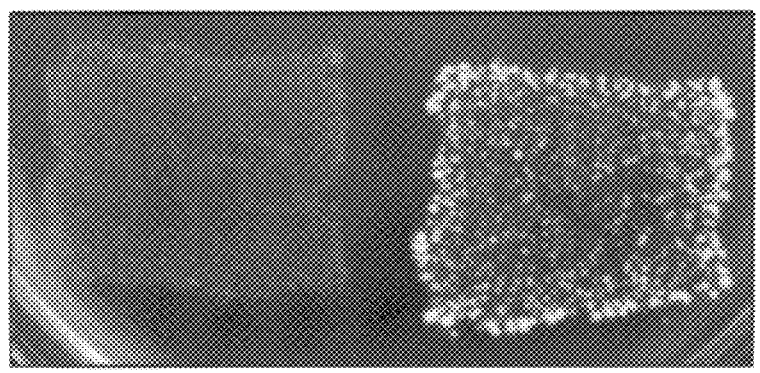
FIG. 3C
| | Colonies on YPD (X $10^4$) | Colonies on SC-His | Rate of His⁺ cell formation |
|---|---|---|---|
| Expt. 1: | 89 | 134 | $1.5 \times 10^{-4}$ |
| Expt. 2: | 63 | 87 | $1.4 \times 10^{-4}$ |

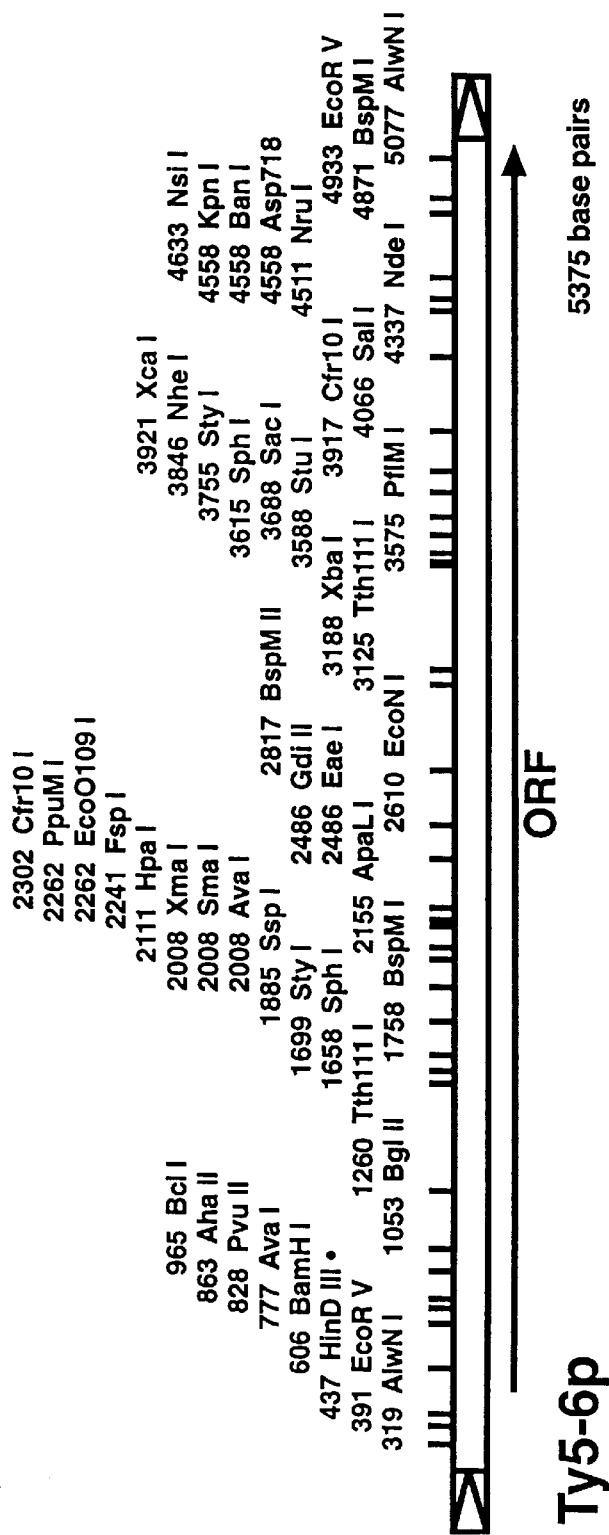
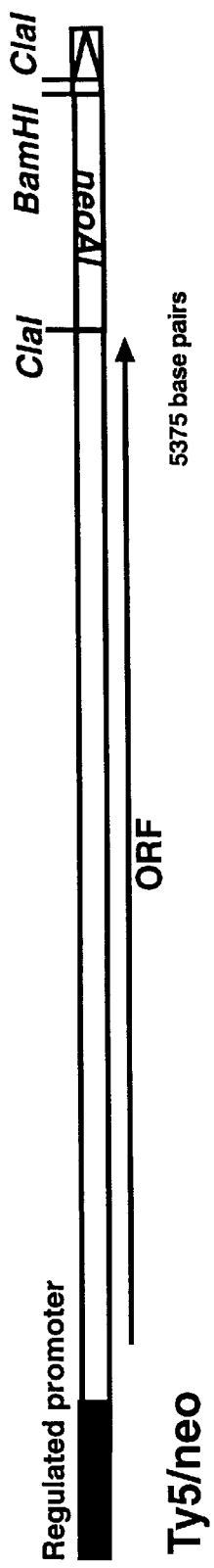
FIG. 7
FIG. 8

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
        (A) LENGTH: 6660 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharomyces paradoxus
        (B) STRAIN: NRRL Y-17217

(ix) FEATURE:
        (A) NAME/KEY: CDS
        (B) LOCATION: 1441..6321

(ix) FEATURE:
        (A) NAME/KEY: misc_feature
        (B) LOCATION: 1228..6602
        (D) OTHER INFORMATION: /function= "retrotransposon"
            /product= "Ty5-6p"

(ix) FEATURE:
        (A) NAME/KEY: misc_feature
        (B) LOCATION: 1228..1478
        (D) OTHER INFORMATION: /function= "5' LTR of Ty5-6p"

(ix) FEATURE:
        (A) NAME/KEY: misc_feature
        (B) LOCATION: 6352..6602
        (D) OTHER INFORMATION: /function= "3' LTR of Ty5-6p"

(ix) FEATURE:
        (A) NAME/KEY: misc_feature
        (B) LOCATION: 2852..4827
        (D) OTHER INFORMATION: /function= "integrase region coding
            region of Ty5-6p"

(xi) SEQUENCE DESCRIPTION: SEQ ID NO:1:

```
GGGACAACCC CCCAACGCCA ATAAACATCG TTCCTCATCC TCAGAAAAAC GTACACTCCT      60

CATCATAAAC TTCATATAGT TACAATTATG ACTATGTATG AAATTTTGTA GCGCCCCTGT     120

TTCTTGGGGA TCTACAAATC AATCAACCAG CTCGTAATTG TGTGAGAACC GATTGCTGAT     180

TCTGCGCATT TATGCATAAT TATTGTCCTC CAGTAGTTGC CTTGGTTTGG TTATGCAGGA     240

ATTTTCAGTA GTCATTTTTT TAAGCAACAA ATGACTTAAA CCTACACATG TTTCTTAGAC     300

AAAGTACATA CGCAAATAAG ATAGCAGACA AAGCATTAAT ATAATAACAA GTCCTTGTTA     360

TTCTTATTTT TATCGTCCTT TTTCTGTTTT CCGCTCGGGT GACGACAGTT CAAATCTCTT     420

CCTTTGGCGG TTGATTCAGT AATTCTTCAA TTATTTGAGA GAGTCCTAAC GGCCTAGTCA     480

TGCATGAGAA TCTTTTAACC ACCTTCCCAT TTCGGTCTAT CAAAAACTTT TCAAAATTCC     540

ACTTTATCAT TTTTATTCCA GATTTCCCGC TCACTGAGTT TTTTAAGAAC TTGTAGACAG     600

GATCTTGCTT TTGCCCATTA CAACGGATCT TATGTAGGAT AGGGAAGGTC ACACCGAATT     660

TATTCTGACA AAACTTATTG ATCTCCTCAT CCTTCTCAAA CTCTTGATTT CCAAATTGAC     720

CGCAAGGAAA GGCCCGATCA TCAGACCATG TGATTTGTAT TTTTCGTACA AGTACTCTAA     780

TTCCTTATAT TGTGGTGTGA ATGCACCATG AGATGCTACA TTAACTATCA GTACCACTTT     840

GTTACGCAAG GAGCTAAAGG GGAATGGATT TCCATCTTCA TCTATGGGCG CAAAAGAATA     900

AAATTCTTGC ATCGAAACTT ATATAGTGTT CCTTGGTTGA TGTTCCTTGT GCCGAATTAC     960

GATTAGAGAA ACTCGCTGTG CACAATACCA CCTACATGAC TAAATTCTGT CTGTACACTA    1020

CTTACTGTAT TATATAATCA CTGTAGATGT GTTAACTGTA AGCACTCTCT GTAGCAAAGG    1080
```

-continued

```
TGAGTCCGGA TTTAAGCACT TATGGACGTG GCAAACGAGG GATGACTCGC TTACCCTATA      1140

AAAATAGGGA ACAGAAGGGG AAAAGGAACT ACGGAGAAGT TCCACATGAA GACGGTAGTG      1200

GGGAATGTCG AGGGGATAC TGTCGTATGT TGAATGTGAT AACCCAAAAG CATGATATGG       1260

GTAATGTTTC AGTACTGTTT CAGAATTGTT TCAGTAATGT TTTAGACAAG GAAAACATAG      1320

AGCAGCAAAC CTCCGATCCG ACAGTACTTA AGAAACCATA GTTTCTGTGT ACAAGAGTAG      1380

TACCTATGTA ATTCTTACAT TTACATAACA TATAGAAAGG TCCAATAAAC TTACAACATT      1440
```

| | | | | | | | | | | | | | | | | |
|---|---|---|---|---|---|---|---|---|---|---|---|---|---|---|---|---|
| ATG | ACA | TAT | AAG | CTA | GAT | CGT | AAT | TCA | CTA | CGT | CAA | CAG | GTT | ATG | AGC | 1488 |
| Met | Thr | Tyr | Lys | Leu | Asp | Arg | Asn | Ser | Leu | Arg | Gln | Gln | Val | Met | Ser | |
| 1 | | | 5 | | | | | 10 | | | | | 15 | | | |

```
CCT GAG AGC AAT GCT TCA GAG ACC ATA ATT AAT CTA TCT AAT CCC AAC        1536
Pro Glu Ser Asn Ala Ser Glu Thr Ile Ile Asn Leu Ser Asn Pro Asn
            20                  25                  30

AAT TAT AAA CAG TGG CTG TAC GGT ATC GAG ACC GCT GCT GAA TAT GCT        1584
Asn Tyr Lys Gln Trp Leu Tyr Gly Ile Glu Thr Ala Ala Glu Tyr Ala
        35                  40                  45

AAC GAA TAT ATG AAC GAA TTC GTT CAT ACC GGA GAT ATC CAA TCA ATG        1632
Asn Glu Tyr Met Asn Glu Phe Val His Thr Gly Asp Ile Gln Ser Met
    50                  55                  60

AAA AGG GAT TAC AAT CTC AGC GCG AAT GAT GAA AGC TTT GTC AAA ACC        1680
Lys Arg Asp Tyr Asn Leu Ser Ala Asn Asp Glu Ser Phe Val Lys Thr
65                  70                  75                  80

GTA TTT AAC AGT TTC CTG GTA AAG CTC TAC AAG AAA ACT ATC GTG GGT        1728
Val Phe Asn Ser Phe Leu Val Lys Leu Tyr Lys Lys Thr Ile Val Gly
                85                  90                  95

GAA GCT GCA TGT GAA ATG AAC TGG ATA TGT GAT GAT TCA CTT GGA AGG        1776
Glu Ala Ala Cys Glu Met Asn Trp Ile Cys Asp Asp Ser Leu Gly Arg
            100                 105                 110

GTC TCT GCT TAT GAT ATT TTC TCG CAC TTC GAA GAA AAC TAT AAT GAA        1824
Val Ser Ala Tyr Asp Ile Phe Ser His Phe Glu Glu Asn Tyr Asn Glu
        115                 120                 125

GTC ACT ATT GGA TCC AGG CTT ACT CTT ATA GAG GAC TTA CCA AAT ATA        1872
Val Thr Ile Gly Ser Arg Leu Thr Leu Ile Glu Asp Leu Pro Asn Ile
    130                 135                 140

TCC TCC AAG CCT GTA GAT GAA ATC GCT TCC TTT TTG AAA ACC CTA TTC        1920
Ser Ser Lys Pro Val Asp Glu Ile Ala Ser Phe Leu Lys Thr Leu Phe
145                 150                 155                 160

ACA ATG CTT GAA GAC AAT AGC GAA GAA CAG GAC AAA AAG AAA AGA CGC        1968
Thr Met Leu Glu Asp Asn Ser Glu Glu Gln Asp Lys Lys Lys Arg Arg
                165                 170                 175

GAT ACC AAT ATC GCG TTG CTA TTA ATG ACC TTC TTA CCC GAG TTA AAG        2016
Asp Thr Asn Ile Ala Leu Leu Leu Met Thr Phe Leu Pro Glu Leu Lys
            180                 185                 190

GAA TCA TTC CAC GAG AAA TTC GGT GAC TCT AAA GCT CTT CAG CTG TCA        2064
Glu Ser Phe His Glu Lys Phe Gly Asp Ser Lys Ala Leu Gln Leu Ser
        195                 200                 205

CAA GTC ATT AGA TTC TGT AAA TTA AAG GCG TCA TCG AAT TCA TTA TCT        2112
Gln Val Ile Arg Phe Cys Lys Leu Lys Ala Ser Ser Asn Ser Leu Ser
    210                 215                 220

TCA GTC TCA GAT ACA TTG GTT GCA CAA GAC AGA AGA AGC TAT CAA AAG        2160
Ser Val Ser Asp Thr Leu Val Ala Gln Asp Arg Arg Ser Tyr Gln Lys
225                 230                 235                 240

AAA GGA AAT AAG GGA TGT ATG ATT TGT GGG GCT GAT CAT CGC TTA AGC        2208
Lys Gly Asn Lys Gly Cys Met Ile Cys Gly Ala Asp His Arg Leu Ser
                245                 250                 255

AAC TGT TCT CTG CTT AAA AGA AGA ATA CCA GAA GCC AGA ATC TTT AAA        2256
Asn Cys Ser Leu Leu Lys Arg Arg Ile Pro Glu Ala Arg Ile Phe Lys
            260                 265                 270
```

```
TTA TAT CCT AAT GAC AAG ACG AAT AGA TCT TCA TCT GCT AGT GTT GCG   2304
Leu Tyr Pro Asn Asp Lys Thr Asn Arg Ser Ser Ser Ala Ser Val Ala
        275                 280                 285

ATT CCT GAC TAT GAA ACG CAA GGC CAA ACA GCA GGA CAG ATA ACA CCA   2352
Ile Pro Asp Tyr Glu Thr Gln Gly Gln Thr Ala Gly Gln Ile Thr Pro
        290                 295                 300

AAG TCC TGG CTC TGT ATG TTA TCT TCG ACC GTC CCA GCT ACC AAA TCC   2400
Lys Ser Trp Leu Cys Met Leu Ser Ser Thr Val Pro Ala Thr Lys Ser
305                 310                 315                 320

TCA GAT TGG ATT TGT GAC ACA GGA TGT ACT TCA CAC ATG TGC CAC GAC   2448
Ser Asp Trp Ile Cys Asp Thr Gly Cys Thr Ser His Met Cys His Asp
                325                 330                 335

CGT TCT ATG TTC TCA TCA TTT ACT AGA TCC TCT AAG AAA GAC TTT GTC   2496
Arg Ser Met Phe Ser Ser Phe Thr Arg Ser Ser Lys Lys Asp Phe Val
        340                 345                 350

AGA GGA GTC GGC GGT TCC ATA CCC ATC ATG GGC TCC GGG ACT GTA AAC   2544
Arg Gly Val Gly Gly Ser Ile Pro Ile Met Gly Ser Gly Thr Val Asn
        355                 360                 365

ATC GGC ACT GTT CAA TTA AAT GAC GTA TCC TAC GTC CCT GAT TTA CCA   2592
Ile Gly Thr Val Gln Leu Asn Asp Val Ser Tyr Val Pro Asp Leu Pro
370                 375                 380

GTC AAC CTA ATA TCC ATT TGG AAA CTA TGT GCT AAA TCC AAC TCT TCT   2640
Val Asn Leu Ile Ser Ile Trp Lys Leu Cys Ala Lys Ser Asn Ser Ser
385                 390                 395                 400

GTT ACG TTC ACA AAA GAG GGT GTC ACT GTG AAA TCA CCT GAT GAC GTG   2688
Val Thr Phe Thr Lys Glu Gly Val Thr Val Lys Ser Pro Asp Asp Val
                405                 410                 415

ATT TCT ACG GCT GGG AAG TTA AAC AAT TAT CTG TAC ATT TTC GAT GAT   2736
Ile Ser Thr Ala Gly Lys Leu Asn Asn Tyr Leu Tyr Ile Phe Asp Asp
                420                 425                 430

CTT ACG CCC GTA ACT ACC TTC TCT TCG CAA AAT TAC TTC TGC TCT AAA   2784
Leu Thr Pro Val Thr Thr Phe Ser Ser Gln Asn Tyr Phe Cys Ser Lys
        435                 440                 445

ACA TTG GAT TCA TCT AAA ATG ATA ACT TCC GCA GCG TTT CAT ACC GTT   2832
Thr Leu Asp Ser Ser Lys Met Ile Thr Ser Ala Ala Phe His Thr Val
450                 455                 460

GCA GAT AAA ATG TTG TCG CAA CAC ATT TCT CCC ACT GCT CTC CCG GTA   2880
Ala Asp Lys Met Leu Ser Gln His Ile Ser Pro Thr Ala Leu Pro Val
465                 470                 475                 480

AAA TGG CAT GCT CGT ATG GGC CAT CCC GGA GCA GAT ATT TAC AAT TCC   2928
Lys Trp His Ala Arg Met Gly His Pro Gly Ala Asp Ile Tyr Asn Ser
                485                 490                 495

TTG GCT AGA ACT CTG CGT TTT CCA AAA TTT AAG ACG GCT GAA TAC ACT   2976
Leu Ala Arg Thr Leu Arg Phe Pro Lys Phe Lys Thr Ala Glu Tyr Thr
                500                 505                 510

ATT TGT CCT ACC TGC TCA CTA GCA AAA GGA ATC ATC AAA AAG GGT AAA   3024
Ile Cys Pro Thr Cys Ser Leu Ala Lys Gly Ile Ile Lys Lys Gly Lys
        515                 520                 525

GTC TCG CTC AAA AAA TAT ACC CAA CCT CTT CAA ATG GTA CAG GCT GAT   3072
Val Ser Leu Lys Lys Tyr Thr Gln Pro Leu Gln Met Val Gln Ala Asp
530                 535                 540

CTC TGT GGT GGG TTT CGC TAC CAA GAG TTT CAG TCA AAT AAA TAT TTT   3120
Leu Cys Gly Gly Phe Arg Tyr Gln Glu Phe Gln Ser Asn Lys Tyr Phe
545                 550                 555                 560

CTT ACT ATC CGT GAT GCC TAT AGT CGC TAC TAC TCT GTA ATA CAT TTA   3168
Leu Thr Ile Arg Asp Ala Tyr Ser Arg Tyr Tyr Ser Val Ile His Leu
                565                 570                 575

AAA TCC AAA GCA GAC GCT CCG ATA AAA TTC ATG GAA TGG ATC AAC GAA   3216
Lys Ser Lys Ala Asp Ala Pro Ile Lys Phe Met Glu Trp Ile Asn Glu
                580                 585                 590
```

-continued

```
ACC GAA CAA TAC TTT AGC TCC CGG GGT GGA TTC AAA GTC GGA TCT GTT      3264
Thr Glu Gln Tyr Phe Ser Ser Arg Gly Gly Phe Lys Val Gly Ser Val
        595                 600                 605

CGT ACA GAC AAT GGT ACA GAA TTC GTA AAT AAA AAT CTT CAT GCG TTT      3312
Arg Thr Asp Asn Gly Thr Glu Phe Val Asn Lys Asn Leu His Ala Phe
610                 615                 620

TTT AAA TCT AAA GGA ATA GAG CAT CAG TTA ACT ATT CCA TAT CAT AGT      3360
Phe Lys Ser Lys Gly Ile Glu His Gln Leu Thr Ile Pro Tyr His Ser
625                 630                 635                 640

TAT CAA AAT GGT GCT GTT GAA CGT GCA CAT CGT ACC ATC GAA GAA CGC      3408
Tyr Gln Asn Gly Ala Val Glu Arg Ala His Arg Thr Ile Glu Glu Arg
                645                 650                 655

ACT CGT TGT CTC CTT ATC GGG GGG CGT GTT CCT CCG TCC TTG TGG TCT      3456
Thr Arg Cys Leu Leu Ile Gly Gly Arg Val Pro Pro Ser Leu Trp Ser
            660                 665                 670

GAA GCT GTT TCT TGC GCA GTC TAT TTA ATC AAT AGG TCC CCT GTA GTG      3504
Glu Ala Val Ser Cys Ala Val Tyr Leu Ile Asn Arg Ser Pro Val Val
        675                 680                 685

TCC AAA AAT AAC AGT ATC CCA TAC TGC CGG TGG TTC AAC ATC CCC GCA      3552
Ser Lys Asn Asn Ser Ile Pro Tyr Cys Arg Trp Phe Asn Ile Pro Ala
690                 695                 700

AAA GAT TTC GGT ATC GCA CAT CTT CGA ATT TTT GGA TGT ACA GCA TAC      3600
Lys Asp Phe Gly Ile Ala His Leu Arg Ile Phe Gly Cys Thr Ala Tyr
705                 710                 715                 720

GCA ACC TTA CAA CCT AGT CTT CGA GAC GGC AAA CTT GCC CCA ACT GTC      3648
Ala Thr Leu Gln Pro Ser Leu Arg Asp Gly Lys Leu Ala Pro Thr Val
                725                 730                 735

ATA TCT GGT GTT ATG GTT GGC TAT GAC TCT AAC CAT CGA GGA TAC AGG      3696
Ile Ser Gly Val Met Val Gly Tyr Asp Ser Asn His Arg Gly Tyr Arg
            740                 745                 750

ATT TAT CAT CCC GAA ACT GGC CGC ATC TTT GTG AGC AGT CAA GTT CGA      3744
Ile Tyr His Pro Glu Thr Gly Arg Ile Phe Val Ser Ser Gln Val Arg
        755                 760                 765

TTT GAC GAA CAC ATG TTT CCT CTT GCT GAT ACA GAG GCA GTT CAC GTC      3792
Phe Asp Glu His Met Phe Pro Leu Ala Asp Thr Glu Ala Val His Val
770                 775                 780

TCT CAC GAC TTT GCC ACT TCC GCT ATT GGG GGG GTG TCC AAA TAT CCT      3840
Ser His Asp Phe Ala Thr Ser Ala Ile Gly Gly Val Ser Lys Tyr Pro
785                 790                 795                 800

GAA ACA GGG TCA ACC GTC TCT GCT CCA AAG AAC GAC GGA TCT GAC TTG      3888
Glu Thr Gly Ser Thr Val Ser Ala Pro Lys Asn Asp Gly Ser Asp Leu
                805                 810                 815

GCA AAT TTG CCA ATA ACT GTT CCC AAA AAT GTA AAT CAA CCA GCA CAT      3936
Ala Asn Leu Pro Ile Thr Val Pro Lys Asn Val Asn Gln Pro Ala His
            820                 825                 830

AAA CCT AAT ACC AGT AAC ATC TCT TCC TCT GAT GAT GAT GAG GAT ATT      3984
Lys Pro Asn Thr Ser Asn Ile Ser Ser Ser Asp Asp Asp Glu Asp Ile
        835                 840                 845

TCA ATG GAA ATC GAA ATG GAA AAA CCT ATC CCT GAG TGT AAC CAA GAC      4032
Ser Met Glu Ile Glu Met Glu Lys Pro Ile Pro Glu Cys Asn Gln Asp
850                 855                 860

AAC TTA CCA AAC TCC GGA TGT CCA CCA ACA AGG ATA CAA CAT TCT AAC      4080
Asn Leu Pro Asn Ser Gly Cys Pro Pro Thr Arg Ile Gln His Ser Asn
865                 870                 875                 880

TTT GAA TCC TTA CCA ACC GTG TCT ACC GAA GAC GAA ACT AAT TCT TCT      4128
Phe Glu Ser Leu Pro Thr Val Ser Thr Glu Asp Glu Thr Asn Ser Ser
                885                 890                 895

ATG GAG AAA ACT CCT GAA AGA GTT CCA GCG GCA CTA ACT TAT CGA GAA      4176
Met Glu Lys Thr Pro Glu Arg Val Pro Ala Ala Leu Thr Tyr Arg Glu
            900                 905                 910
```

-continued

| | | | | | | | | | | | | | | | |
|---|---|---|---|---|---|---|---|---|---|---|---|---|---|---|---|
| ATT | CCA | AAA | TCA | TCC | GAT | TCA | GAA | TAT | ATT | CCG | ACA | TGC | CGA | AAT | AGA | 4224 |
| Ile | Pro | Lys | Ser | Ser | Asp | Ser | Glu | Tyr | Ile | Pro | Thr | Cys | Arg | Asn | Arg |
| | | 915 | | | | 920 | | | | | 925 | | | | |

| ACT | AGA | CGT | GTT | AAA | AGA | ACT | AAT | AAG | AAA | CCA | ACG | CGA | TCC | CGC | GAA | 4272 |
| Thr | Arg | Arg | Val | Lys | Arg | Thr | Asn | Lys | Lys | Pro | Thr | Arg | Ser | Arg | Glu |
| | 930 | | | | | 935 | | | | | 940 | | | | |

| ATA | GAA | ATA | TAT | GAT | ATA | TCA | CGT | CCA | AAC | GTA | ATA | TCG | AGT | GAC | AAC | 4320 |
| Ile | Glu | Ile | Tyr | Asp | Ile | Ser | Arg | Pro | Asn | Val | Ile | Ser | Ser | Asp | Asn |
| 945 | | | | | 950 | | | | | 955 | | | | | 960 |

| TTA | CCT | GAA | GTT | AGA | AGT | GCC | AAG | CAA | AGA | AAG | ACG | GTG | TCC | AAT | ACA | 4368 |
| Leu | Pro | Glu | Val | Arg | Ser | Ala | Lys | Gln | Arg | Lys | Thr | Val | Ser | Asn | Thr |
| | | | | 965 | | | | | 970 | | | | | 975 | |

| AAT | GAT | ACT | GTA | GCA | AGG | ACA | AAT | AGA | CTT | CCA | ACC | GTG | CTA | CGA | ACT | 4416 |
| Asn | Asp | Thr | Val | Ala | Arg | Thr | Asn | Arg | Leu | Pro | Thr | Val | Leu | Arg | Thr |
| | | | 980 | | | | | 985 | | | | | 990 | | |

| CTA | GAC | TCA | AAC | AAC | ATT | GAC | ACG | CTG | CAT | GTT | GCC | AGT | ACT | GGT | GAA | 4464 |
| Leu | Asp | Ser | Asn | Asn | Ile | Asp | Thr | Leu | His | Val | Ala | Ser | Thr | Gly | Glu |
| | | | 995 | | | | | 1000 | | | | | 1005 | | |

| GAA | GTG | TCC | ATC | GAA | AGA | CTT | TCA | AGC | ATG | GCT | CTT | CAG | GAA | GCG | AAG | 4512 |
| Glu | Val | Ser | Ile | Glu | Arg | Leu | Ser | Ser | Met | Ala | Leu | Gln | Glu | Ala | Lys |
| | | 1010 | | | | | 1015 | | | | | 1020 | | | |

| AAC | AAT | TCC | GCC | AGA | ACT | AAT | CAA | GCT | AAT | TCT | CTT | ACT | GAT | TGG | TTT | 4560 |
| Asn | Asn | Ser | Ala | Arg | Thr | Asn | Gln | Ala | Asn | Ser | Leu | Thr | Asp | Trp | Phe |
| 1025 | | | | | 1030 | | | | | 1035 | | | | | 1040 |

| CCA | GTA | GGC | GCA | ATG | CCG | ATA | CCT | GAC | CAG | AGG | TAT | CTA | TCC | GTT | CAC | 4608 |
| Pro | Val | Gly | Ala | Met | Pro | Ile | Pro | Asp | Gln | Arg | Tyr | Leu | Ser | Val | His |
| | | | | 1045 | | | | | 1050 | | | | | 1055 | |

| GAT | GGA | ACA | TAT | ATC | AGC | GAC | TCA | CAA | GAT | GTG | GGT | GAT | ACT | GAC | CTC | 4656 |
| Asp | Gly | Thr | Tyr | Ile | Ser | Asp | Ser | Gln | Asp | Val | Gly | Asp | Thr | Asp | Leu |
| | | | 1060 | | | | | 1065 | | | | | 1070 | | |

| ACT | CCT | GCT | GTA | ACC | AGG | CTA | GTT | ACT | GAA | GAG | AAT | TCA | ATC | GAA | TCT | 4704 |
| Thr | Pro | Ala | Val | Thr | Arg | Leu | Val | Thr | Glu | Glu | Asn | Ser | Ile | Glu | Ser |
| | | | 1075 | | | | | 1080 | | | | | 1085 | | |

| CCT | CCA | TCG | TTG | GAT | TCA | TCG | CCT | CCA | AAT | ACC | TCA | TTT | AAC | GCG | GCT | 4752 |
| Pro | Pro | Ser | Leu | Asp | Ser | Ser | Pro | Pro | Asn | Thr | Ser | Phe | Asn | Ala | Ala |
| | | 1090 | | | | | 1095 | | | | | 1100 | | | |

| CTA | ACT | GCT | ATT | ATC | CAT | AGC | ACA | AAA | AAA | GGA | AAC | CCG | AAA | ACC | TAT | 4800 |
| Leu | Thr | Ala | Ile | Ile | His | Ser | Thr | Lys | Lys | Gly | Asn | Pro | Lys | Thr | Tyr |
| 1105 | | | | | 1110 | | | | | 1115 | | | | | 1120 |

| GCC | CAA | GCA | ATG | GGA | AGG | CCT | GAC | TTT | CAA | GAA | TGG | CAC | AAC | GCA | TGC | 4848 |
| Ala | Gln | Ala | Met | Gly | Arg | Pro | Asp | Phe | Gln | Glu | Trp | His | Asn | Ala | Cys |
| | | | | 1125 | | | | | 1130 | | | | | 1135 | |

| CTC | AAG | GAA | CTT | TCC | GCG | TTC | AAA | GAT | CAC | AAT | ACG | TAC | AAA | TTG | GTG | 4896 |
| Leu | Lys | Glu | Leu | Ser | Ala | Phe | Lys | Asp | His | Asn | Thr | Tyr | Lys | Leu | Val |
| | | | 1140 | | | | | 1145 | | | | | 1150 | | |

| TCT | CTT | CCA | AAG | CAA | AGA | AGA | GCT | CTT | GGA | TCG | CGC | TGG | GTA | TTC | ACA | 4944 |
| Ser | Leu | Pro | Lys | Gln | Arg | Arg | Ala | Leu | Gly | Ser | Arg | Trp | Val | Phe | Thr |
| | | | 1155 | | | | | 1160 | | | | | 1165 | | |

| ATA | AAA | GAC | TCC | GGG | ACG | TAC | AAA | GCT | CGC | CTT | GTC | GCC | CAA | GGA | CAT | 4992 |
| Ile | Lys | Asp | Ser | Gly | Thr | Tyr | Lys | Ala | Arg | Leu | Val | Ala | Gln | Gly | His |
| | | 1170 | | | | | 1175 | | | | | 1180 | | | |

| ACT | CAA | AAG | GCT | GGT | ATT | GAC | TAT | CAA | GAA | ACT | TTT | GCA | CCA | GTC | ATT | 5040 |
| Thr | Gln | Lys | Ala | Gly | Ile | Asp | Tyr | Gln | Glu | Thr | Phe | Ala | Pro | Val | Ile |
| 1185 | | | | | 1190 | | | | | 1195 | | | | | 1200 |

| CGA | TAT | GAC | TCT | GTT | AGA | TTA | TTT | CTG | GCC | CTT | GCT | AGC | TGC | CTC | AAA | 5088 |
| Arg | Tyr | Asp | Ser | Val | Arg | Leu | Phe | Leu | Ala | Leu | Ala | Ser | Cys | Leu | Lys |
| | | | | 1205 | | | | | 1210 | | | | | 1215 | |

| CTA | ATA | GTA | TAT | CAG | ATG | GAC | GTT | GAC | ACC | GCG | TTT | CTA | AAC | TCA | AAA | 5136 |
| Leu | Ile | Val | Tyr | Gln | Met | Asp | Val | Asp | Thr | Ala | Phe | Leu | Asn | Ser | Lys |
| | | | 1220 | | | | | 1225 | | | | | 1230 | | |

```
ATG AAT GAG CCG GTA TAC GTA AAA CAA CCA CCC GGA TTT ATT AAT GAA        5184
Met Asn Glu Pro Val Tyr Val Lys Gln Pro Pro Gly Phe Ile Asn Glu
        1235                1240                1245

AGT AAT CCC GAC TAT GTA TGG GAA CTA TAC GGC GGT ATG TAT GGA CTC        5232
Ser Asn Pro Asp Tyr Val Trp Glu Leu Tyr Gly Gly Met Tyr Gly Leu
    1250                1255                1260

AAG CAA GCC CCA TTA CTA TGG AAC GAA CAT ATC AAC AAT ACT CTT CAA        5280
Lys Gln Ala Pro Leu Leu Trp Asn Glu His Ile Asn Asn Thr Leu Gln
1265                1270                1275                1280

AAG ATT GGT TTT CGT CGA CAT GAA GGC GAA CAT GGC TTA TAC TTT CGT        5328
Lys Ile Gly Phe Arg Arg His Glu Gly Glu His Gly Leu Tyr Phe Arg
                1285                1290                1295

TCC ACA TCT GAT GGT CCC ATC TAC ATT GCC CTA TAC GTA GAC GAC TTA        5376
Ser Thr Ser Asp Gly Pro Ile Tyr Ile Ala Leu Tyr Val Asp Asp Leu
            1300                1305                1310

CTT GTT GCT GCT CCC TCT CCG AAA ATA TAT GAC AGG GTT AAG CAG AAA        5424
Leu Val Ala Ala Pro Ser Pro Lys Ile Tyr Asp Arg Val Lys Gln Lys
        1315                1320                1325

CTA ACG AAG TTA TAC TCA ATG AAG GAT CTA GGT AAA GTT GAC AAA TTC        5472
Leu Thr Lys Leu Tyr Ser Met Lys Asp Leu Gly Lys Val Asp Lys Phe
    1330                1335                1340

CTC GGT CTT AAC ATT AAT CAA TTT TCA AAT GGA GAC ATC ACT CTC TCA        5520
Leu Gly Leu Asn Ile Asn Gln Phe Ser Asn Gly Asp Ile Thr Leu Ser
1345                1350                1355                1360

CTT CAA GAC TAT ATT GCT AAA GCT GCA TCT GAA AGC GAA ATA AAC ATA        5568
Leu Gln Asp Tyr Ile Ala Lys Ala Ala Ser Glu Ser Glu Ile Asn Ile
                1365                1370                1375

TGT AAG CCT ACA CAG ACT CCG CTC TGT GAC TCA AAG CCT CTT TTC GAA        5616
Cys Lys Pro Thr Gln Thr Pro Leu Cys Asp Ser Lys Pro Leu Phe Glu
            1380                1385                1390

ACA ACT TCC CCG CAC CTA AAG GAC ATC ACT CCT TAT CAG AGC ATA GTT        5664
Thr Thr Ser Pro His Leu Lys Asp Ile Thr Pro Tyr Gln Ser Ile Val
        1395                1400                1405

GGA CAG CTT CTC TTT TGT GCA AAT ACT GGT CGT CCT GAC ATA TCT TAT        5712
Gly Gln Leu Leu Phe Cys Ala Asn Thr Gly Arg Pro Asp Ile Ser Tyr
    1410                1415                1420

CCG GTC TCA CTA CTC TCC AGG TTT CTT CGC GAA CCT CGC GCA ATC CAT        5760
Pro Val Ser Leu Leu Ser Arg Phe Leu Arg Glu Pro Arg Ala Ile His
1425                1430                1435                1440

TTG GAG TCT GCT CGA CGA GTT CTA CGG TAC CTA TAT ACC ACC AGA AGT        5808
Leu Glu Ser Ala Arg Arg Val Leu Arg Tyr Leu Tyr Thr Thr Arg Ser
                1445                1450                1455

ATG TGT CTC AAG TAT CGT TCT GGA TCT CTG TTG GCA CTA ACT GTA TAT        5856
Met Cys Leu Lys Tyr Arg Ser Gly Ser Leu Leu Ala Leu Thr Val Tyr
            1460                1465                1470

TGT GAT GCA TCT CAT GGA GCA ATT CAC GAT CTC CCA CAC TCT ACT GGG        5904
Cys Asp Ala Ser His Gly Ala Ile His Asp Leu Pro His Ser Thr Gly
        1475                1480                1485

GGG TAC GTG ACT CTA CTT GCT GGT GCT CCA GTT ACG TGG TCA TCA AAG        5952
Gly Tyr Val Thr Leu Leu Ala Gly Ala Pro Val Thr Trp Ser Ser Lys
    1490                1495                1500

AAA CTC AAG GGT GTG ATT CCT GTA TCA TCT ACT GAG GCA GAA TAC ATT        6000
Lys Leu Lys Gly Val Ile Pro Val Ser Ser Thr Glu Ala Glu Tyr Ile
1505                1510                1515                1520

ACT GCA AGT GAA ACT GTC ATG GAG ATA GAA TGG ATT CAA AAC TTG TTT        6048
Thr Ala Ser Glu Thr Val Met Glu Ile Glu Trp Ile Gln Asn Leu Phe
                1525                1530                1535

GAA CAC TTA GGC CAG CCA CTT ATC TCA TCA ACA TTA TAC GTA GAT AAT        6096
Glu His Leu Gly Gln Pro Leu Ile Ser Ser Thr Leu Tyr Val Asp Asn
            1540                1545                1550
```

-continued

```
GAA CCT GCT ATA AAA CTA TCT AAA CAT CCT GTA TTT CAC ACG AGA ACA        6144
Glu Pro Ala Ile Lys Leu Ser Lys His Pro Val Phe His Thr Arg Thr
        1555                1560                1565

AAA CAC ATT GCC TTG AGA TAT CAC AAG CTA AGA AGT GCA GTG GCA GCA        6192
Lys His Ile Ala Leu Arg Tyr His Lys Leu Arg Ser Ala Val Ala Ala
        1570                1575                1580

GGC ATA ATT ACC ATA GAG CAT GTT ATT ACA AAG AGA CAA GTT GCT GAC        6240
Gly Ile Ile Thr Ile Glu His Val Ile Thr Lys Arg Gln Val Ala Asp
1585                1590                1595                1600

ATA TTT ACA AAA ATC CTT CCA GCA GAA TCA TTC AAA GCA CAT AGG GCT        6288
Ile Phe Thr Lys Ile Leu Pro Ala Glu Ser Phe Lys Ala His Arg Ala
            1605                1610                1615

GTC ATG GTG AGG GAA CCA GAA ACT GCA AAA TAA CCACTCTCAT GCGTATTCAG      6341
Val Met Val Arg Glu Pro Glu Thr Ala Lys  *
        1620                1625

TTATGGGGGG ATGTTGAATG TGATAACCCA AAAGCATGAT ATGGGTAATG TTTCAGTACT      6401

GTTTCAGAAT TGTTTCAGTA ATGTTTTAGA CAAGGAAAAC ATAGAGCAGC AAACCTCCGA      6461

TCCGACAGTA CTTAAGAAAC CATAGTTTCT GTGTACAAGA GTAGTACCTA TGTAATTCTT      6521

ACATTTACAT AACATATAGA AAGGTCCAAT AAACTTACAA CATTATGACA TATAAGCTAG      6581

ATCGTAATTC ACTACGTCAA CATCGTACAC TTAAAATATA TGTATGTATC TGCACTATTT      6641

AGTCTTGTTT TATTGGGTG                                                   6660
```

(2) INFORMATION FOR SEQ ID NO:2:

(i) SEQUENCE CHARACTERISTICS:
        (A) LENGTH: 1626 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Tyr Lys Leu Asp Arg Asn Ser Leu Arg Gln Gln Val Met Ser
  1               5                  10                  15

Pro Glu Ser Asn Ala Ser Glu Thr Ile Ile Asn Leu Ser Asn Pro Asn
                 20                  25                  30

Asn Tyr Lys Gln Trp Leu Tyr Gly Ile Glu Thr Ala Ala Glu Tyr Ala
             35                  40                  45

Asn Glu Tyr Met Asn Glu Phe Val His Thr Gly Asp Ile Gln Ser Met
         50                  55                  60

Lys Arg Asp Tyr Asn Leu Ser Ala Asn Asp Glu Ser Phe Val Lys Thr
 65                  70                  75                  80

Val Phe Asn Ser Phe Leu Val Lys Leu Tyr Lys Thr Ile Val Gly
                 85                  90                  95

Glu Ala Ala Cys Glu Met Asn Trp Ile Cys Asp Asp Ser Leu Gly Arg
                100                 105                 110

Val Ser Ala Tyr Asp Ile Phe Ser His Phe Glu Glu Asn Tyr Asn Glu
            115                 120                 125

Val Thr Ile Gly Ser Arg Leu Thr Leu Ile Glu Asp Leu Pro Asn Ile
        130                 135                 140

Ser Ser Lys Pro Val Asp Glu Ile Ala Ser Phe Leu Lys Thr Leu Phe
145                 150                 155                 160

Thr Met Leu Glu Asp Asn Ser Glu Glu Gln Asp Lys Lys Lys Arg Arg
                165                 170                 175

Asp Thr Asn Ile Ala Leu Leu Leu Met Thr Phe Leu Pro Glu Leu Lys
            180                 185                 190
```

-continued

```
Glu Ser Phe His Glu Lys Phe Gly Asp Ser Lys Ala Leu Gln Leu Ser
            195                 200                 205

Gln Val Ile Arg Phe Cys Lys Leu Lys Ala Ser Ser Asn Ser Leu Ser
210                 215                 220

Ser Val Ser Asp Thr Leu Val Ala Gln Asp Arg Arg Ser Tyr Gln Lys
225                 230                 235                 240

Lys Gly Asn Lys Gly Cys Met Ile Cys Gly Ala Asp His Arg Leu Ser
            245                 250                 255

Asn Cys Ser Leu Leu Lys Arg Arg Ile Pro Glu Ala Arg Ile Phe Lys
            260                 265                 270

Leu Tyr Pro Asn Asp Lys Thr Asn Arg Ser Ser Ala Ser Val Ala
            275                 280                 285

Ile Pro Asp Tyr Glu Thr Gln Gly Gln Thr Ala Gly Gln Ile Thr Pro
            290                 295                 300

Lys Ser Trp Leu Cys Met Leu Ser Ser Thr Val Pro Ala Thr Lys Ser
305                 310                 315                 320

Ser Asp Trp Ile Cys Asp Thr Gly Cys Thr Ser His Met Cys His Asp
            325                 330                 335

Arg Ser Met Phe Ser Ser Phe Thr Arg Ser Ser Lys Lys Asp Phe Val
            340                 345                 350

Arg Gly Val Gly Gly Ser Ile Pro Ile Met Gly Ser Gly Thr Val Asn
            355                 360                 365

Ile Gly Thr Val Gln Leu Asn Asp Val Ser Tyr Val Pro Asp Leu Pro
            370                 375                 380

Val Asn Leu Ile Ser Ile Trp Lys Leu Cys Ala Lys Ser Asn Ser Ser
385                 390                 395                 400

Val Thr Phe Thr Lys Glu Gly Val Thr Val Lys Ser Pro Asp Val
                    405                 410                 415

Ile Ser Thr Ala Gly Lys Leu Asn Asn Tyr Leu Tyr Ile Phe Asp Asp
            420                 425                 430

Leu Thr Pro Val Thr Thr Phe Ser Ser Gln Asn Tyr Phe Cys Ser Lys
            435                 440                 445

Thr Leu Asp Ser Ser Lys Met Ile Thr Ser Ala Ala Phe His Thr Val
            450                 455                 460

Ala Asp Lys Met Leu Ser Gln His Ile Ser Pro Thr Ala Leu Pro Val
465                 470                 475                 480

Lys Trp His Ala Arg Met Gly His Pro Gly Ala Asp Ile Tyr Asn Ser
                    485                 490                 495

Leu Ala Arg Thr Leu Arg Phe Pro Lys Phe Lys Thr Ala Glu Tyr Thr
            500                 505                 510

Ile Cys Pro Thr Cys Ser Leu Ala Lys Gly Ile Ile Lys Lys Gly Lys
            515                 520                 525

Val Ser Leu Lys Lys Tyr Thr Gln Pro Leu Gln Met Val Gln Ala Asp
530                 535                 540

Leu Cys Gly Gly Phe Arg Tyr Gln Glu Phe Gln Ser Asn Lys Tyr Phe
545                 550                 555                 560

Leu Thr Ile Arg Asp Ala Tyr Ser Arg Tyr Tyr Ser Val Ile His Leu
            565                 570                 575

Lys Ser Lys Ala Asp Ala Pro Ile Lys Phe Met Glu Trp Ile Asn Glu
            580                 585                 590

Thr Glu Gln Tyr Phe Ser Ser Arg Gly Gly Phe Lys Val Gly Ser Val
            595                 600                 605
```

-continued

```
Arg Thr Asp Asn Gly Thr Glu Phe Val Asn Lys Asn Leu His Ala Phe
    610                 615                 620

Phe Lys Ser Lys Gly Ile Glu His Gln Leu Thr Ile Pro Tyr His Ser
625                 630                 635                 640

Tyr Gln Asn Gly Ala Val Glu Arg Ala His Arg Thr Ile Glu Glu Arg
                645                 650                 655

Thr Arg Cys Leu Leu Ile Gly Gly Arg Val Pro Pro Ser Leu Trp Ser
            660                 665                 670

Glu Ala Val Ser Cys Ala Val Tyr Leu Ile Asn Arg Ser Pro Val Val
            675                 680                 685

Ser Lys Asn Asn Ser Ile Pro Tyr Cys Arg Trp Phe Asn Ile Pro Ala
690                 695                 700

Lys Asp Phe Gly Ile Ala His Leu Arg Ile Phe Gly Cys Thr Ala Tyr
705                 710                 715                 720

Ala Thr Leu Gln Pro Ser Leu Arg Asp Gly Lys Leu Ala Pro Thr Val
                725                 730                 735

Ile Ser Gly Val Met Val Gly Tyr Asp Ser Asn His Arg Gly Tyr Arg
            740                 745                 750

Ile Tyr His Pro Glu Thr Gly Arg Ile Phe Val Ser Ser Gln Val Arg
        755                 760                 765

Phe Asp Glu His Met Phe Pro Leu Ala Asp Thr Glu Ala Val His Val
    770                 775                 780

Ser His Asp Phe Ala Thr Ser Ala Ile Gly Gly Val Ser Lys Tyr Pro
785                 790                 795                 800

Glu Thr Gly Ser Thr Val Ser Ala Pro Lys Asn Asp Gly Ser Asp Leu
                805                 810                 815

Ala Asn Leu Pro Ile Thr Val Pro Lys Asn Val Asn Gln Pro Ala His
            820                 825                 830

Lys Pro Asn Thr Ser Asn Ile Ser Ser Asp Asp Glu Asp Ile
835                 840                 845

Ser Met Glu Ile Glu Met Glu Lys Pro Ile Pro Glu Cys Asn Gln Asp
850                 855                 860

Asn Leu Pro Asn Ser Gly Cys Pro Pro Thr Arg Ile Gln His Ser Asn
865                 870                 875                 880

Phe Glu Ser Leu Pro Thr Val Ser Thr Glu Asp Glu Thr Asn Ser Ser
                885                 890                 895

Met Glu Lys Thr Pro Glu Arg Val Pro Ala Ala Leu Thr Tyr Arg Glu
            900                 905                 910

Ile Pro Lys Ser Ser Asp Ser Glu Tyr Ile Pro Thr Cys Arg Asn Arg
        915                 920                 925

Thr Arg Arg Val Lys Arg Thr Asn Lys Lys Pro Thr Arg Ser Arg Glu
    930                 935                 940

Ile Glu Ile Tyr Asp Ile Ser Arg Pro Asn Val Ile Ser Ser Asp Asn
945                 950                 955                 960

Leu Pro Glu Val Arg Ser Ala Lys Gln Arg Lys Thr Val Ser Asn Thr
                965                 970                 975

Asn Asp Thr Val Ala Arg Thr Asn Arg Leu Pro Thr Val Leu Arg Thr
            980                 985                 990

Leu Asp Ser Asn Asn Ile Asp Thr Leu His Val Ala Ser Thr Gly Glu
        995                 1000                1005

Glu Val Ser Ile Glu Arg Leu Ser Ser Met Ala Leu Gln Glu Ala Lys
    1010                1015                1020

Asn Asn Ser Ala Arg Thr Asn Gln Ala Asn Ser Leu Thr Asp Trp Phe
1025                1030                1035                1040
```

Pro Val Gly Ala Met Pro Ile Pro Asp Gln Arg Tyr Leu Ser Val His
            1045                1050                1055

Asp Gly Thr Tyr Ile Ser Asp Ser Gln Asp Val Gly Asp Thr Asp Leu
            1060                1065                1070

Thr Pro Ala Val Thr Arg Leu Val Thr Glu Glu Asn Ser Ile Glu Ser
            1075                1080                1085

Pro Pro Ser Leu Asp Ser Ser Pro Pro Asn Thr Ser Phe Asn Ala Ala
            1090                1095                1100

Leu Thr Ala Ile Ile His Ser Thr Lys Lys Gly Asn Pro Lys Thr Tyr
1105                1110                1115                1120

Ala Gln Ala Met Gly Arg Pro Asp Phe Gln Glu Trp His Asn Ala Cys
            1125                1130                1135

Leu Lys Glu Leu Ser Ala Phe Lys Asp His Asn Thr Tyr Lys Leu Val
            1140                1145                1150

Ser Leu Pro Lys Gln Arg Arg Ala Leu Gly Ser Arg Trp Val Phe Thr
            1155                1160                1165

Ile Lys Asp Ser Gly Thr Tyr Lys Ala Arg Leu Val Ala Gln Gly His
1170                1175                1180

Thr Gln Lys Ala Gly Ile Asp Tyr Gln Glu Thr Phe Ala Pro Val Ile
1185                1190                1195                1200

Arg Tyr Asp Ser Val Arg Leu Phe Leu Ala Leu Ala Ser Cys Leu Lys
            1205                1210                1215

Leu Ile Val Tyr Gln Met Asp Val Asp Thr Ala Phe Leu Asn Ser Lys
            1220                1225                1230

Met Asn Glu Pro Val Tyr Val Lys Gln Pro Pro Gly Phe Ile Asn Glu
            1235                1240                1245

Ser Asn Pro Asp Tyr Val Trp Glu Leu Tyr Gly Gly Met Tyr Gly Leu
            1250                1255                1260

Lys Gln Ala Pro Leu Leu Trp Asn Glu His Ile Asn Asn Thr Leu Gln
1265                1270                1275                1280

Lys Ile Gly Phe Arg Arg His Glu Gly Glu His Gly Leu Tyr Phe Arg
            1285                1290                1295

Ser Thr Ser Asp Gly Pro Ile Tyr Ile Ala Leu Tyr Val Asp Asp Leu
            1300                1305                1310

Leu Val Ala Ala Pro Ser Pro Lys Ile Tyr Asp Arg Val Lys Gln Lys
            1315                1320                1325

Leu Thr Lys Leu Tyr Ser Met Lys Asp Leu Gly Lys Val Asp Lys Phe
            1330                1335                1340

Leu Gly Leu Asn Ile Asn Gln Phe Ser Asn Gly Asp Ile Thr Leu Ser
1345                1350                1355                1360

Leu Gln Asp Tyr Ile Ala Lys Ala Ala Ser Glu Ser Glu Ile Asn Ile
            1365                1370                1375

Cys Lys Pro Thr Gln Thr Pro Leu Cys Asp Ser Lys Pro Leu Phe Glu
            1380                1385                1390

Thr Thr Ser Pro His Leu Lys Asp Ile Thr Pro Tyr Gln Ser Ile Val
            1395                1400                1405

Gly Gln Leu Leu Phe Cys Ala Asn Thr Gly Arg Pro Asp Ile Ser Tyr
            1410                1415                1420

Pro Val Ser Leu Leu Ser Arg Phe Leu Arg Glu Pro Arg Ala Ile His
1425                1430                1435                1440

Leu Glu Ser Ala Arg Arg Val Leu Arg Tyr Leu Tyr Thr Thr Arg Ser
            1445                1450                1455

Met Cys Leu Lys Tyr Arg Ser Gly Ser Leu Leu Ala Leu Thr Val Tyr
        1460                1465                1470

Cys Asp Ala Ser His Gly Ala Ile His Asp Leu Pro His Ser Thr Gly
        1475                1480                1485

Gly Tyr Val Thr Leu Leu Ala Gly Ala Pro Val Thr Trp Ser Ser Lys
        1490                1495                1500

Lys Leu Lys Gly Val Ile Pro Val Ser Ser Thr Glu Ala Glu Tyr Ile
1505                1510                1515                1520

Thr Ala Ser Glu Thr Val Met Glu Ile Glu Trp Ile Gln Asn Leu Phe
            1525                1530                1535

Glu His Leu Gly Gln Pro Leu Ile Ser Ser Thr Leu Tyr Val Asp Asn
        1540                1545                1550

Glu Pro Ala Ile Lys Leu Ser Lys His Pro Val Phe His Thr Arg Thr
        1555                1560                1565

Lys His Ile Ala Leu Arg Tyr His Lys Leu Arg Ser Ala Val Ala Ala
        1570                1575                1580

Gly Ile Ile Thr Ile Glu His Val Ile Thr Lys Arg Gln Val Ala Asp
1585                1590                1595                1600

Ile Phe Thr Lys Ile Leu Pro Ala Glu Ser Phe Lys Ala His Arg Ala
            1605                1610                1615

Val Met Val Arg Glu Pro Glu Thr Ala Lys
            1620                1625

(2) INFORMATION FOR SEQ ID NO:3:

(i) SEQUENCE CHARACTERISTICS:
        (A) LENGTH: 21 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:3:

TCTCGAGCCC CATTATCTTA GC                                      22

(2) INFORMATION FOR SEQ ID NO:4:

(i) SEQUENCE CHARACTERISTICS:
        (A) LENGTH: 22 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:4:

CGTCGACTCA TCCTATGGTT GTT                                     23

(2) INFORMATION FOR SEQ ID NO:5:

(i) SEQUENCE CHARACTERISTICS:
        (A) LENGTH: 14 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:5:

GGGTAATGTT TCAGT                                                        15

(2) INFORMATION FOR SEQ ID NO:6:

(i) SEQUENCE CHARACTERISTICS:
            (A) LENGTH:  16 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:6:

CGGTACCTAT ATACCAC                                                      17

(2) INFORMATION FOR SEQ ID NO:7:

(i) SEQUENCE CHARACTERISTICS:
            (A) LENGTH:  23 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:7:

GAGATCTGTT ATTTTGCAGT TTCT                                              24

(2) INFORMATION FOR SEQ ID NO:8:

(i) SEQUENCE CHARACTERISTICS:
            (A) LENGTH:  21 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:8:

CAGATCTCAT GCGTATTCAG TT                                                22

(2) INFORMATION FOR SEQ ID NO:9:

(i) SEQUENCE CHARACTERISTICS:
            (A) LENGTH:  24 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:9:

TGGATCCTGT TGACGTAGTG AATTA                                             25

(2) INFORMATION FOR SEQ ID NO:10:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:10:

CATTACCCAT ATCATGCT         18

(2) INFORMATION FOR SEQ ID NO:11:

(i) SEQUENCE CHARACTERISTICS:
        (A) LENGTH: 19 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:11:

TGGTAGAAGC AGTAGTAACT         20

(2) INFORMATION FOR SEQ ID NO:12:

(i) SEQUENCE CHARACTERISTICS:
        (A) LENGTH: 19 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:12:

ACCAGAGAGT GTAACAACAG         20

(2) INFORMATION FOR SEQ ID NO:13:

(i) SEQUENCE CHARACTERISTICS:
        (A) LENGTH: 19 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:13:

CTGTGTACAA GAGTAGTACC         20

(2) INFORMATION FOR SEQ ID NO:14:

(i) SEQUENCE CHARACTERISTICS:
        (A) LENGTH: 18 amino acids
        (B) TYPE: nucleic acid
        (C) STRANDEDNESS: single
        (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:14:

CACGAGCTCA TCTAGAGCC                                                  19

(2) INFORMATION FOR SEQ ID NO:15:

(i) SEQUENCE CHARACTERISTICS:
            (A) LENGTH:  18 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:15:

TGCTGAAGTA CGTGGTGAC                                                  19

(2) INFORMATION FOR SEQ ID NO:16:

(i) SEQUENCE CHARACTERISTICS:
            (A) LENGTH:  17 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:16:

AGCCCTATTC GCGTCGTG                                                   18

(2) INFORMATION FOR SEQ ID NO:17:

(i) SEQUENCE CHARACTERISTICS:
            (A) LENGTH:  19 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:17:

TACTGTCGGA TCGGAGGTTT                                                 20

(2) INFORMATION FOR SEQ ID NO:18:

(i) SEQUENCE CHARACTERISTICS:
            (A) LENGTH:  19 amino acids
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:18:

GCCTCTCCTT CTAAGAAGAT                                                 20

(2) INFORMATION FOR SEQ ID NO:19:

(i) SEQUENCE CHARACTERISTICS:
        (A) LENGTH:  19 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:19:

TTCTCGAAGT AAGCATCAAC                                        20

(2) INFORMATION FOR SEQ ID NO:20:

(i) SEQUENCE CHARACTERISTICS:
        (A) LENGTH:  27 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:20:

TAGAATATTT TTATGTTTAG STGAKTTT                                28

(2) INFORMATION FOR SEQ ID NO:21:

(i) SEQUENCE CHARACTERISTICS:
        (A) LENGTH:  27 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:21:

AAAMTCASCT AAACATAAAA ATATTCTA                                28

(2) INFORMATION FOR SEQ ID NO:22:

(i) SEQUENCE CHARACTERISTICS:
        (A) LENGTH:  29 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:22:

CCCTCGAGCA TTTACATAAC ATATAGAAAG                              30

(2) INFORMATION FOR SEQ ID NO:23:

(i) SEQUENCE CHARACTERISTICS:
        (A) LENGTH:  19 amino acids
        (B) TYPE: nucleic acid
        (C) STRANDEDNESS: single (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:23:

CCTTGTCTAA AACATTACTG                                           20

(2) INFORMATION FOR SEQ ID NO:24:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:24:

TAGTAAGTTT ATTGGACC                                             18

(2) INFORMATION FOR SEQ ID NO:25:

(i) SEQUENCE CHARACTERISTICS:
        (A) LENGTH: 19 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:25:

AGGGCTCATA ACCTGTTGAC                                           20

(2) INFORMATION FOR SEQ ID NO:26:

(i) SEQUENCE CHARACTERISTICS:
        (A) LENGTH: 21 amino acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:26:

CCTTCGAGCA GCAAACCTCC GA                                        22

(2) INFORMATION FOR SEQ ID NO:27:

(i) SEQUENCE CHARACTERISTICS:
        (A) LENGTH: 12 amino acids
        (B) TYPE: nucleic acid
        (C) STRANDEDNESS: single
        (D) TOPOLOGY: Not Relevant (ii) MOLECULE TYPE: tRNA (iii) HYPOTHETICAL: NO (xi) SEQUENCE DESCRIPTION: SEQ ID NO:27:

```
CCAAUACUCG GGA                                                      13

(2) INFORMATION FOR SEQ ID NO:28:

(i) SEQUENCE CHARACTERISTICS:
        (A) LENGTH:  12 amino acids
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:28:

GGTTATGAGC CCT                                                      13

(2) INFORMATION FOR SEQ ID NO:29:

(i) SEQUENCE CHARACTERISTICS:
        (A) LENGTH:  11 amino acids
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:29:

GGTTATGAGC CC                                                       12

(2) INFORMATION FOR SEQ ID NO:30:

(i) SEQUENCE CHARACTERISTICS:
        (A) LENGTH:  13 amino acids
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:30:

GGTTATGGGC CCAG                                                     14

(2) INFORMATION FOR SEQ ID NO:31:

(i) SEQUENCE CHARACTERISTICS:
        (A) LENGTH:  11 amino acids
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:31:

GGTTATGGGC CC                                                       12

(2) INFORMATION FOR SEQ ID NO:32:

(i) SEQUENCE CHARACTERISTICS:
        (A) LENGTH: 13 amino acids
        (B) TYPE: amino acid
        (C) STRANDEDNESS: single
        (D) TOPOLOGY: Not Relevant (ii) MOLECULE TYPE: protein
```

(iii) HYPOTHETICAL: YES (xi) SEQUENCE DESCRIPTION: SEQ ID NO:32:

```
Cys Met Ile Cys Gly Ala Asp His Arg Leu Ser Asn Cys
1               5                   10
```

(2) INFORMATION FOR SEQ ID NO:33:

(i) SEQUENCE CHARACTERISTICS:
        (A) LENGTH: 14 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:33:

```
Cys Trp Tyr Cys Lys Lys Glu Gly His Val Lys Lys Asp Cys
1               5                   10
```

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:34:

```
Cys His His Cys Gly Arg Glu Gly His Ile Lys Lys Asp Cys
1               5                   10
```

(2) INFORMATION FOR SEQ ID NO:35:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:35:

```
Trp Ile Cys Asp Thr Gly Cys Thr Ser His Met
1               5                   10
```

(2) INFORMATION FOR SEQ ID NO:36:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:36:

```
Leu Leu Leu Asp Ser Gly Ala Ser Arg Thr Leu
1               5                   10
```

(2) INFORMATION FOR SEQ ID NO:37:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:37:

Trp Val Leu Asp Ser Gly Cys Thr Ser His Met
1            5                    10

(2) INFORMATION FOR SEQ ID NO:38:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: protein (iii) HYPOTHETICAL: YES (xi) SEQUENCE DESCRIPTION: SEQ ID NO:38:

Phe Val Leu Asp Ser Gly Ala Ser Asp His Leu
1            5                    10

(2) INFORMATION FOR SEQ ID NO:39:

(i) SEQUENCE CHARACTERISTICS:
        (A) LENGTH: 138 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..137
        (D) OTHER INFORMATION: /note= "Xaa residues are not
            specified in this sequence."

(xi) SEQUENCE DESCRIPTION: SEQ ID NO:39:

Pro Leu Gln Met Val Gln Ala Asp Leu Cys Gly Xaa Xaa Xaa Xaa Xaa
1            5                    10                  15

Xaa Xaa Xaa Xaa Xaa Xaa Xaa Xaa Xaa Xaa Xaa Xaa Xaa Xaa Xaa
        20                    25                    30

Xaa Xaa Xaa Xaa Xaa Xaa Xaa Xaa Xaa Xaa Xaa Xaa Xaa Xaa Xaa
        35                    40                    45

Xaa Xaa Xaa Xaa Xaa Xaa Xaa Xaa Xaa Xaa Xaa Xaa Xaa Xaa Xaa
        50                    55                    60

Xaa Xaa Xaa Xaa Xaa Xaa Xaa Xaa Xaa Xaa Asp Asn Gly Thr Glu Phe
65                  70                    75                    80

Val Asn Lys Asn Leu His Ala Phe Phe Lys Ser Lys Gly Ile Xaa Xaa
                85                    90                    95

Xaa Xaa Xaa Xaa Xaa Xaa Xaa Xaa Xaa Xaa Asn Gly Ala Val Glu Arg
            100                    105                  110

Ala His Arg Thr Ile Glu Glu Arg Thr Arg Xaa Xaa Xaa Xaa Xaa Xaa
            115                    120                  125

```
Xaa Xaa Xaa Xaa Xaa Xaa Trp Ser Glu Ala
    130                 135

(2) INFORMATION FOR SEQ ID NO:40:

(i) SEQUENCE CHARACTERISTICS:
        (A) LENGTH: 137 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..136
        (D) OTHER INFORMATION: /note= "Xaa residues are not
            specified in this sequence."

(xi) SEQUENCE DESCRIPTION: SEQ ID NO:40:

Pro Pro Gln Tyr Leu His Thr Asp Ile Phe Gly Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Asp Arg Gly Ser Glu Tyr
65                  70                  75                  80

Thr Asn Arg Leu His Lys Phe Leu Glu Lys Asn Gly Ile Xaa Xaa Xaa
                85                  90                  95

Xaa Xaa Xaa Xaa Xaa Xaa Xaa Xaa Xaa His Gly Val Ala Glu Arg Leu
            100                 105                 110

Asn Arg Thr Leu Leu Asp Asp Cys Arg Xaa Xaa Xaa Xaa Xaa Xaa
        115                 120                 125

Xaa Xaa Xaa Xaa Xaa Trp Phe Ser Ala
    130                 135

(2) INFORMATION FOR SEQ ID NO:41:

(i) SEQUENCE CHARACTERISTICS:
        (A) LENGTH: 135 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..135
        (D) OTHER INFORMATION: /note= "Xaa residues are not
            specified in this sequence."

(xi) SEQUENCE DESCRIPTION: SEQ ID NO:41:

Val Leu Arg Tyr Val His Ala Asp Leu Trp Gly Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Asp Asn Gly Leu Glu Phe Cys Asn Leu
65                  70                  75                  80

Lys Phe Asp Ala Tyr Cys Lys Glu His Gly Ile Xaa Xaa Xaa Xaa Xaa
                85                  90                  95

Xaa Xaa Xaa Xaa Xaa Xaa Xaa Asn Gly Val Ala Glu Arg Met Asn Arg
            100                 105                 110

Thr Ile Met Glu Lys Val Arg Xaa Xaa Xaa Xaa Xaa Xaa Xaa Xaa
            115                 120                 125

Xaa Xaa Xaa Trp Ala Glu Ala
130                 135

(2) INFORMATION FOR SEQ ID NO:42:

(i) SEQUENCE CHARACTERISTICS:
        (A) LENGTH: 134 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..134
        (D) OTHER INFORMATION: /note= "Xaa residues are not
            specified in this sequence."

(xi) SEQUENCE DESCRIPTION: SEQ ID NO:42:

Pro Leu Phe Val Val His Ser Asp Val Cys Gly Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Asp Asn Gly Arg Glu Tyr Leu Ser Asn Glu
65                  70                  75                  80

Met Arg Gln Phe Cys Val Lys Lys Gly Ile Xaa Xaa Xaa Xaa Xaa
                85                  90                  95

Xaa Xaa Xaa Xaa Xaa Xaa Asn Gly Val Ser Glu Arg Met Ile Arg Thr
            100                 105                 110

Ile Thr Glu Lys Ala Arg Xaa Xaa Xaa Xaa Xaa Xaa Xaa Xaa Xaa
            115                 120                 125

Xaa Xaa Trp Gly Glu Ala
130

(2) INFORMATION FOR SEQ ID NO:43:

(i) SEQUENCE CHARACTERISTICS:
        (A) LENGTH: 137 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
            (A) NAME/KEY: Region
            (B) LOCATION: 1..130
            (D) OTHER INFORMATION: /note= "Xaa residues are not
                specified in this sequence."

(xi) SEQUENCE DESCRIPTION: SEQ ID NO:43:

Lys Ala Arg Leu Val Ala Gln Gly His Thr Gln Lys Ala Gly Ile Asp
1               5                   10                  15

Tyr Gln Glu Thr Phe Ala Pro Val Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Gln Met Asp
        35                  40                  45

Val Asp Thr Ala Phe Leu Asn Ser Lys Met Asn Glu Pro Val Tyr Val
    50                  55                  60

Lys Gln Pro Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                      95

Xaa Xaa Xaa Xaa Xaa Xaa Xaa Xaa Xaa Xaa Xaa Xaa Xaa Xaa Xaa
            100                 105                     110

Xaa Xaa Xaa Xaa Xaa Xaa Xaa Xaa Xaa Xaa Xaa Xaa Xaa Xaa Xaa
        115                 120                 125

Tyr Ile Ala Leu Tyr Val Asp Asp Leu
    130                 135

(2) INFORMATION FOR SEQ ID NO:44:

(i) SEQUENCE CHARACTERISTICS:
            (A) LENGTH: 130 amino acids
            (B) TYPE: amino acid
            (C) STRANDEDNESS: Not Relevant
            (D) TOPOLOGY: Not Relevant (ii) MOLECULE TYPE: protein (iii) HYPOTHETICAL: YES (ix) FEATURE:
            (A) NAME/KEY: Region
            (B) LOCATION: 1..128
            (D) OTHER INFORMATION: /note= "Xaa residues are not
                specified in this sequence."

(xi) SEQUENCE DESCRIPTION: SEQ ID NO:44:

Lys Ala Arg Phe Val Ala Arg Gly Asp Ile Gln His Pro Asp Thr Tyr
1               5                   10                  15

Asp Ser Gly Met Gln Ser Asn Thr Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Gln Leu Asp
        35                  40                  45

Ile Ser Ser Ala Tyr Leu Tyr Ala Asp Ile Lys Glu Glu Leu Tyr Ile
    50                  55                  60

Arg Pro Pro Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                      95

Xaa Xaa Xaa Xaa Xaa Xaa Xaa Xaa Xaa Xaa Xaa Xaa Xaa Xaa Xaa
            100                 105                     110

```
Xaa Xaa Xaa Xaa Xaa Xaa Xaa Xaa Xaa Xaa Thr Ile Cys Leu Phe Asp
            115                 120                 125

Asp Met
    130
```

(2) INFORMATION FOR SEQ ID NO:45:

(i) SEQUENCE CHARACTERISTICS:
        (A) LENGTH: 138 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..130
        (D) OTHER INFORMATION: /note= "Xaa residues are not
            specified in this sequence."

(xi) SEQUENCE DESCRIPTION: SEQ ID NO:45:

```
Lys Ala Gln Leu Val Ala Lys Gly Tyr Thr His Arg Glu Gly Val Asp
1               5                   10                  15

Tyr Gln Glu Ile Phe Ala Leu Val Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Gln Met Asp
            35                  40                  45

Val Lys Thr Ala Phe Leu His Gly Glu Leu Glu Glu Glu Leu Tyr Met
50                  55                  60

Glu Gln Pro Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Tyr Leu Leu Leu Tyr Val Asp Asp Met
            130                 135
```

(2) INFORMATION FOR SEQ ID NO:46:

(i) SEQUENCE CHARACTERISTICS:
        (A) LENGTH: 137 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (ix) FEATURE:
        (A) NAME/KEY: Region
        (B) LOCATION: 1..137
        (D) OTHER INFORMATION: /note= "Xaa residues are not
            specified in this sequence."

(xi) SEQUENCE DESCRIPTION: SEQ ID NO:46:

```
Lys Ala Arg Leu Val Ala Arg Gly Phe Thr Gln Lys Tyr Gln Ile Asp
1               5                   10                  15

Tyr Glu Glu Thr Phe Ala Pro Val Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Gln Met Asp
        35                  40                  45

Val Lys Thr Ala Phe Leu Asn Gly Thr Leu Lys Glu Glu Ile Tyr Met
 50                  55                  60

Arg Leu Pro Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
        115                 120                 125

Tyr Val Leu Leu Tyr Val Asp Asp Val
        130                 135

(2) INFORMATION FOR SEQ ID NO:47:

(i) SEQUENCE CHARACTERISTICS:
        (A) LENGTH: 94 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..94
        (D) OTHER INFORMATION: /note= "Xaa residues are not
            specified in this sequence."

(xi) SEQUENCE DESCRIPTION: SEQ ID NO:47:

Ser Ser Thr Glu Ala Glu Tyr Ile Thr Ala Ser Glu Thr Val Met Glu
 1               5                  10                  15

Ile Glu Trp Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Ile Lys Leu Ser Lys
        35                  40                  45

His Pro Val Phe His Thr Arg Thr Lys His Ile Ala Leu Arg Tyr His
 50                  55                  60

Lys Xaa Xaa Xaa Xaa Xaa Xaa Xaa Xaa Xaa Xaa Xaa Xaa Xaa Xaa Xaa
 65                  70                  75                  80

Xaa Thr Lys Arg Gln Val Ala Asp Ile Phe Thr Lys Ile Leu
                85                  90

(2) INFORMATION FOR SEQ ID NO:48:

(i) SEQUENCE CHARACTERISTICS:
        (A) LENGTH: 190 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: YES (ix) FEATURE:
        (A) NAME/KEY: Region
        (B) LOCATION: 1..90
        (D) OTHER INFORMATION: /note= "Xaa residues are not
            specified in this sequence."
```

(xi) SEQUENCE DESCRIPTION: SEQ ID NO:48:

```
Ser Thr Thr Glu Ala Glu Ile His Ala Ile Ser Glu Ser Val Pro Leu
1               5                   10                  15

Leu Met Asn Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Ile Ser Ile Ile Lys
        35                  40                  45

Ser Thr Asn Glu Glu Lys Phe Arg Asn Arg Phe Phe Gly Thr Lys Ala
50                  55                  60

Met Arg Xaa Xaa Xaa Xaa Xaa Xaa Xaa Xaa Xaa Xaa Xaa Xaa Xaa Xaa
65                  70                  75                  80

Xaa Xaa Thr Lys Lys Asn Ile Ala Asp Val Met Thr Lys Pro Leu Ser
            85                  90                  95

Thr Thr Glu Ala Glu Ile His Ala Ile Ser Glu Ser Val Pro Leu Leu
            100                 105                 110

Met Asn Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Ile Ser Ile Ile Lys Ser
        130                 135                 140

Thr Asn Glu Glu Lys Phe Arg Asn Arg Phe Phe Gly Thr Lys Ala Met
145                 150                 155                 160

Arg Xaa Xaa Xaa Xaa Xaa Xaa Xaa Xaa Xaa Xaa Xaa Xaa Xaa Xaa Xaa
            165                 170                 175

Xaa Thr Lys Lys Asn Ile Ala Asp Val Met Thr Lys Pro Leu
            180                 185                 190
```

(2) INFORMATION FOR SEQ ID NO:49:

(i) SEQUENCE CHARACTERISTICS:
        (A) LENGTH: 94 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: YES (ix) FEATURE:
        (A) NAME/KEY: Region
        (B) LOCATION: 1..94
        (D) OTHER INFORMATION: /note= "Xaa residues are not
        specified in this sequence."

(xi) SEQUENCE DESCRIPTION: SEQ ID NO:49:

```
Ser Thr Thr Glu Ala Glu Phe Met Ala Leu Thr Glu Ala Ala Lys Glu
1               5                   10                  15

Ala Leu Trp Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Ile Cys Leu Phe Lys
        35                  40                  45

Asn Ser Thr His His Glu Arg Thr Lys His Ile Asp Val Arg Tyr Asn
50                  55                  60

Phe Xaa Xaa Xaa Xaa Xaa Xaa Xaa Xaa Xaa Xaa Xaa Xaa Xaa Xaa Xaa
65                  70                  75                  80

Xaa Thr Ser Arg Asn Pro Ala Asp Ala Leu Thr Lys Ser Ile
            85                  90
```

(2) INFORMATION FOR SEQ ID NO:50:

```
        (i) SEQUENCE CHARACTERISTICS:
            (A) LENGTH: 95 amino acids
            (B) TYPE: amino acid
            (C) STRANDEDNESS: Not Relevant
            (D) TOPOLOGY: Not Relevant (ii) MOLECULE TYPE: protein (iii) HYPOTHETICAL: YES (ix) FEATURE:
            (A) NAME/KEY: Region
            (B) LOCATION: 1..95
            (D) OTHER INFORMATION: /note= "Xaa residues are not
                specified in this sequence."

(xi) SEQUENCE DESCRIPTION: SEQ ID NO:50:

Ser Ser Thr Glu Ala Glu Tyr Met Ala Leu Phe Glu Ala Val Arg Glu
 1               5                  10                  15

Ala Leu Trp Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Ile Ser Ile Ala
         35                  40                  45

Asn His Pro Ser Cys His Lys Arg Ala Lys His Ile Asp Ile Lys Tyr
     50                  55                  60

His Phe Xaa Xaa Xaa Xaa Xaa Xaa Xaa Xaa Xaa Xaa Xaa Xaa Xaa
65                   70                  75                  80

Xaa Xaa Thr Glu Asn Gln Leu Ala Asp Ile Phe Thr Lys Pro Leu
             85                  90                  95

(2) INFORMATION FOR SEQ ID NO:51:

(i) SEQUENCE CHARACTERISTICS:
            (A) LENGTH: 12 base pairs
            (B) TYPE: nucleic acid
            (C) STRANDEDNESS: double
            (D) TOPOLOGY: Not Relevant (ii) MOLECULE TYPE: DNA (genomic)

(iii) HYPOTHETICAL: NO (xi) SEQUENCE DESCRIPTION: SEQ ID NO:51:

ACCCATTCAT AA                                                              12
```

RETROTRANSPOSON AND METHODS

CROSS-REFERENCE TO RELATED APPLICATIONS

This application takes priority from U.S. Provisional Patent Application No. 60/010,869, filed Jan. 31, 1996.

ACKNOWLEDGEMENT OF FEDERAL RESEARCH SUPPORT

This invention was made, at least in part, with funding from the United States Department of Agriculture (Project No. IOW 03120). The United States Government may thus have certain rights in this invention.

BACKGROUND OF THE INVENTION

The field of this invention is molecular biology, particularly in the area of retrotransposons, nucleotide sequence encoding integrase therefrom, and molecular genetic methods based thereon.

Mobile genetic elements that replicate by reverse transcription are ubiquitous among eukaryotic genomes. These elements, collectively called retroelements, include the retroviruses and two classes of retrotransposons, which are distinguished by whether or not they are flanked by long terminal direct repeats (LTRs) (Xiong and Eickbush 1990). A common step in retroelement replication involves the integration of an element cDNA into the host genome (Brown and Varmus 1989). For the retroviruses and LTR retrotransposons, this step is carried out by a nucleoprotein complex called the integration complex. A key component of the integration complex is the element-encoded integrase protein, which carries out the cutting and joining steps of the integration reaction. Although, in general, no specific sequences are required at the target site for integration, the distribution of LTR retroelements is clearly non-random (Craigie 1992; Sandmeyer et al. 1990).

Examples of retroelement target specificity are provided by the retrotransposons of *Saccharomyces cerevisiae*. *S. cerevisiae* has five distinct retrotransposon families, designated Ty1–Ty5, which vary extensively in copy number (from 25–30 Ty1/Ty2 insertions to zero to two Ty5 insertions per haploid genome) (Boeke and Sandmeyer 1991; Zou et al. 1995). A distinctly non-random distribution of Ty1–Ty4 insertions has been revealed from the nucleotide sequences of several *S. cerevisiae* chromosomes (e.g. chromosome (chr) III (Ji et al. 1993; Oliver et al. 1992)). Most native Ty1–Ty4 elements are found within 1 kb upstream of genes transcribed by RNA polymerase III (pol III), such as tRNA genes. For Ty1 and Ty3, this genomic organization is the consequence of targeted integration; pol III genes are the preferred targets of de novo Ty1 and Ty3 transposition events Chalker and Sandmeyer 1990; Chalker and Sandmeyer 1992; Ji et al. 1993; Devine and Boeke 1996).

Mechanisms that dictate Ty target specificity have been studied in detail for Ty3. Ty3 integration is highly precise, and typically occurs within the first few base-pairs of the start site of pol III gene transcription (Chalker and Sandmeyer 1992). For tRNA genes, mutations in the promoter that abolish transcription also abolish targeted transposition. Biochemical analyses, including in vitro transposition assays, have demonstrated that the pol III transcription factors TFIIIB and TFIIIC are sufficient for targeted integration (Kirchner et al. 1995). Current models suggest that these transcription factors tether the Ty3 integration complex to its target through protein—protein interactions.

Integration sites for several retroviruses tend to be associated with DNase I hypersensitive sites, suggesting retroviruses prefer open chromatin (Craigie 1992; Sandmeyer et al. 1990). The yeast two-hybrid system has recently been used to identify a human protein, Ini1, that specifically interacts with HIV integrase (Kalpana et al. 1994). Ini1 is a homologue of the yeast transcription factor SNF5, which is known to remodel chromatin in yeast to promote transcription. The HIV integrase/Ini1 interaction suggests that retroelements may, in general, recognize specific DNA-bound protein complexes to choose their integration sites.

In striking contrast to the Ty1–Ty4 families, endogenous Ty5 insertions are located in sub-telomeric regions or on chr III adjacent to the silent mating locus HMR (Zou et al. 1995). However, none of the Ty5-related insertions in the *S. cerevisiae* genome characterized to date are full-length, functional transposable elements. Most characterized Ty5-related insertions in *S. paradoxus* are incomplete and non-functional as well.

The telomeres and the transcriptional silencers flanking HMR direct the assembly of a distinct type of chromatin (silent chromatin) that represses the transcription of adjacent genes (Laurenson and Rine 1992). Silent chromatin is also assembled at HML, a second mating locus on chr III, and transcriptional repression of both HML and HMR prevents the expression of mating type information unless it is copied to MAT, a third, transcriptionally active mating locus. A number of proteins contribute to silent chromatin structure and transcriptional repression at the telomeres and silent mating loci. Among these are proteins involved in DNA replication (the origin recognition complex (ORC); (Bell et al. 1993; Foss et al. 1993; Micklem et al. 1993)), transcription factors (RAPPolII1 and ABF1; (Diffley and Stillman 1988; Kurtz and Shore 1991), histones (H3 and H4; (Kayne et al. 1988; Thompson et al. 1994)), components of acetyltransferases (NAT1 and ARD1; (Mullen et al. 1989) and several proteins that have a specific role in silencing (SIR1–SIR4 and RIF1; Rine and Herskowitz 1987; Hardy et al. 1992)). Chromatin at the telomeres and silent mating loci is analogous to heterochromatin in other eukaryotes (Hecht et al. 1995). In *Drosophila melanogaster*, a number of transposable elements are associated with heterochromatin (Pimpinelli et al. 1995), including DNA transposons such as the P elements, which preferentially transpose to some heterochromatic sites (Karpen and Spradling 1992). Surprisingly, some heterochromatic transposable elements have evolved apparently essential roles for the cell; the HeT and TART retroelements can serve as *D. melanogaster* telomeres (Biessmann et al. 1990; Levis et al. 1993).

The present disclosure provides the isolation of a transpositionally active Ty5 element from the yeast, *Saccharomyces paradoxus* and a Ty5 transposition assay which can be carried out in *S. cerevisiae*, as well as other applications based on Ty5 and derivatives thereof.

BRIEF DESCRIPTION OF THE DRAWINGS

FIGS. 1A–1C provide sequence analysis of *S. paradoxus* Ty5 retrotransposons. FIG. 1A illustrates a comparison of the structural organization of the *S. cerevisiae* Ty5-1 element and the *S. paradoxus* Ty5-5p and Ty5-6p elements. Open boxes with arrowheads indicate long terminal direct repeats (LTRs). Arrows over the internal domain indicate open reading frames and arrowheads denote stop codons. Shaded boxes depict conserved amino acid sequence domains: RB, RNA binding; PR, protease; IN, integrase; RT, reverse transcriptase; RH, RNase H. The lines designated a and b under Ty5-6p mark the probes used in FIG. 2. The percentages reflect nucleotide identity between elements. The naturally occurring deletion in Ty5-1 is noted by the dashed line, and the Ty5-1 RB domain is unrecognizable due to nucleotide changes. Bases in Ty5-5p that differ from Ty5-6p are noted below the element. FIG. 1B provides amino acid sequence alignments of domains conserved between Ty5-6p and other retrotransposons and retroviruses. The amino acid sequences of the RNA binding regions of the Ty5-6p, Ta1-2 and copia proteins are given in SEQ ID NOs: 32, 33 and 34, respectively. The amino acid sequence of the protease regions of the Ty5-6p, Ty1H3, Ta1-3 and copia proteins are given in SEQ ID NOs: 35–38. The partial integrase amino acid sequences of the Ty5-6, Ty1H3, Ta1-3 and copia are given in SEQ ID NOs: 39–42, respectively. The partial amino acid sequences of the reverse transcriptases of Ty5-6, Ty1H3, Ta1-3 and copia are given in SEQ ID NOs: 43–46. The partial amino acid sequences of the RNaseH of Ty5-6, Ty1H3, Ta1-3 and copia are given in SEQ ID NOs: 47–50. Sequences used in the alignment are from the Ty1-copia group retrotransposons, including Ty1-H3 from S. cerevisiae (M18706), Ta1-3 from *Arabidopsis thaliana* (X13291) and copia from *D. melanogaster* (M11240). Black boxes denote identical amino acids shared among at least three of the four aligned elements. Numbers indicate amino acid residues omitted from the figure. Note: Ty1 does not encode an RNA binding domain. FIG. 1C shows the Ty5 primer binding site, which is complementary to the anticodon stem-loop of *S. cerevisiae* initiator methionine tRNA. Filled circles in the tRNA indicate nucleotides that pair to primer binding sites (PBSs); open circles indicate non-paired nucleotides. Nucleotides 63–76 are complementary to the Ty1 PBS; nucleotides 69–76 are complementary to the Ty3 PBS; nucleotides 28–40 are complementary to the putative Ty5 PBS. This latter region is shown aligned to the Ty5-1 and Ty5-6p PBSs. The sequence of other retrotransposon PBSs that begin at the same nucleotide position are shown. GenBank accession numbers for these sequences are: Osser, X69552; copia, M11240; Tp2, X52770. Nucleotide differences between some PBSs may reflect sequence differences among host initiator tRNAs or element mutations. The nucleotide sequences of the *S. typhimurium* cerevisiae tRNA antistem-loop binding region is given in SEQ ID NO:27. The complementary regions of the primer binding sites of Ty5-1, T5-6p, Osser, copia and Tp2 are given in SEQ ID Nos: 28, 28, 29, 30 and 31, respectively.

FIG. 2A shows Northern analysis of Ty5 transcripts. The lane designated *S. para* shows hybridization of probe a (FIG. 1A) to 0.7 mg of poly(A) RNA isolated from logarithmic phase cultures of *S. paradoxus* strain NRRL Y17217. The 2.4 kb transcript was also observed with probe b (data not shown). The lane marked *S. cere*+gal shows hybridization of probe a to 15 mg of total RNA from *S. cerevisiae* cells carrying plasmid pSZ152 that had been grown on 2% galactose for 24 hrs. The transcript corresponds in size to the full-length Ty5-6p element, including the hisAI marker gene. Note that the intensity of hybridization does not reflect relative expression levels. FIG. 2B illustrates Primer extension analysis of RNAs described in FIG. 2A. The sequencing ladder was generated with a subclone of the Ty5-6p 5' LTR with the same primer used for primer extensions. Base positions of the major start sites of transcription are noted. FIG. 2C shows sequence features of the Ty5-6p 5' LTR. The Ty5-6p sequences shown correspond to nucleotides 1228–1767 of SEQ ID NO: 1 and amino acids 1–8 of SEQ ID NO: 2. Bases which differ from the *S. cerevisiae* Ty5-1 element are shown below the sequence. Arrows denote the terminal inverted repeats. Hooked arrows indicate the transcription start sites of Ty5 in *S. paradoxus*, and asterisks indicate start sites in *S. cerevisiae* determined using galactose-induced mRNA. Vertical arrows mark the positions of the GAL1-10 UAS fusions. The PBS is underlined, as is the ATG, which marks the beginning of the Ty5 ORF.

FIGS. 3A–3C illustrate a Ty5 transposition assay in *S. cerevisiae*. FIG. 3A shows the selection scheme for Ty5 transposition. The Ty5-5p and Ty5-6p elements were placed under the transcriptional control of the GAL1-10 UAS and further modified by insertion of a his3AI marker gene between the end of the Ty5 ORF and the beginning of the 3' LTR. In this marker, the HIS3 gene is interrupted by an artificial intron (AI) that is in the antisense orientation relative to the HIS3 message; SD, splice donor; SA, splice acceptor (Step 1). The intron, however, is in the sense orientation to be spliced from the Ty5 transcript and the HIS3 gene can be reconstituted after reverse transcription of the spliced Ty5 message (Step 2). FIG. 3B is a photograph of yeast cell patches carrying the Ty5-5p (ySZ127) and Ty5-6p (ySZ128) were grown on galactose-containing media to induce transcription and replica plated to media lacking histidine to select for the reconstituted HIS3 gene. His$^+$ cells were only observed for Ty5-6p constructs. FIG. 3C shows frequency of His$^{30}$ cells in ySZ128 carrying Ty5-6p. Cells were scraped from patches on galactose-containing media, diluted in dH$_2$O and plated on rich media (YPD) and synthetic media without histidine (SC-H). Colonies were counted after growth at 30° C., and the frequency was calculated by dividing the colony number on SC-H plates by the product of the colony number on YPD plates and the dilution factor.

FIG. 7 provides a restriction map of the Ty5-6p, with positions as nucleotide numbers.

FIG. 8 provides a map of the Ty5-6p derivative in which the promoterless kanamycin resistance determinant of Tn5 has been inserted in an orientation opposite that of the large open reading frame of the retrotransposon ORF.

FIG. 12A depicts the chromosomal locations of endogenous Ty5 elements. Chromosomes are drawn to scale with the left ends on top. The asterisk reflects elements on the Crick strand of the chromosomal sequences. Bases positions for insertions are Ty5-1, 1172-4314; Ty5-2, 290646-290891; Ty5-3, 291015-191252; Ty5-4, on chr III, 4471-4572; Ty5-4 on chr IX, 664909-664808; Ty5-7, 665062-665300; Ty5-8, 7993-8224; Ty5-15, 863-1079; Ty5-16, 562209-562459; Ty5-17, 564300-564533. FIG. 12B shows sequence rearrangements between chr III and chr XI of S. cerevisiae. Symbols are as in FIG. 11. Duplicated sequence domains are indicated by arrows and designated as a, b, or c. The Y' element in region c is labeled. The open box labeled chr III represents an additional sequence duplication between chr XI L and chr III r.

SUMMARY OF THE INVENTION

Figure 1A:
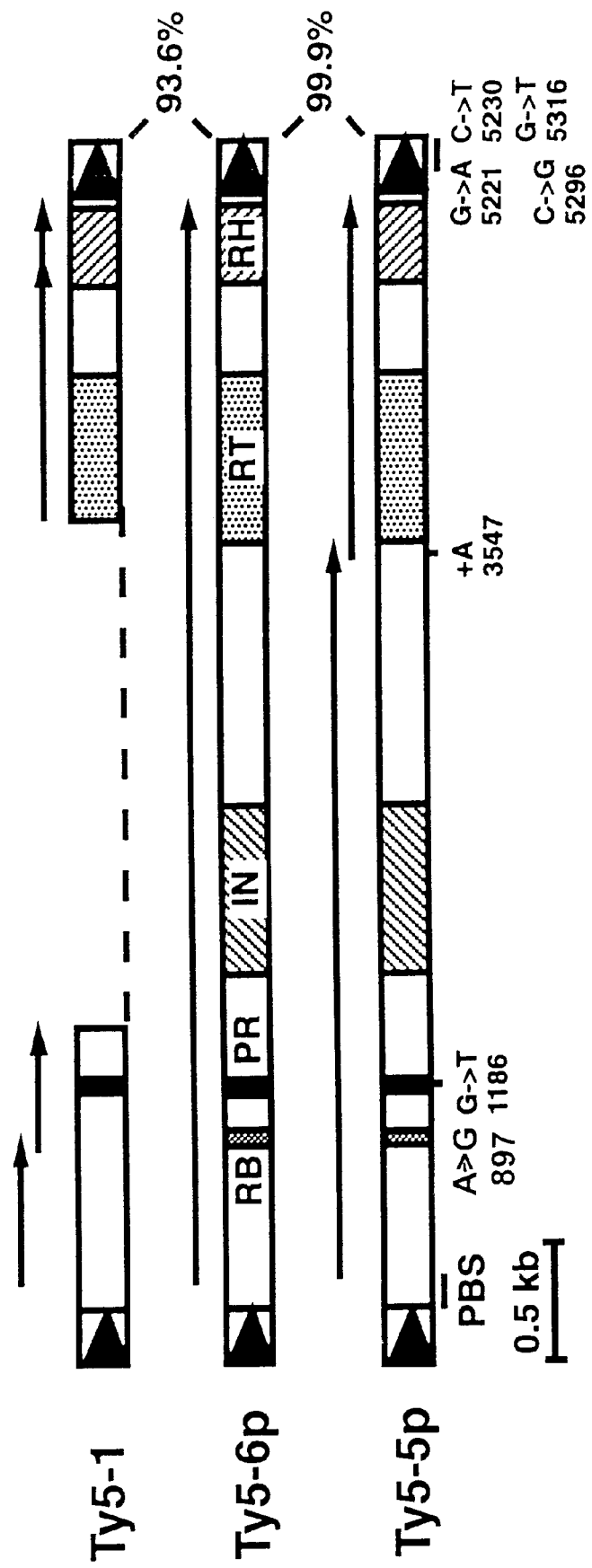

The present invention provides a retrotransposon, functional in yeast and which has the advantage of target site specificity for insertion, especially in silent and/or telomeres of the yeast genome. This retrotransposon is termed Ty5-6p herein, and the nucleotide sequence of this element as it was isolated from nature is provided in SEQ ID NO:1.

Further aspects of the present invention are the genetic engineering of Ty5-6p to incorporate heterologous DNA, and methods for the subsequent stable introduction and targeted retrotransposition of the modified Ty5-6p into the genome of a eukaryotic cell. In particular, the Ty5-6p retrotransposon exhibits significant target site specificity for heterochromatin (silent regions of the genome), including but not limited to telomeres. Ty5-6p and its derivatives can be used to genetically modify plant cells and tissue, animal cells and tissue, and as particularly preferred, yeast cells, more preferably one of Saccharomyces cerevisiae and Saccharomyces paradoxus. Once incorporated into the genome of a eukaryotic cell, this modified Ty5-6p and the heterologous DNA carried within it can serve as genetic markers, which can be silent or expressed according to the choice of promoter sequence or lack thereof. If expressed and a suitable choice of the marker has been made, the expressed genetic marker carried on a modified Ty5-6p can serve to select genetically modified strains (for example, those modified in other ways and/or at other locations in the genome). Alternatively, the modified Ty5-6p can serve as a marker of a particular origin of a particular strain of interest; for example, marked strains released into the environment could be followed by virtue of this modified element or commercially used strains could be marked to identify potential infringing or unauthorized uses thereof. Encompassed by the present invention are methods for targeting DNA sequences to silent regions (including but not limited to telomeres) of the eukaryotic genome, especially the genome of yeast cells. With appropriately modified Ty5-6p derivatives, eukaryotic cells can be genetically engineered to alter telomere structure, thus increasing or decreasing the life span of the altered cell when compared to the parental cell. Incorporation of a functional Ty5-6p element allows the complementation of a telomere defect, extending the life of a cell, such as yeast, and incorporation of an HO endonuclease recognition site within the Ty5-6p element and transposing it into a host cell expressing an HO endonuclease results in shortening of the telomere through endonuclease activity, thereby shortening the lifespan of that cell.

The targeting of Ty5-6p and its derivatives to silent chromatin and chromatin-like silent chromatin allows the identification of cellular genes involved in developmental pathways and/or senescence (aging). These genes occur in heterochromatin, with activation of the genes at specific times during the developmental pathway or a particular time in the lifetime of the cell. The insertion of Ty5-6p or a derivative thereof (e.g., carrying a selectable marker) can be identified where normal development or aging (recognized by a substantially increased or a substantially decreased lifespan, depending on the gene whose function has been disrupted) or by cloning of the Ty5-6p sequences from the modified genome and subsequent sequence analysis of the adjacent nucleotide sequences, as readily understood by one of ordinary skill in the art. As used herein, "chromatin like silent chromatin" is chromatin that directs the integration of Ty5, and this term encompasses the complex of the DNA and proteins specifically bound thereto.

A further aspect of the invention is the incorporation of a coding sequence of interest within the Ty5-6p retrotransposon so that the coding sequence is expressed under the control of a promoter which is resistant to silencing in the target organism of choice. The incorporation of the modified transposable element into otherwise silent regions of the genome allows the modification of the genome in a way which does not disrupt the normal genetic functioning of the cell or organism, and thus, with the incorporation of a therapeutically effective gene in an expressible form, the modified retrotransposon provides an alternative existing forms of gene therapy.

An additional aspect of the invention is the genetic engineering of the Ty5-6p element to contain a promoterless selectable marker (such as, for example, that of the kanamycin resistance marker of Tn5) downstream of a cloning site or polylinker so that fragments of eukaryotic chromosomal DNA could be inserted for use as a promoter probe vector where the promoters to be identified are immune to silencing when the recombinant, modified and transposed element has been incorporated into a silent DNA region or a telomere. Only the recombinant insertion of a silencing-resistant promoter would allow functional expression of the selectable marker after transposition to a silent region of DNA, including a telomeric or subtelomeric region of the genome. Encompassed within the present invention is the silencing-resistant-promoter probe Ty5-6p derivative and methods for its use.

DETAILED DESCRIPTION OF THE INVENTION

Many retrotransposon insertions are non-functional. An extensive survey of Ty5 elements among diverse S. cerevisiae strains and certain other Saccharomyces species failed to identify transposition-competent insertions (Zou et al. 1995). All were either solo LTRs or a degenerate insertion that had accumulated several deleterious mutations (Ty5-1). A survey of other yeast species, however, revealed numerous Ty5 elements in some strains of S. paradoxus, the species most closely related to S. cerevisiae. Ty5 insertions were found associated with type X sub-telomeric repeats. Copy number was estimated in S. paradoxus NRRL 17217 by Southern hybridization analysis using restriction enzymes that do not cut within the element (XhoI) or cut only once (HindIII) and probes specific to either Ty5 internal sequences or Ty5 LTRs. Based on this analysis, at least six restriction fragments hybridized to both internal and LTR sequences in NRRL Y17217. In the HindIII lanes, there are at least seven more restriction fragments that hybridized to the LTR. Some of these extra LTRs may be solo LTRS, which are derived from recombination between LTRs of full-length Ty5 elements.

Six different Ty5 elements were cloned from S. paradoxus NRRL Y-17217 using internal domain probes from Ty5-1. Preliminary sequencing and restriction mapping identified two structurally similar insertions, Ty5-5p and Ty5-6p (the p denotes their origin from S. paradoxus), which were of a size consistent with an active retroelement (4–6 kb). The complete DNA sequence was obtained for both insertions.

Five of the approximately 13 Ty5 insertions present in S. paradoxus strain NRRL Y-17217 were analyzed with respect to sequences flanking these insertions. Only the Ty5-6p insertion had target site duplications. The five bp target sequence at the 3' end of Ty5-14p is the same as the 5' target sequence of Ty5-5p, suggesting that Ty5-5p and Ty5-14p recombined and exchanged targets, and Ty5-14p subsequently suffered a deletion of its 5' region. Reciprocal translocation is consistent with sequence differences among the LTRs of these elements. The 3' LTR of Ty5-5p has four bp that differ from the 5' LM The TY5-5p 3' LTR, however, is identical at these four nucleotide positions to the 5' LTR of Ty5-14p, indicating that a recombination event had occurred between these elements.

Flanking sequences of several S. paradoxus insertions were compared to the S. cerevisiae genome database or used in Southern hybridization analysis. 5' and 3' sequences flanking Ty5-6p share about 90% nucleotide identity to sequences on S. cerevisiae chr XI. The 5' flanking sequence hybridized to chr XI of S. paradoxus and S. cerevisiae, indicating that Ty5-6p is located on S. paradoxus chr XI and its flanking sequences are conserved between the two species. No evidence for a Ty5 insertion, however, was found at the corresponding region on S. cerevisiae chr XI, suggesting Ty5-6p transposed to this site after species divergence.

Analysis of flanking sequences of some S. paradoxus insertions support a role for Ty5 in genome rearrangements. Several Ty5 elements were flanked by sequences unique to S. paradoxus. For example, the 5' flanking sequence of Ty5-5p shows no significant homology to any S. cerevisiae sequences, while the 3' flanking sequence shares high homology with the subtelomeric X repeat. Southern analysis indicated that the unique 5' flanking sequence hybridizes to S. paradoxus chr III and XI, suggesting that this sequence is duplicated between these chromosomes. Since Ty5-5p is associated with a subtelomeric X repeat, the duplication is believed to have occurred between the ends of chr III and XI. Sequence analysis of Ty5-14p indicated a 5' deletion, which includes the 5' LTR. The 3' flanking sequence has no significant similarity to any S. cerevisiae sequences. Flanking sequences of some elements suggest that Ty5 insertions mark sites that have been rearranged between S. paradoxus and S. cerevisiae. For example, the 5' sequence of Ty5-12p hybridized to S. cerevisiae chr V. This sequence, however, hybridized to S. paradoxus chr III and XI, indicating that it has been duplicated and rearranged between these species. Consistent with the hybridization analysis, the 5' flanking sequence shares 90% nucleotide identity with a subtelomeric region of S. cerevisiae chr V. The 3' sequence of Ty5-12p shares 90% identity to the middle of the left arm of S. cerevisiae chr I, providing evidence for additional rearrangements. Part of the flanking sequences of insertion Ty5-1 lp were also determined. The 5' sequence shares 84% identity with that at the subtelomeric region of S. cerevisiae chr XVI, but the 3' sequence has 84% identity to the subtelomeric region of S. cerevisiae chr XIII. Although the chromosome location of this element was not determined by hybridization analysis, these results indicate a sequence rearrangement between S. paradoxus and S. cerevisiae and implicate a role for Ty5 elements in genome rearrangements.

Ty5-6p is 5376 bp in length and encodes a single open reading frame (ORF) of 1627 amino acids (FIG. 1A; SEQ ID NO:1–2). The insertion is flanked by two LTRs of 251 bp with greater than 98% nucleotide identity. A five-base direct repeat (TGCTA) is found on either side of Ty5-6p; it is likely the target site duplication generated upon transposition. Ty5-6p shares 93.6% nucleotide identity to the defective S. cerevisiae element, Ty5-1. The two elements differ primarily by a deletion in Ty5-1 that extends from bases 1475 to 3703 and includes the putative coding region for integrase (see below and FIG. 1A). The boundaries of this deletion are delimited by two six-base pair direct repeats, which may have facilitated loss by recombination.

The Ty5-6p ORF shows significant similarity to proteins encoded by other retrotransposons and retroviruses (Xiong and Eickbush 1990) (FIG. 1B). Near the 5' end is a cysteine motif or finger domain that characterizes LTR-retroelement gag proteins, and is thought to be involved in binding RNA. The structure of the Ty5 finger domain, however, is different from those of other retroelements in the spacing of conserved cysteines (typically $CX_2CX_4HX_4C$ vs. $CX_2CX_3HX_4C$ for Ty5; C=cysteine; X=unspecified other amino acid). The ORF also shows similarity to retroelement pol proteins, including amino acid sequence domains for protease (PR), integrase (IN), reverse transcriptase (RT) and RNase H (RH). The RT domain shares the highest amino acid similarity to the *D. melanogaster* copia element. This similarity, and the fact that IN precedes RT, clearly place Ty5 within the Ty1-copia group elements, a class of LTR retrotransposons found in the genomes of diverse eukaryotes. In view of the regions of sequence similarity to Ty1-copia elements, it is surprising that the Ty5-6p element exhibits target specificity for telomeres and silent regions of the genome. Ty1, by contrast, has target specificity for tRNA genes.

The DNA sequence of Ty5-5p differed from Ty5-6p by six nucleotide substitutions and a single A insertion (FIG. 1A). Four of the six substitutions reside in the last 150 base pairs of the 3' LTR and lie outside the Ty5-5p ORF. One of the internal domain substitutions is silent (base 897) and the other (base 1186) results in an amino acid change from Cys in Ty5-6p to Phe in Ty5-5p. This change may affect protease function since it is in the predicted active site for protease. The single A insertion occurs in a stretch of $A_7$ and creates a frameshift before the RT domain. Frameshifts immediately before RT have not been observed in other retroelements, and this mutation is believed to render Ty5-5p nonfunctional. It is important to note that neither Ty5-5p nor Ty5-6p have a frameshift or stop codon at the junction of their gag- and pol-like domains (i.e. in the vicinity of protease (FIG. 1A)). This genomic organization is unusual for retroelements in general, but has been observed for certain Ty1-copia group retrotransposons, including copia and several plant elements (e.g., Mount and Rubin 1985; Voytas and Ausubel 1988), as well as the Tf1 element from *Schizosaccharomyces pombe* (Levin et al. 1990).

Figure 1C:
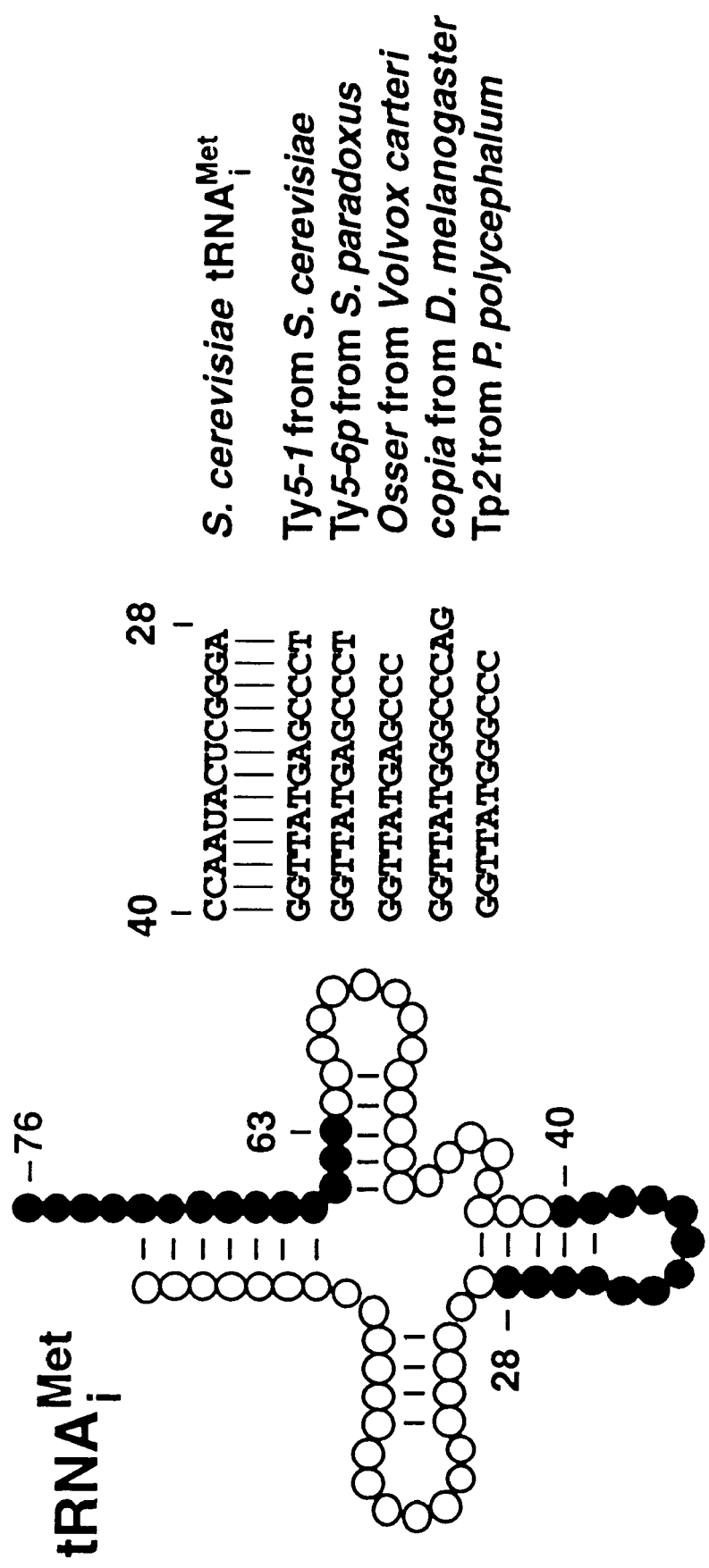
Figures 2A, 2B:
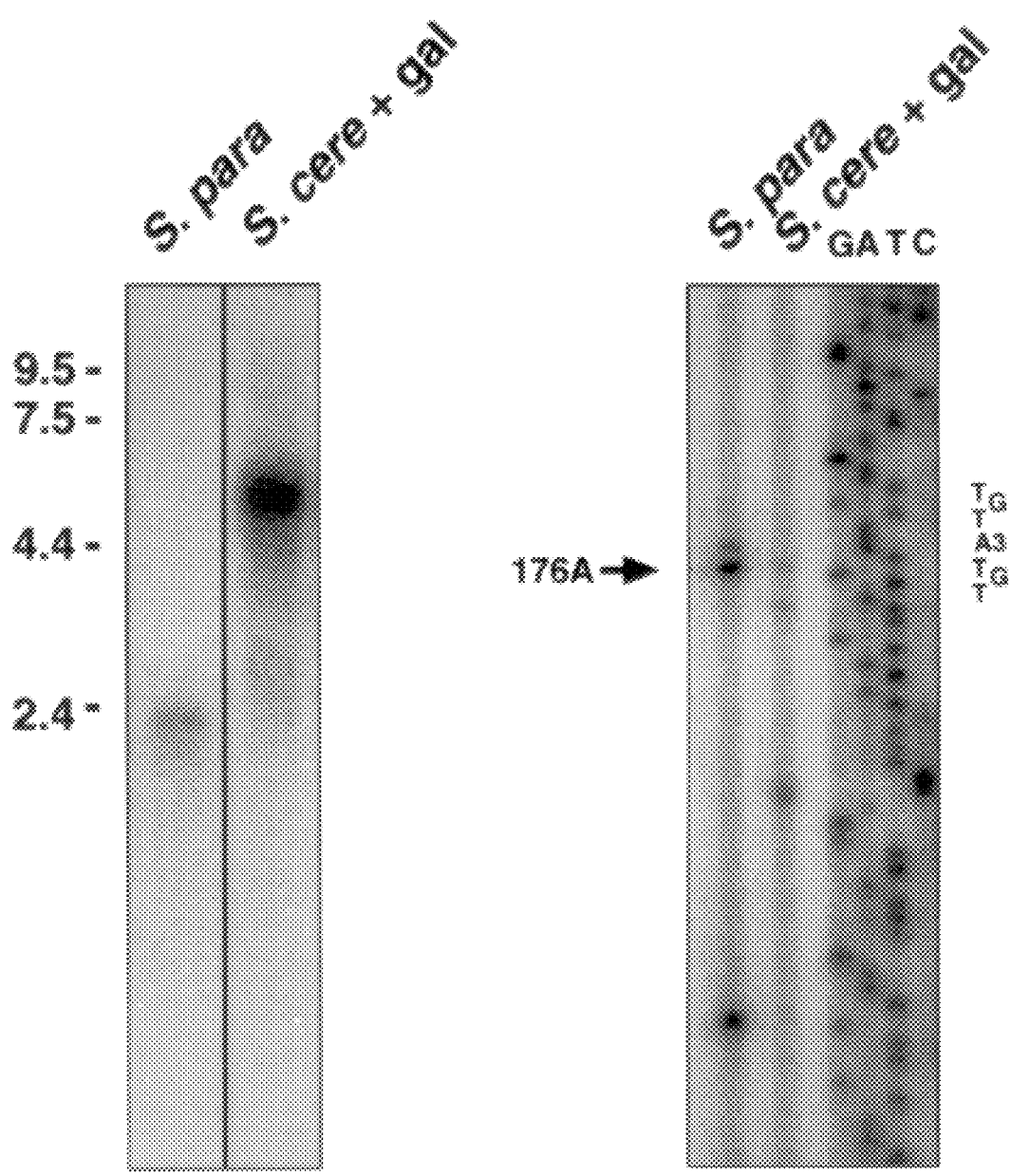
FIG. 2A–2C illustrates analysis of Ty5-6p transcripts.
Figure 2C:
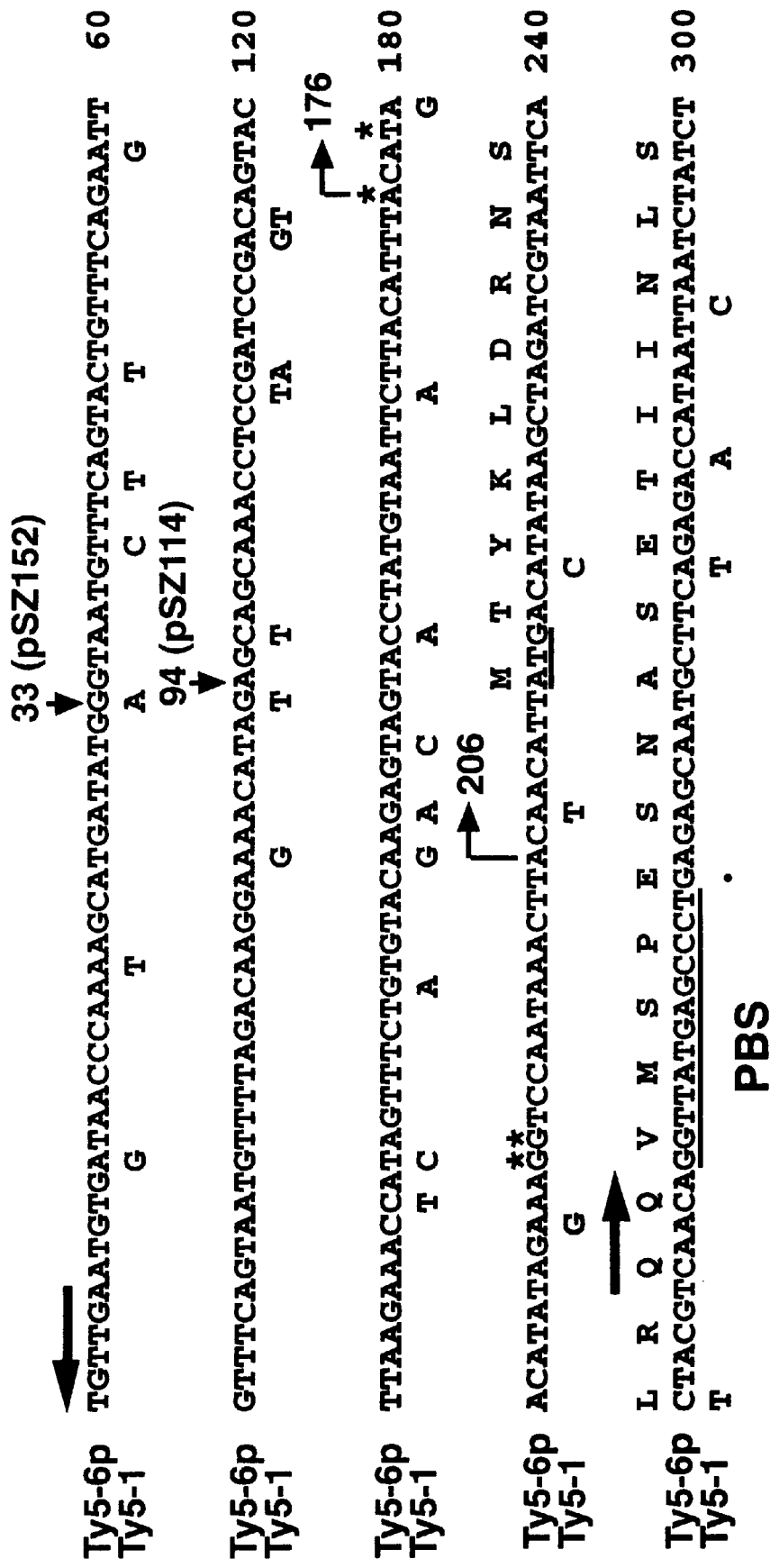

Immediately adjacent to the 5' LTR of both *S. paradoxus* and *S. cerevisiae* Ty5 elements are ten nucleotides that are complementary to the anticodon stem-loop of the *S. cerevisiae* initiator methionine tRNA (FIG. 1C, 2C). For most LTR retrotransposons and retroviruses (including the other four families of Ty elements), this region constitutes the primer binding site (PBS) and is complementary to the 3' end of a host tRNA. Base-pairing between the PBS and a host tRNA is used to prime DNA synthesis during reverse transcription. Several retrotransposon families have been identified with PBSs similar to Ty5, and complementarily to the host initiator methionine tRNA begins at the exact same position in the anticodon stem (FIG. 1C).

Northern analysis of poly(A) mRNA prepared from *S. paradoxus* revealed a single low abundance transcript of 2.4 kb, which does not correspond in size to the predicted full-length transcript (~5 kb) (FIG. 2A). Shorter transcripts generated by splicing have been observed for the closely related *D. melanogaster* copia elements, where differential splicing regulates the stoichiometry of gag and gag-pol gene products (Yoshioka et al. 1990). The 2.4 kb Ty5 mRNA, however, hybridizes to probes corresponding to both the gag- and pol-like regions of Ty5; thus it is concluded that it is not the product of a similar splicing event (probes a and b, FIG. 1A, FIG. 2A, and data not shown). In addition, the well-conserved splice-site consensus sequences are not found in Ty5-6 (Rymond and Rosbash 1992). It is possible that the 2.4 kb mRNA is the product of a partially deleted Ty5 derivative.

Transcription of Ty5-6p was placed under galactose control by replacing part of the 5' LTR with a GAL1-10 upstream activation sequence (UAS). Two different constructs were generated, which differed in the site of the GAL1-10 UAS fusion (base 33, pSZ152 and base 94, pSZ114; FIG. 2C). Only pSZlS2 generated high levels of galactose-induced message as indicated by northern analysis (FIG. 2A). A single mRNA was detected, which corresponds to the expected full-size Ty5 transcript; no smaller mRNAs were observed with probes corresponding to either the 5' or 3' regions of the Ty5 ORF. Both the galactose-induced message and the 2.4 kb mRNA from *S. paradoxus* were used to map transcription start sites by primer extension. For the *S. paradoxus* message, major start sites were identified at bases 176 and 206 within the 5' LTR (FIG. 2B, 2C).

The start site at base 176 was shared with the galactose-induced Ty5 message from pSZ152 (FIG. 2B); this construct is transpositionally active (see below), suggesting that base 176 is the actual start site of the Ty5 genomic mRNA.

The galactose-inducible Ty5-6p construct was modified to facilitate detection of transposition by incorporating a selectable marker gene between the end of the Ty5-6p ORF and the beginning of the 3' LTR (FIG. 3A). A HIS3 marker gene designed to specifically detect Ty1 transposition by reverse transcription was used (Curcio and Garfinkel 1991). The HIS3 gene carries an artificial intron (AI) inserted into the HIS3 coding sequence in the antisense orientation, which blocks HIS3 gene expression. The his3AI marker, however, is oriented in Ty5-6p such that the intron is on the sense strand of the retrotransposon. The intron, therefore, can be spliced from the Ty5-6p transcript, and a functional HIS3 gene can be generated through reverse transcription and integration into the genome. A similar construct was also generated using Ty5-5p, which has the naturally occurring frameshift mutation before RT.

Patches of *S. cerevisiae* cells carrying the two Ty5 constructs were grown on galactose-containing media to induce transcription and transposition and then replica plated to media lacking histidine to select for putative transposition events (FIG. 3B). His$^+$ cells arose only from patches containing the Ty5-6p construct. The frequency of His$^+$ cells after 48 hrs of galactose induction was approximately 1.5× $10^{-4}$ (FIG. 3C). The absence of His$^+$ cells from the Ty5-5p construct suggested that no functional reverse transcriptase was synthesized. Without wishing to be bound by any particular theory, it is postulated that this was due to the frameshift mutation and/or the amino acid substitution in protease. The His$^+$ phenotype was dependent upon galactose induction, indicating a requirement for Ty5-6p transcription.

Figure 4:
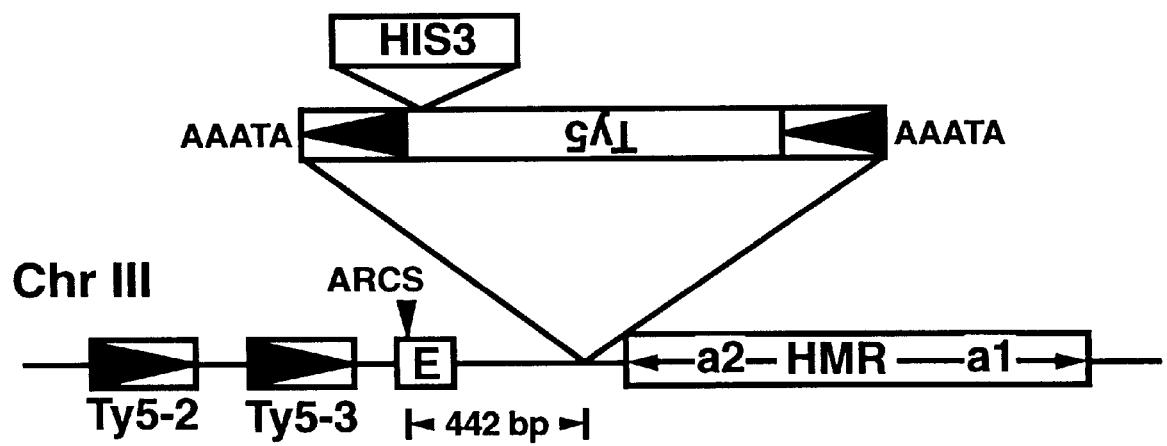
FIG. 4 illustrates the site of insertion of a de novo Ty5 transposition event at the HMR locus on chr III. The HMR locus is depicted as an open box, with the a1 and a2 genes noted by arrows. E denotes the transcriptional silencer of HMR, and the arrowhead marks the ACS within HMR-E. The site of Ty5 integration is 442 bases from this ACS. The five bases shown on either side of the element are the target site duplications generated upon integration. Upstream of HMR-E are two native solo Ty5 LTRs.

The reconstituted HIS3 gene generated by reverse transcription can integrate into the genome either by transposition or recombination. These two events can be distinguished because transposition generates target site duplications. Southern hybridization analysis of four independent His$^+$ strains revealed that each carried a Ty5 insertion on a uniquely sized restriction fragment, indicating that the marked Ty5-6p had integrated into different locations in the genome. Genomic DNAs were prepared from four His$^+$ strains that had lost the parental pSZ152 plasmid after selection on 5-FOA. DNA was digested with XhoI, which does not cut within Ty5-6p and hybridized with a HIS3 probe, which does not hybridize to the original strain. Each strain carries a HIS3 gene on a uniquely-sized XhoI fragment that is larger than the plasmid-borne Ty5-6p construct (i.e. 6.5 kb), consistent with transposition of a Ty5 element. One transposition event was cloned and the sequences flanking the Ty5 element were determined. These sequences matched the sequence of chr III near the HMR locus (Oliver et al. 1992). Moreover, a 5-bp direct repeat immediately flanking the element was generated upon integration, as this 5-bp sequence is present as a single copy on chr III (FIG. 4). Interestingly, the integration site is near HMR-E, the cis-sequences required for transcriptional silencing at HMR (see Laurenson and Rine 1992). More specifically, this insertion is 442 bp from the autonomously replicating consensus sequence (ACS) in HMR-E, which serves as an origin of replication. The presence of a target site duplication indicates that Ty5-6p is transpositionally competent, and the site of integration reflects the target specificity for silent chromatin.

To further investigate Ty5 target preference, chromosomes from 148 independent His+ strains were separated by pulsed-field gel electrophoresis and transferred to nylon membranes. Sixty-one strains (41%) had multiple chromosomes that hybridized strongly with HIS3 probes. Eighty-seven of the 148 strains (59%) each had single chromosomes carrying Ty5 insertions (Table 1). Of these 87 strains, 26 (~30%) had insertions located on chr III. Southern hybridization analysis performed on 22 of these strains indicated that each had a single Ty5 insertion. If the size of the chromosome targets are taken into account, the chr III insertions occurred at a relative density of approximately one per 12 kb. This density is more than four times greater than observed for chromosomes I and VI, seven times greater than observed for chr XI, and at least ten times greater than observed for all other chromosomes.

The four native Ty5 insertions on chr III and the one de novo transposition event described above are all located near the left telomere or the HMR-E transcriptional silencer. To determine whether the genomic organization of Ty5 elements is a consequence of preferential integration at these sites, the polymerase chain reaction (PCR) was used to map the exact location of de novo Ty5 insertions in the collection of strains carrying chr III insertions. Sequences flanking these elements were amplified by either inverse PCR (Ochman et al. 1988) or standard PCR using Ty5-specific oligonucleotides and oligonucleotides that flanked potential target sites, namely the telomeres and the E and I transcriptional silencers at HML and HMR. PCR products were sequenced directly and used to precisely map the target site of integration by comparison to the chr III sequence (Oliver et al. 1992). Sequences were determined for 19 of the 26 independent chr III insertions. Flanking sequences on both sides of four insertions were determined and shown to have 5 bp target duplications, indicating they arose by transposition. No consensus sequence can be deduced from the known Ty5 target sites, suggesting that Ty5 integration is sequence-independent.

Figure 9:
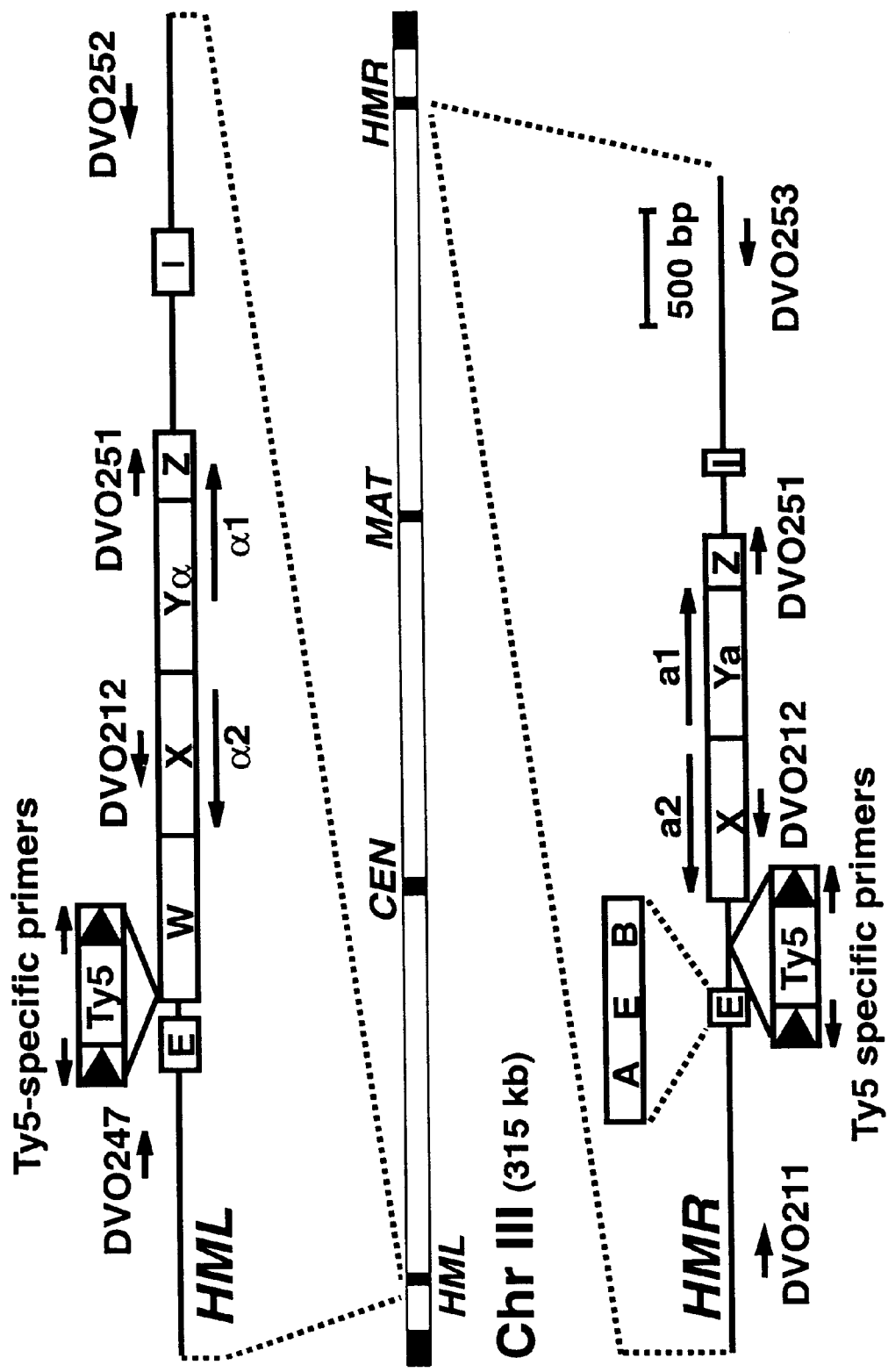
FIG. 9 summarizes the results of a PCR assay to quantitate the frequency of Ty5 transposition to HML-E and HMR-E. The shaded bar indicates chr III. Expanded views are shown for HML and HMR, and E and I designate the flanking transcriptional silencers. W, X and Z represent homologous regions shared between HML, HMR and MAT. Yα and Yα are specific for HML and HMR, respectively. Transcripts (a1, a2, a1, cc2) at each mating locus are shown by long horizontal arrows. An expanded view is shown for HMR-E, indicating the A, E and B sequence domains. Ty5 insertions are indicated by the labeled boxes, which are not drawn to scale. Names and locations of primers used for PCR are shown by short horizontal arrows.

The assembly of silent chromatin at HML and HMR is directed by flanking transcriptional silencers, designated E and I (FIG. 9). At HMR, silent chromatin extends at least 0.8 kb on either side of the E and I silencers, which corresponds to the region preferred by Ty5 for integration (Loo and Rine 1994). HML and HMR are integration hot-spots, and insertions near these loci account for roughly 10% of the total Ty5 transposition events.

Figure 10:
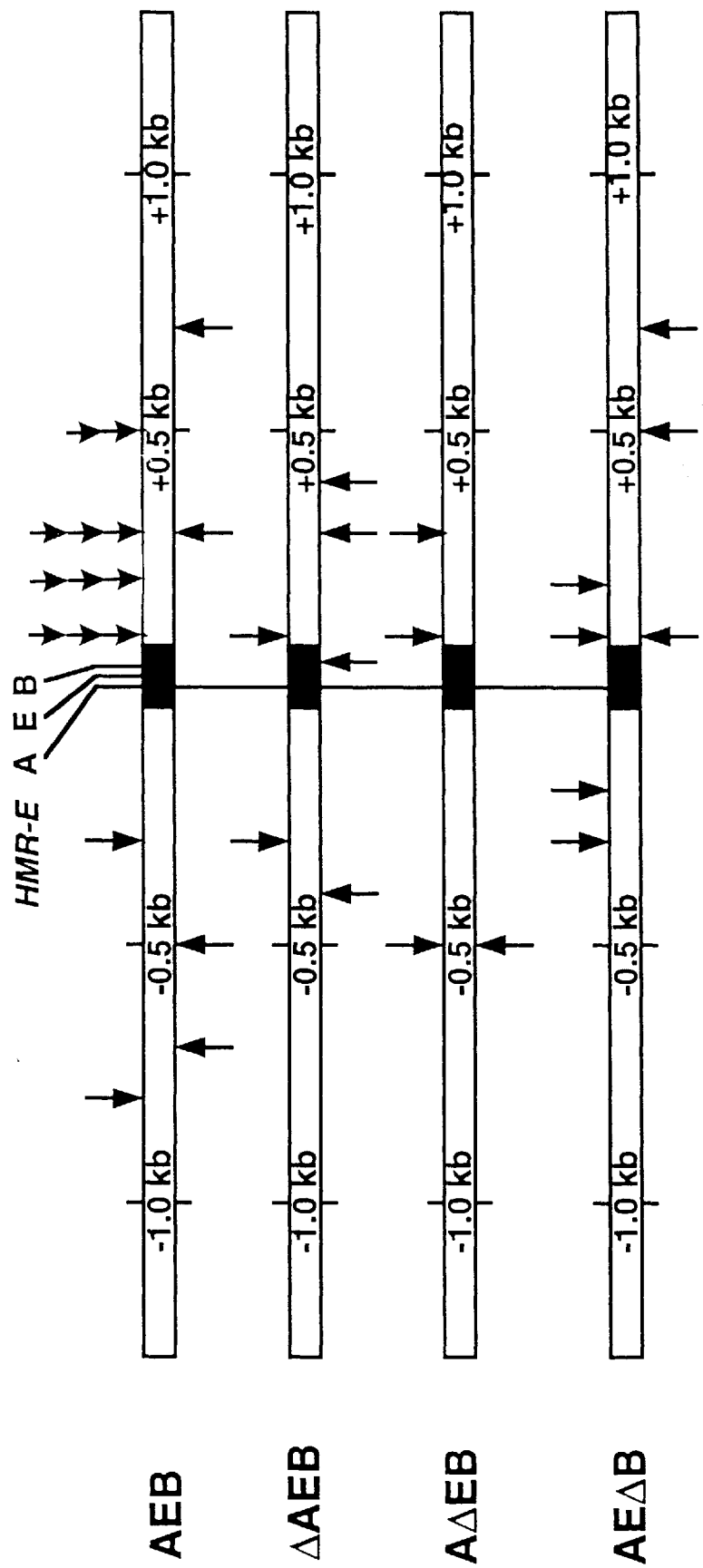
FIG. 10 summarizes the locations of Ty5 insertions near HMR-E. Ty5 insertions were identified throughout the –2 kb window represented by the open box. The reference point is the autonomously replicating consensus sequence (A) located within HMR-E. The genotype of HMR-E is indicated to the left. Arrows pointing down represent insertions in the same 5' to 3' orientation as the chromosome sequence, and arrows pointing upward represent insertions in the opposite orientation.

To identify factors important for Ty5 target specificity, we assayed transposition near the E and I transcriptional silencers in various mutant strains defective in the assembly or function of silent chromatin. Targeted transposition was measured in vivo, and transposition events were identified genetically using a his3AI marker gene. The expression of this marker is only activated upon reverse transcription of Ty5 MRNA and subsequent integration. For a given mutant, 600–1000 His+ strains were randomly collected, which represent independent Ty5 transposition events as described hereinbelow. The polymerase chain reaction (PCR) was used to identify Ty5 insertions at particular silencers by amplifying pools of genomic DNA from His+strains with a Ty5-specific and two silencer-specific primers as described hereinbelow (FIG. 9). All Ty5 insertions were recovered within about a 2 kb window encompassing a given silencer, the region preferred by Ty5 for integration. Targeting was evaluated in strains carrying cis-acting mutations in the well-studied HMR-E transcriptional silencer. HMR-E consists of three sequence domains, called A, E and B, which bind the origin recognition complex (ORC) and the transcription factors RAP1 and ABF1, respectively (Laurenson and Rine 1992). Although deletion of any one of these domains causes slight depression of transcription at HMR, deletion of any two or all three domains completely disrupts HMR silencing (Brand et al. 1985, Brand et al. 1987). Using the PCR assay, the frequency of transposition near HMR-E was determined in strains carrying various combinations of deletions in the three HMR-E domains (Table 3). In the wild type strain, 1.9% (17/908) of Ty5 transposition events occurred near HMR-E and 2.2% (20/908) occurred near HML-E, the latter of which served as an experimental control. Transposition to HMR-E was not significantly reduced in the ΔB strain, however, it was significantly reduced by three fold ($P<0.05$) and four fold ($P<0.01$) in the ΔA and ΔE strains, respectively. We mapped the position of Ty5 insertions near HMR-E in these strains and found no obvious change in integration pattern (FIG. 10). Most of the insertions were within 800 bp of the A site (the autonomously replicating consensus sequence) within HMR-E. Transposition frequency near HML-E was not altered in strains with single domain deletions.

For strains with any two or all three HMR-E domains deleted, no Ty5 insertions were recovered near HMR-E (Table 3). This corresponds to more than a 13-fold reduction in the frequency of targeted transposition. Because deletion of any one of the three domains only slightly affects silencing at HMR, and deletion of any two or all three completely disrupts HMR silencing, targeted transposition by Ty5 is directly correlated with the assembly of silent chromatin (Brand et al. 1985). For most of these mutants, transposition frequency near HML-E was approximately three fold reduced ($P<0.05$) compared to the wild type, indicating that the transcriptional status at HMR influences targeting to HML.

Characterization of mutants in cis-acting sequences at HMR-E suggested that protein components of silent chromatin may play an important role in Ty5 target specificity. The SIR1, SIR2, SIR3 and SIR4 genes encode components of silent chromatin (Laurenson and Rine 1992). Deletion of SIR2, SIR3 or SIR4 completely disrupts transcription silencing at HMR, HML and telomeres. Deletion of SIR1 results in epigenetic depression at HMR and HML but does not influence silencing at the telomeres. Overall transposition frequencies in strains containing mutations in each of the SIR genes showed at most a five fold reduction compared to wild type. Because transposition frequency reflects integration activity, it does not necessarily indicate integration specificity.

The frequency of Ty5 transposition near the silencers flanking HML and HMR was evaluated using a PCR assay similar to the one outlined in Example 7 and FIG. 9. This assay, however, also determined integration events near the I silencers. The screen revealed that Δsir1 has only a 2–3 fold reduction in targeting. Significantly, targeted transposition in Δsir2 was reduced 4–5 fold ($P<0.05$) (Table 4). The efficiency of targeted transposition decreased dramatically (10 fold) in Δsir3. Among 230 transposition events characterized in Δsir4, no Ty5 insertions were detected near the HM silencers (Table 4). This corresponds to at least a 14 fold decrease in the frequency of targeted transposition.

The above experiments indicate that silent chromatin determines Ty5 target preference. DNA sequences per se are not critical for target choice, since deletion of any one of the three HMR-E sequence domains does not dramatically reduce targeting. Rather, the data indicate that proteins recruited by these cis sequences are responsible for target specificity. The A, E and B domains of HMR-E interact with ORC, RAP1 and ABF1, respectively (Laurenson and Rine 1992). These proteins are assembled into silent chromatin along with other proteins, such as SIR1–SIR4. Mutations that disrupt silencing, whether in cis sequences or trans-acting factors (e.g. SIR2–SIR4), also dramatically decrease targeted transposition.

SIR3 and SIR4 are especially important for target site selection by Ty5, since the absence of these proteins results in more than a 10 fold decrease in targeted integration. These proteins are structural components of silent chromatin, and physically interact with each other and with other silent chromatin proteins, including RAP1, and the histones H3 and H4 (Moretti et al. 1994, Hecht et al. 1995). It is worth noting that some transposition events were still recovered at the HM lod in Δsir2 (3/210; 1.4%) and Δsir3 (2/340; 0.59%). The frequency of these events is significantly greater than expected for random events (−0.063%), indicating that targeting is still occurring. Although mutations in SIR2 and SIR3 disrupt transcriptional silencing, a crippled form of silent chromatin may still be present that can be recognized by Ty5. It is likely that a variety of transposition effects will be observed in the diverse genetic backgrounds known to perturb silent chromatin.

The proteins that make up silent chromatin carry out or influence numerous genetic processes, including DNA replication, transcriptional silencing and telomere function (Laurenson and Rine 1992). Silent chromatin can also direct transposition. Without wishing to be bound by theory, we propose that targeted integration by Ty5 is mediated by interactions between the Ty5 integration complex and one or more protein component of silent chromatin. Retroelements apparently sense specific chromatin domains during integration, for example, Ty1 and Ty3 recognize domains of pol In transcription, and that integrase interacts with the chromatin-related protein Ini1 (Devine et al. 1996, Chalker and Sandmeyer 1992, Kalpana et al. 1994, Laurenson and Rine 1992). Retroelements are the major class of interspersed repetitive DNAs in plant and animal genomes. Targeted integration is reflected by their non-random distribution, e.g., the clustering of retrotransposons in intergenic regions of maize and the association of some retroelements with heterochromatin and telomeres in Drosophila (SanMiguel et al. 1996, Biesseman et al. 1990, Levis et al. 1993, Pimpinelli et al. 1995).

Figure 5:
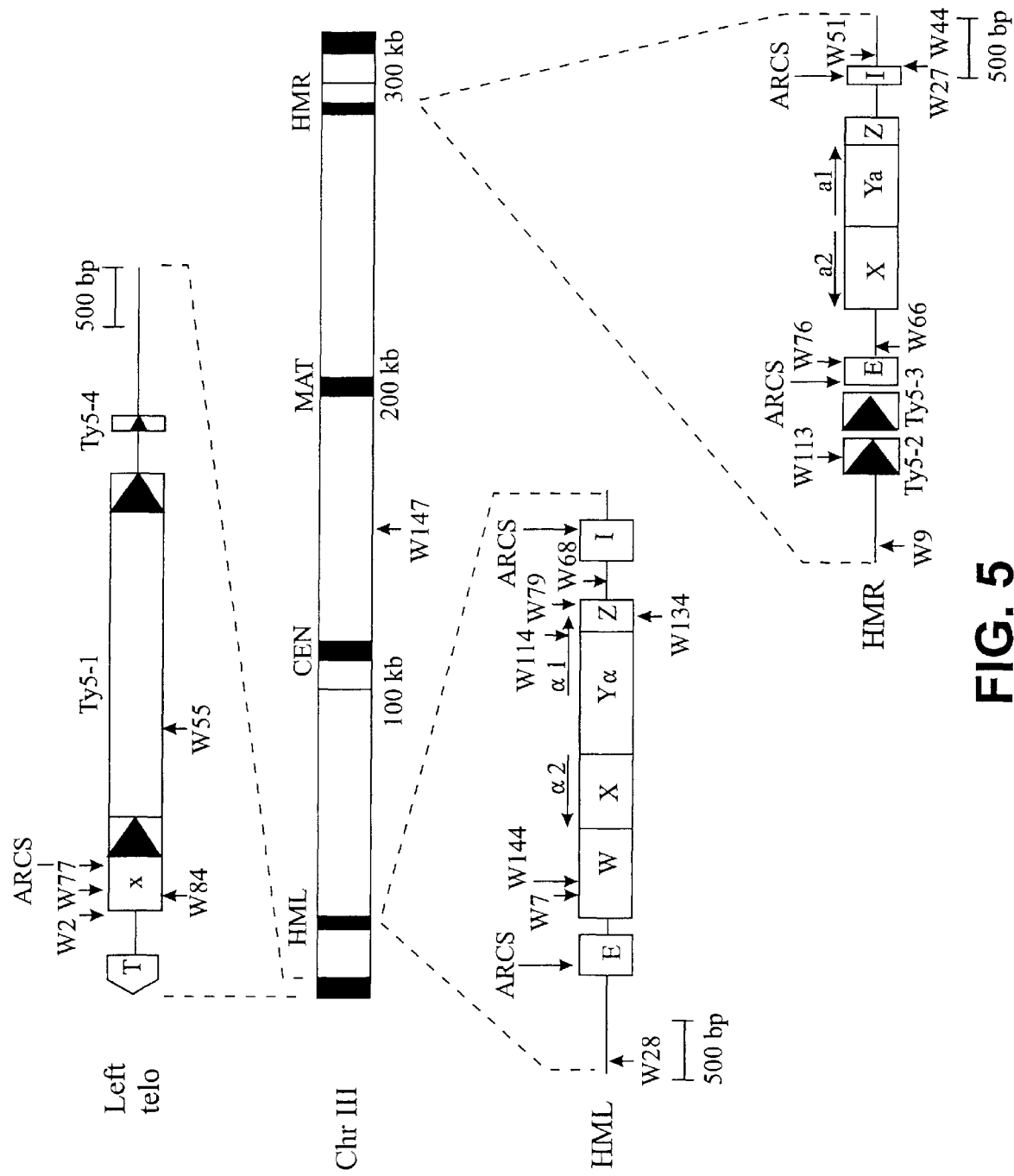
FIG. 5 illustrates the distribution of Ty5 transposition events on chr III. The shaded bar indicates chr III. Expanded views are shown for the left telomere, HML and HMR. Locations of de novo Ty5 integrations are indicated by the short vertical arrows and strain designation. Arrows pointing down indicate insertions in the same 5' to 3' orientation as the chr III sequence. Arrows pointing upward represent insertions in the opposite orientation. The positions of relevant ACSs are indicated by long vertical arrows. Native Ty5 elements are shown (i.e. Ty5-1, Ty5-2, Ty5-3, Ty5–4). For the left telomere, T designates the TG$_{(1-3)}$ repeats, and X is the sub-telomeric repeat. For HML and HMR, E and I designate the flanking transcriptional silencers. W, X and Z represent homologous regions shared between HML, HMR and MAT. Yα and Yα are specific for HML and HMR, respectively. Transcripts (a1, a2, a1, a2) at each mating locus are shown by horizontal arrows.

One Ty5 element (W147) is located near a hot spot for Ty1transposition (FIG. 5, Table 2). This insertion site is more than 5 kb from the nearest tRNA gene (SUF16); most de novo Ty1 insertions at this site are within 700 bp of this tRNA (Ji et al. 1993; Devine and Boeke 1996). Eighteen of the elements, however, were clustered near cis-acting sequences required for the assembly of silent chromatin. These included four insertions near the left telomere (W2, W55, W77, W84), three of which were located within 900 bp of the end of chr III. In addition, three insertions were located near the transcriptional silencer HML-E (W7, W28, W144), four near HML-I (W68, W79, W134, W114), four near HMR-E (W9, W66, W76, W113) and three near HMR-I (W27, W44, W51). No insertions were found near the right telomere; this may be due to inefficient PCR amplification of sequences in this region. The ACSs located within the transcriptional silencers and the telomeric X repeats have been used as reference points to orient native Ty5 insertions (Zou et al. 1995). De novo Ty5 insertions in silent chromatin are distributed on either side of these ACSs. Twelve of the 18 insertions occurred within 600 bp of an ACS, and all are located within 1.3 kb. Nine of the elements are oriented toward and eight away from the nearest ACS, indicating no apparent orientation specificity.

Sequences flanking fifteen newly transposed Ty5 elements were amplified by inverse PCR and used directly for DNA sequencing. These insertions were found to reside on ten different chromosomes (FIG. 1). Insertion W3 is 152 kb from the end of the chromosome IX. The remaining fourteen insertions are all subtelomeric and are within 15 kb of chromosome ends. The insertions show no orientation specificity with respect to the ends of the chromosomes; eight insertions are in the same 5' to 3' orientation as the chromosome sequence, and seven are in opposite orientation.

Nine of the 15 Ty5 insertions are within 0.8 kb on either side of the autonomously replicating consensus sequences (ACS) in the X repeat; three additional insertions are within 1.5 kb. Eight of the eleven telomeres that have Ty5 insertions also have Y' elements. These Y' elements separate the X repeat from the telomere by >5 kb. In all eight cases, Ty5 insertions are clustered within 1.5 kb of the ACS in the X repeat and are consequently several kb from the TG1-3 telomeric repeats. Without wishing to be bound by theory, it is believed that the X repeat serves as a nucleation site for factors important for Ty5 targeting.

Figure 12A:
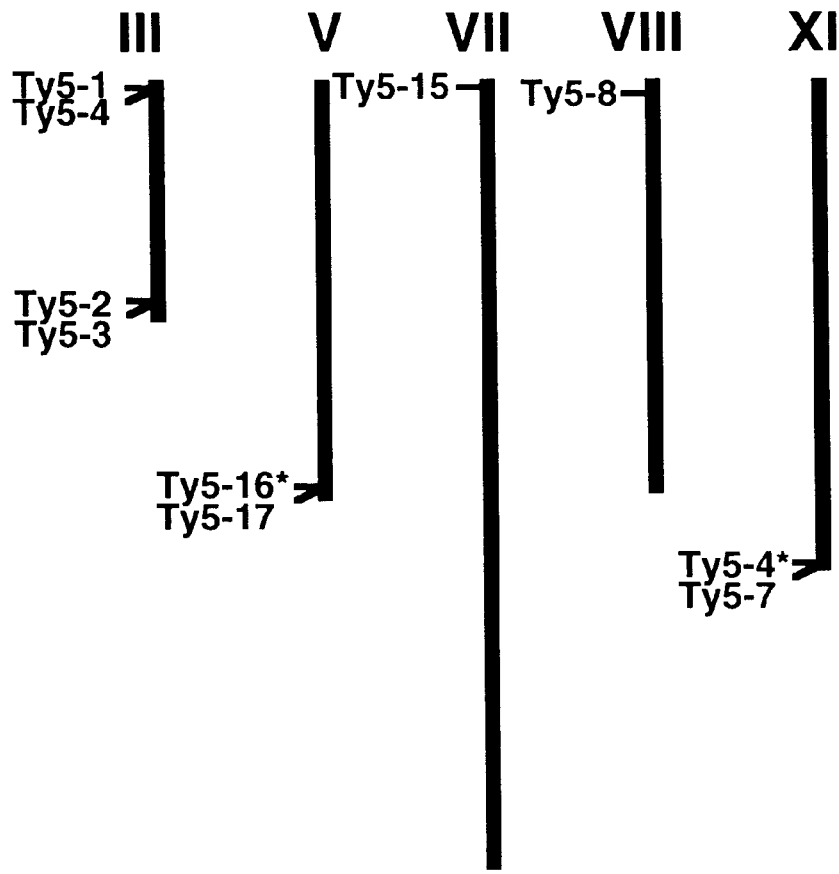
FIGS. 12A–12B show S. cerevisiae Ty5 elements.

The clear preference for Ty5 to integrate near the telomeres indicates an active role for Ty5 in shaping the organization of chromosome ends. The complete genome sequence of S. cerevisiae allows the identification of all Ty5 insertions in S288C, the strain used for the yeast genome project (FIG. 12A). Ten Ty5 insertions were found, including eight identified on chr III, VII, VIII and IX as described herein. The chr VII insertion (designated Ty5-15) was characterized only by Southern hybridization analysis. Two new insertions were identified on chr V, designated Ty5-16 and Ty5-17. The chr V insertions are near the right telomere but are in opposite orientation. Ty5-17 is within 600 bp of a X ACS, and Ty5-16 is within 2.7 kb.

Target site sequences were characterized for eight Ty5 insertions with fullsized LTRS. None of these insertions have the perfect 5 bp target site duplications characteristic of newly transposed Ty5 elements, although Ty5-16 has flanking target sequences with four identical nucleotides out of five (Table 5). The 5' target site of Ty5-17 is the same as the 3' target site of Ty5-16. However, the 3' target site of Ty5-17 is different from the 5' target sites of these two insertions, suggesting that a gene conversion event, or two sequential reciprocal recombination events, occurred between these elements.

Figure 12B:
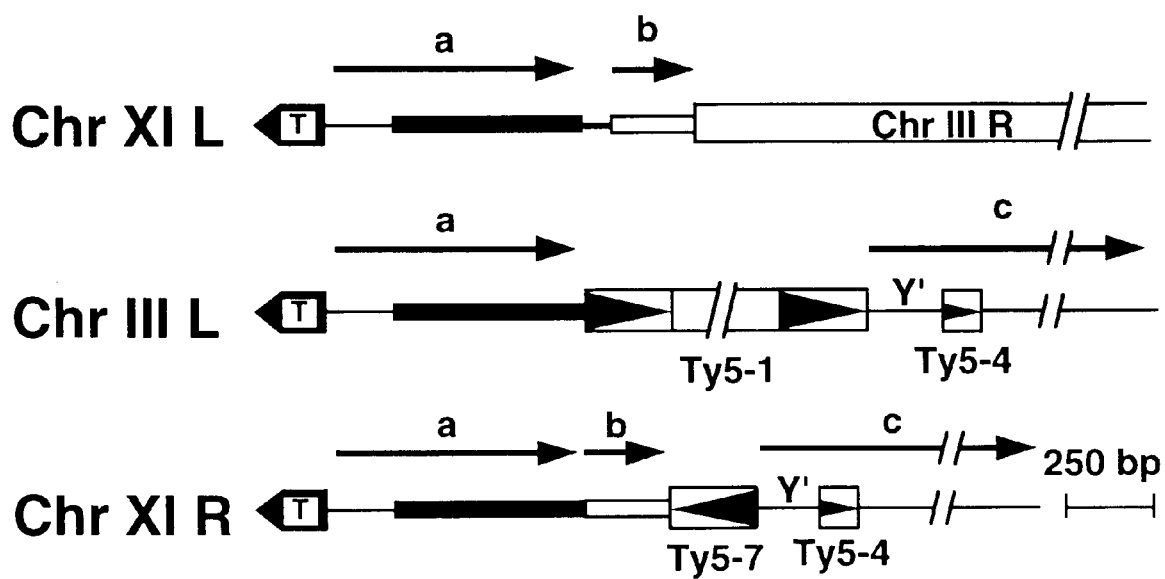

Some Ty5 elements mark boundaries of duplicated sequences in the S. cerevisiae genome. Genome sequencing efforts have identified extensive duplications between the telomeric regions of chr III and chr XI (Gromadka et al. 1996, Oliver et al. 1992, Dujon et al. 1994). Four Ty5 insertions are present in these duplicated regions (FIG. 12B). The chromosome ends, including the X repeat, are similar between the chr III left telomere and both telomeres of chr XI (region a). The similarity ends at the Ty5-1 insertion on chr III. Downstream of region a, the chr XI left-end has a unique 50 bases and both chr XI ends share a second duplicated sequence (region b). For the chr XI left-end, the b region terminates in sequences that have been duplicated from the right-end of chr Ill. The right-end of chr M, however, has a Ty5 insertion at the end of the b region (Ty5-7). This insertion has different target sites from Ty5-1 and is in the opposite orientation, clearly indicating that they are different insertions. Centromere proximal to Ty5-1 and Ty5-7 are several kb of duplicated sequences (region c), including a Ty5 insertion (Ty5-4). It has previously been noted that the beginning of the c region contains 140 bp of a Y' element (Louis 1995). The location of Ty5-1 and Ty5-7 at the boundaries of rearrangements suggests that these elements have played a role in these events.

A functional *S. paradoxus* Ty5 element (Ty5-6p) was identified that shares more than 90% nucleotide identity with the previously characterized, non-functional *S. cerevisiae* element Ty5-1 (Voytas and Boeke 1992). The genomic organization of Ty5-6p and sequence similarities between its reverse transcriptase and those of other retrotransposons suggest that it is a member of the Ty1/copia group elements (Xiong and Eickbush 1990). Ty5-6p, however, has unexpected and distinguishing features that distinguish it from the previously characterized yeast Ty1/copia group elements (i.e. Ty1, Ty2, Ty4; (Boeke and Sandmeyer 1991)): First, the Ty5-6p gag and pol genes are encoded within a single open reading frame. In most retrotransposons and retroviruses, these two genes are differentially expressed, typically due to translational frameshifting or readthrough (Jacks 1990). The related *D. melanogaster* copia elements also encode a single ORF and use differential mRNA splicing to regulate gag and pol expression (Yoshioka et al. 1990). A single full-length mRNA was detected from the transpositionally active Ty5-6p element in *S. cerevisiae* suggesting that Ty5 utilizes a different regulatory mechanism. The Tf1 element of *S. pombe* is transcribed as a single mRNA and also encodes a single ORF (Levin et al. 1990). Gag/pol stoichiometry of Tf1 is regulated by differential protein stability (Atwood et al. 1995).

A second unusual feature of Ty5 is the primer binding site (PBS) for reverse transcription, which is complementary to the anticodon stem-loop of the *S. cerevisiae* initiator methionine tRNA. This unusual PBS is also found in copia and a few related retrotransposons from diverse organisms (Voytas and Boeke 1993). For the copia elements, the initiator methionine tRNA is cleaved in the anticodon stem-loop by an unknown mechanism to generate the primer used to initiate reverse transcription (Kikuchi et al. 1986).

Thirdly, and importantly, the Ty5-6p has significant target specificity for insertion into silent regions of the eukaryotic genome, including but not limited to telomeres and other silent chromatin.

A Ty5 transposition assay was developed for *S. cerevisiae* by placing Ty5-6p under the transcriptional control of the GAL1-10 promoter. This assay exploited a his3AI marker gene to select for replication by reverse transcription (Curcio and Garfinkel 1991). Histidine prototrophs were selected after induction of Ty5-6p transcription, and a newly transposed element was cloned. This insertion arose by transposition, as it was immediately flanked by 5-base pair duplications of target DNA generated upon integration. The promoter of the HIS3 marker in this insertion was within 750 bp downstream of the transcriptional silencer at HMR-E, which can repress transcription of some genes as far away as 2.3 kb (Brand et al. 1985). HIS3 is not effectively silenced when inserted at HMR; this study used HIS3 to identify Ty5 insertions throughout other silent regions on chr III (see below). In addition, silencing is not simply disrupted by the insertion of Ty5. Two insertions at HML-E (W7, W144, FIG. 5) are mating competent, indicating that HML is still repressed. It is not known if some transposition events went undetected due to the requirement of the transposition assay described herein for functional HIS3 expression.

Approximately 30% of the tested strains carried multiple Ty5 insertions localized to different chromosomes. These elements appear to be organized in arrays. Arrays of Ty1 have been observed (Weinstock et al. 1990), particularly in Ty1 integrase mutants, and these arrays are likely generated by recombination of cDNA into preexisting genomic Ty1 copies (Sharon et al. 1994). Lower rates of Ty5 transposition were observed in recombination deficient (rad52) hosts; thus, recombination is responsible for generating some His$^+$ cells. The present specification describes only the analysis of His$^+$ strains with single Ty5 insertions. In all such cases examined, the presence of flanking target site duplications indicates that these insertions were generated by transposition rather than by recombination.

Figure 6:
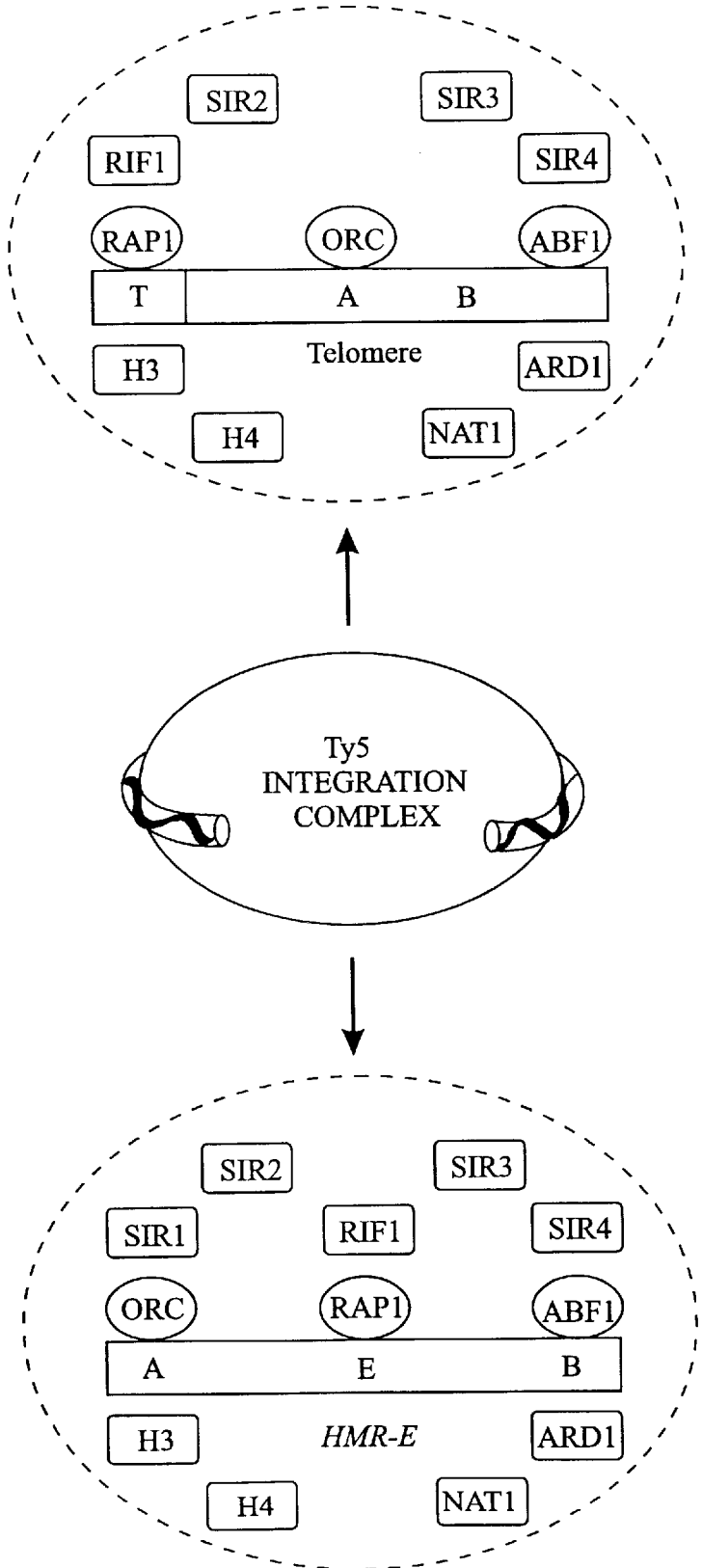
FIG. 6 shows Ty5 targets and components of silent chromatin. A, E and B denote protein binding domains at the transcriptional silencer HMR-E, the telomere, and the sub-telomeric X repeat (reviewed in Laurenson and Rine 1992). A is an ACS, which is bound by the origin recognition complex (ORC). E denotes RAP1-binding sites, which are the TG$_{1-3}$ repeats at the telomere and sequence 5' ACCCAT-TCATAA 3' (SEQ ID NO: 51) at HMR-E (note that the E domain is a component of the HMR-E silencer). B denotes ABF1-binding sites. Other regulators that act at these sites are shown schematically above the DNA-bound proteins.

HML and HMR encode genes that specify yeast mating type. These genes are not expressed until they are transferred to a third locus (MAT) in the middle of chr III by directed gene conversion. Transcriptional repression of HML and HMR is mediated by proteins that assemble at flanking cis-sequences, designated the E and I silencers (Laurenson and Rine 1992). Similar to the HM loci, the telomeres are also transcriptionally silent (telomere position effect) (Gottschling et al. 1990). Many proteins that play a role in silencing the HM loci also act at the telomeres and are required for telomere position effect (FIG. 6). Some of these proteins bind the sub-telomeric X repeat (Longtine et al. 1993), which is found at the ends of all chromosomes (Louis et al. 1994). Although X repeats are not required for silencing per se (Gottschling et al. 1990), they are highly conserved in *S. paradoxus*, suggesting they may serve a role in telomere structure (Zou et al. 1995).

We characterized in detail de novo Ty5 insertions on chromosome III, which represented ~30% of the transposition events in strains containing single insertions. Eighteen of 19 chr III insertions were near or within the cis-sequences that assemble silent chromatin. Using the ACS as a reference point, 12 insertions were clustered in either orientation within 600 bp of ACSs located in the sub-telomeric X repeat or the E and I regulatory regions; the remainder were within 1.3 kb of these ACSs. The proximity of Ty5 elements to silent chromatin is not limited to the chromosome III insertions. Target sites for several Ty5elements on other chromosomes were found to reside in telomeric regions.

The locations of fifteen newly transposed Ty5 insertions were mapped to ten chromosomes other than chr III, which are not known to have silent chromatin except at the telomeres. Fourteen of fifteen are located within 15 kb from the ends of these chromosomes. These results indicate that Ty5 is a subtelomeric repetitive element based on its location and polymorphic nature.

At the subtelomeric regions of *S. cerevisiae*, the X repeats and Y' elements are the two most abundant repetitive sequences (Chan et al. 1983). Y' elements are immediately adjacent to the telomere sequences and are found at the subtelomeric regions of most but not all chromosomes (Louis and Haber 1992). Internal to Y' elements are X repeats, which are found at the ends of all but one chromosome. Chromosome ends, therefore, have a relatively rigid organization; internal to the telomere sequences are Y' elements, followed by X repeats. In contrast, the location of Ty5 is very flexible. Insertions can be found within the telomere sequences, between X repeats and the telomere sequences or centromere-proximal to X repeats or Y' elements. Unlike Y' elements, Ty5 insertions can occur in either orientation with respect to the chromosome end. Ty5 transposition, therefore, has regional specificity rather than site-specificity.

The assembly of silent chromatin mediated by these silencers is critical for Ty5 targeting. Of the fourteen telomeric insertions identified in this study, and the four telomeric insertions on chr III, twelve are located within 0.8 kb of the X repeats. Particularly notable are insertions on chromosome ends with Y' elements, which are all >5 kb from the chromosome ends. The clustering of Ty5 insertions near X sequences indicates that some unique feature of the X repeat directs Ty5 integration. The X repeats, which are conserved among species of Saccharomyces, have binding sites for the origin recognition complex and the transcription factor ABFI.

Telomere repeat sequences are generated by reverse transcription, which is carried out by telomerase (Blackburn 1992). Telomerase is the only known reverse transcriptase not associated with retroelements, but it may have originated from a retrotransposon or a retrovirus. The Y' elements have some features of transposable elements; however, transposition of Y' elements has never been demonstrated. In contrast to the other repeat sequences, the Ty5 elements are typical LTR retrotransposons and actively transpose to subtelomeric regions. This provides direct evidence that subtelomeric repeats can originate from transposable elements. Moreover, the HeT and TART transposable elements of Drosophila melanogaster serve as telomeres (Biesseman et al. 1990, Levis et al. 1993).

Analysis of de novo transposition events clearly demonstrated that Ty5 generates five bp target site duplications. Characterization of endogenous insertions, however, showed that only one is flanked by such duplications. If the absence of target site duplications is due to random mutation, the LTR sequences among different Ty5 insertions should be degenerate to a similar extent as the target sites. The LTRs of Ty5-5p and Ty5-12p share more than 98% nucleotide identity with the transpositionally functional Ty5-6p LTR, suggesting that these insertions are not ancient and their target sites should not have mutated dramatically. Nonetheless, the target sites of Ty5-5p share no similarity and the target sites of Ty5-12p have only one nucleotide in common. It is difficult to argue that mutation alone could be responsible for the extreme differences in target site sequences.

A second possibility is that recombination between elements resulted in the lack of target site duplications. The five bp at the 5' target site of Ty5-5p are the same as those at the 3' target site of Ty5-14p, suggesting these two insertions recombined, resulting in the exchange of target sites. It is not known if the 3' target site of Ty5-5p is the same as the 5' target site of Ty5-14p; Ty5-14p has suffered a deletion of its 5' LTR. However, four nucleotides in the Ty5-5p 5' LTR are shared with the 3' LTR of Ty5-14p, suggesting that these LTRs originated from the same element. Evidence for recombination is also found among the S. cerevisiae elements. The 5' target sequence of Ty5-17 shares only two nucleotides with its 3' target sequence, but is the same as the 3' target sequence of Ty5-16; the target sites of Ty5-16 differ by only one nucleotide. Gene conversion between Ty5-16 and Ty5-17 is a plausible explanation, with the 5' target site of Ty5-16 subsequently mutating to give one nucleotide difference.

Recombination between repetitive sequences plays an important role in restructuring chromosomes. Ty5 has been involved in recombination events which have reorganized chromosomes in S. cerevisiae and S. paradoxus. For example, the 5' flanking sequence of Ty5-12p is located on chr V of S. cerevisiae but is duplicated on chr III and chr XI in S. paradoxus. The 5' flanking sequence of Ty5-5p is duplicated between chr III and chr XI in S. paradoxus, but is completely absent from S. cerevisiae. Similarly, duplicated sequences between chr III and chr XI in S. cerevisiae have boundaries that are marked by Ty5 insertions. Recombination between some subtelomeric repeats, such as Y' elements, has been well characterized (Louis and Haber 1992). Taken together, these observations clearly support the role of repetitive sequences, including transposable elements, in influencing the organization of chromosome ends.

Silent chromatin may turn off Ty5 transcription after integration. Ty5 transcripts were undetectable in strains with Ty5 insertions near HMR. Transcriptional silencing is also a feature of regions flanking pol III genes, preferred targets for Ty1 and Ty3 integration. Pol III transcription strongly inhibits transcriptional expression from adjacent RNA Pol II promoters (Hull et al. 1994). Although silencing near pol III genes may occur by a different mechanism than that at the telomeres and silent mating loci, transcriptional silencing may be a general means by which retrotransposition in yeast is regulated.

Most Ty5 integration events occurred in regions previously shown to occlude sequence-specific DNA binding proteins such as restriction endonucleases (Loo and Rine 1994). For example, sites for cleavage by HO endonuclease (which is involved in mating type switching) are found at all three mating loci, but cleavage is blocked at HML and HMR by silent chromatin (Laurenson and Rine 1992). It has long been known that during mating type switching, MATa cells preferentially recombine with HMLα, and MATa cells preferentially recombine with HMRa (reviewed in Haber 1992). The mechanism that determines this donor preference does not affect Ty5, as insertions occur at equal frequencies at both silent mating loci in either MATa or MATα strains of S. cerevisiae. Either the Ty5 integration complex can overcome barriers imposed by silent chromatin, or transposition occurs only when these regions are readily accessible, such as shortly after DNA replication.

Based on the strong bias for sites of Ty5 insertion and without wishing to be bound by any particular theory, we predict that targets are chosen through interactions between Ty5 proteins (such as integrase) and some component of silent chromatin (FIG. 6). The transcription factors TFIIIB and TFIIIC, which interact with the tRNA promoter, are likely candidates for determining Ty3 target specificity (Kirchner et al. 1995). Ty1 also frequently integrates upstream of pol III transcribed genes; however, the pattern of integration is considerably less precise and occurs over a 700 bp region upstream of target genes (Ji et al. 1993; Devine and Boeke 1996). Target specificity for Ty5 transposition is also imprecise, and no specific component of silent chromatin can be implicated as the interacting partner which confers target site preference based on the pattern of characterized Ty5 insertion sites.

The silent mating loci and telomeres of S. cerevisiae share many features with heterochromatin found in other eukaryotes, including late replication in S phase, association with the nuclear envelope and epigenetic gene repression (Roth 1995). Another interesting feature of heterochromatin is the association with transposable elements. For example, transposable elements are a major structural component of *D. melanogaster* heterochromatin (Karpen and Spradling 1992; Pimpinelli et al. 1995). Heterochromatin offers a "safe haven" for elements to integrate without negative genetic consequences for the host such as deleterious mutations in essential genes (Ji et al. 1993).

Native transposable elements associated with telomeric heterochromatin have evolved important cellular roles in some organisms. In *D. melanogaster*, two non-LTR retrotransposons, HeT and TART, can transpose preferentially to the ends of chromosomes and can serve as telomeres (Biessmann et al. 1990; Levis et al. 1993). In *S. cerevisiae*, another class of telomeric repeats, the Y' elements have structural features reminiscent of transposable elements (Louis et al. 1994). Y' elements have never been demonstrated to transpose, but they may be nonfunctional remnants of telomere-specific transposons. Amplification of Y' elements by recombination at the telomeres can suppress telomere-length mutations, such as esti (Lundblad and Blackburn 1993). Telomerase-independent elongation of telomeres has also been observed in some human cancer cell lines (Bryan et al. 1995). Ty5 amplification by transposition and/or recombination can also suppress telomere mutations. Telomerase is a reverse transcriptase, indicating the importance of reverse transcription in maintaining chromosome structure.

A further aspect of the present invention is the genetic engineering of Ty5-6p to incorporate heterologous DNA, and methods for the subsequent stable introduction and retrotransposition of the modified Ty5-6p into the genome of a eukaryotic cell. Plant cells and tissue, animal cells and tissue, and as particularly preferred, yeast cells, more preferably one of *Saccharomyces cerevisiae* and *Saccharomyces paradoxus*. Once incorporated into the genome of a eukaryotic cell, this modified Ty5-6p and the heterologous DNA carried within it can serve as genetic markers, which can be silent or expressed according to the choice of promoter sequence or lack thereof. If expressed and a suitable choice of the marker has been made, the expressed genetic marker carried on a modified Ty5-6p can serve to select genetically modified strains (for example, those modified in other ways and/or at other locations in the genome). Alternatively, the modified Ty5-6p can serve as a marker of a particular origin of a particular strain of interest; marked strains released into the environment could be followed by virtue of the native or a modified element or commercially used strains could be marked to identify potential infringing or unauthorized uses thereof. Where the ability to track or identify the parentage of an organism, expression of a gene is not required, and the native Ty5-6p element can be used. Because Ty5-6p incorporates preferentially into silent regions of the genome, the normal functioning of an organism or cell into which it has incorporated will not be disrupted. Encompassed within the present invention are methods for targeting DNA sequences to silent regions (including but not limited to telomeres) of the eukaryotic genome, especially the genome of yeast cells.

Methods for the introduction of genetic material into plant cells and tissue are well known to the art. Within the context of marking cells or tissue or a plant, the Ty5-6p or a derivative altered to contain a plant-expressible gene is introduced on a DNA vector which on its own cannot integrate or replicate in plant cells. Genetically engineered plant cells or tissue can be identified by a hybridization or polymerase chain reaction. Where an plant-expressible selectable marker is used, standard selection of the genetically engineered plant cells or tissue can be carried our using standard, well known methods. A preferred selectable marker is the kanamycin resistance marker from Tn5. Methods for the genetic manipulation of plant cells and tissue, include but are not limited to *Agrobacterium tumefaciens*-mediated DNA transfer, preferably with a disarmed T-DNA vector, electroporation, direct DNA transfer, and particle bombardment (see Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technol.* 11:522; Beck et al. (1993) *Bio/Technology* 11:1524; Koziel et al. (1993) *Bio/Technology* 11:194; Vasil et al. (1993) *Bio/Technology* 11:1533). Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. For efficient regeneration of transgenic plants, it is desired that the plant tissue used in the transformation possess a high capacity to produce shoots. For example, tobacco leaf discs and aspen stem sections have good regeneration capacity (Sitbon, F. (1992) supra)

Techniques for introducing and selecting for the presence of heterologous DNA in plant tissue are well known. For example, *A. tumefaciens*-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a suitable promoter fused to the coding sequence of interest and containing a transcription termination region are to be integrated into the plant cell genome by electroporation, cocultivation, microinjection, particle bombardment and other techniques known to the art. The expression cassette further contains a marker allowing selection of the expression cassette in the plant cell, e.g., genes carrying resistance to an antibiotic such as kanamycin, hygromycin, gentamicin, or bleomycin. The marker allows for selection of successfully transformed plant cells growing in the medium containing certain antibiotic because they will carry the expression cassette with resistance gene to the antibiotic.

Animal cells and tissue are also amenable to genetic manipulation to contain heterologous DNA according to well known methods, including but not limited to electroporation, particle bombardment, liposomes, receptor-mediated endocytosis, polyethylene glycol mediated transformation and other methods for transfection and transformation (see, e.g., *Methods in Enzymology*, Vol. 217). Selection techniques and markers, where desired, are also well known to the skilled artisan. Where a gene or coding sequence of interest is to be inserted in silent chromatin via Ty5-6p-mediated retrotransposition, that gene is inserted into Ty5-6p under the regulatory control promoter sequences which are resistant to silencing in heterochromatin. An exemplary silencing resistant promoter is that of the human XIST gene (Brown et al. 1992).

Genes of known sequence and useful for Ty-5-6p gene therapy applications include, but are not limited to, adenosine deaminase, the coding sequence for the functional chloride transport protein which complements the defect in cystic fibrosis (Alton et al. 1993. *Nature Genetics* 5: 135–142; Colledge, W. H. 1994. *Curr. Opin. Gene Develop.* 4:466–471), α-1 antitrypsin and cytokines for cancer treatments. Use of the targeting capability of Ty5-6p's retrotransposition machinery overcomes problems associated with current methods of gene therapy: the low efficiency and low targetability associated with liposome or naked DNA methods for gene therapy, the low capacity, replication risks and lack of targeting of retrovirus vectors, the immunogenicity and replication risks of adenovirus vectors, and the technical difficulties associated with Adeno-associated virus and Herpes virus vectors (discussed in Marshal, E. 1995. *Science* 269:1050–1055).

The targeting to silent regions of the chromosome prevents disruption of normal genetic function of the recipient, and the use of the silencing-resistant promoter allows expression of the coding sequence of interest carried within the Ty5-6p derivative.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985S) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. All references cited in the present application are incorporated by reference in their entirety herein.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1

Strains

The yeast strains used in this study include: *S. paradoxus* NRRL Y-17217 (Northern Regional Research Laboratory, Peoria, Ill.), wild-type *S. cerevisiae* strains SK1 and S288C for the characterization of Ty5 insertions and GRF167 (MATa his3D200 ura3-167) (J. D. Boeke, Johns Hopkins University, Baltimore, Md.), W303-1A (MATa ade2-1 can1-100 his3-11 leu2-3 trp1-1 ura3-1) (A. Myers, Iowa State University, Ames, Iowa). The *E. coli* strain XL1-blue (Stratagene, La Jolla, Calif.) was used for recombinant DNA manipulations. Transformation of *E. coli* and yeast strains was performed by electroporation as described (Ausubel et al. 1987).

Example 2

Ty5 Isolation and Sequence Determination

The construction and screening of the *S. paradoxus* genomic DNA libraries containing Ty5 elements has been previously described (Zou et al. 1995). Templates for DNA sequencing were generated by γδ mutagenesis of Ty5-5p and Ty5-6p subclones (Gold BioTechnology, Inc.). DNA sequence was obtained using the FMOL SEQUENCING KIT (Promega, Madison, Wis.) or by the Iowa State University Nucleic Acid Facility. Sequence analysis was performed using the Genetics Computer Group programs (Devereux et al. 1984). Sequences were determined for one DNA strand of Ty5-5p and both strands of Ty5-6p. The sequence of Ty5-6p is given in SEQ ID NO:1 (see also FIG. 1A).

Example 3

Analysis of Ty5 Transcription

Transcription of Ty5 was monitored by northern analysis (Ausubel et al. 1987). Filters were prepared with 0.7 mg poly(A) mRNA isolated from *S. paradoxus* strain NRRL Y17217 or with 15 mg total mRNA from GRF167 carrying plasmid pSZ152 (ySZ128) (see below). Hybridizations were conducted with probes corresponding to the gag- and pol-like domains of Ty5-6p (a and b, respectively, FIG. 1A) that had been radio-labeled by random priming (Promega, Madison, Wis.). The transcriptional start site of Ty5 was mapped by primer extension with the primer DVO207 (AGGGCTCATAACCTGTTGAC) (SEQ ID NO:25) as described (Ausubel et al. 1987).

Example 4

Ty5 Transposition Construct

To develop a Ty5 transposition assay, the Ty5-6p element was first modified to regulate its transcription by galactose. Specifically, the GAL1-10 UAS was PCR-amplified from plasmid pJEF1105 (Boeke et al. 1988) with primers DVO184 (TCTCGAGCCCCATTATCTTAGC) (SEQ ID NO:3) and DVO185 (CGTCGACTCATCCTATGGTTGTT) (SEQ ID NO:4). The PCR amplicon was then digested with XhoI and SalI and subcloned into the XhoI site of the URA3-based 2 μm plasmid pRS426 (Stratagene, La Jolla, Calif.), to yield pSZ138. Ty5-6p sequences from position 33 to 442 were amplified from a Ty5-6p HindIII subclone with primer DVO182 (GGGTAATGTTTCAGT) (SEQ ID NO:5) and the universal primer. This PCR product was subcloned into the PCR cloning vector pT7Blue (Novagen) to create pSZ135, which has a SalI site upstream of position 33 in Ty5-6p. A SalI-HindIII fragment from pSZ135 was subcloned into the SalI-HindIII sites of pSZ138 to yield pSZ139, which placed the GAL1-10 UAS upstream of position 33 in the Ty5-6p 5' LTR.

To select Ty5-6p transposition events, a marker gene was inserted after the Ty5 ORF and before the 3' LTR. To generate appropriate restriction sites, the 3' end of Ty5-6p was amplified by two pairs of primers: DVO187 (CGGTACCTATATACCAC) (SEQ ID NO:6), DVO189 (GAGATCTGTTATTTTGCAGTTTCT)(SEQ ID NO:7) and DVO188 (CAGATCTCATGCGTATTCAGTT) (SEQ ID NO:8), DVO190 (TGGATCCTGTTGACGTAGTGAATTA) (SEQ ID NO:9). Both PCR amplicons were sequentially subcloned into the KpnI-XhoI and BamHI sites in pRS426 to yield pSZ128. This resulted in an insertion of polylinker sites, including a ClaI site at position 5098 in Ty5-6p. Both XhoI and BamHI sites in the pRS426 polylinker were destroyed during cloning. A BamHI-KpnI fragment from pSZ128 and a HindIII-KpnI fragment from the internal sequence of Ty5-6p were subcloned into the BamHI-HindIII sites in pSZ139 by three-way ligation to yield pSZ147. Finally, a ClaI fragment with the his3AI marker from pGTymhis3AI was inserted to the ClaI site in pSZ147 (Curcio and Garfinkel 1991). A ligation product with the his3AI gene in the antisense orientation to Ty5-6p was chosen as the final version of the Ty5 transposition construct, pSZ152. A Ty5-5p transposition construct was generated by replacing the Ty5-6p internal HindIII-KpnI sequence with that of Ty5-5p to yield pSZ151. All PCR products were confirmed by DNA sequencing.

Example 5
Ty5 Transposition Assay

S. cerevisiae strain GRF167 was transformed as described (Ausubel et al. 1987) with plasmid pSZ151 and pSZ152 by electroporation to yield ySZ127 and ySZ128. Transposition assays were performed with modifications as described (Keeney et al. 1995). Cells were grown as patches on synthetic complete medium without uracil and with glucose SCU/glucose plates (Ausubel et al. 1987) at 30° C. for two days. The patches were subsequently replica plated to SCU/galactose medium (Ausubel et al. 1987) and grown for an additional two days at 23° C. Finally, the patches were replicated to SC media without histidine (SC-H) and incubated for about 60 hours to select His$^+$ cells. To quantitate the rate of His$^+$ cell formation, cells were scraped from patches on SC-U/galactose plates after two days growth and suspended in 10 ml dH$_2$O. 200 ml of the cell suspension and 200 ml of a 10$^{-4}$ cell dilution were plated on SC-H plates and rich media (YPD), respectively. Colonies were counted after growth at 30° C. for 60 hours. The frequency of His$^+$ cells was calculated by dividing the colony number on SC-H plates by the product of the colony number on YPD plates and the dilution factor.

In some experiments, yeast cells carrying Ty5 plasmids were grown as patches on SC-U medium with galactose at 23° C. for two days. Cells were scraped and resuspended in 1 ml of sterile water. For each patch, 100 μl of a 10$^7$-fold dilution of the cell suspension was plated on nonselective plates (YPD) to calculate total cell number. 100 μl of a 10-fold dilution was spread on selective media (SC without histidine, SC-H). His$^+$ colonies were replicated to SC-H medium with 5-FOA (SC-H+FOA) to remove plasmid recombinants. The frequency of Ty5 transposition was calculated by dividing the cell number on SC-H+FOA plates by that on YPD plates and the dilution factor. The yeast strain W303-1A (MATa ade2-1 can1-100 his3-11 leu2-3 trp1-1 ura3-1), W303-1B, and their derivatives were used for all manipulations. The MATα locus was converted to MATa for all parental yeast strains (provided by Daniel Gottschling, Jasper Rine, David Shore and Rolf Sternglanz). All strains have the plasmid pNK254, which carries a Ty5 element with the his3AI selectable marker under transcriptional control of the GAL1-10 promoter.

To physically characterize de novo Ty5-6p insertions, His$^+$ cells resulting from transposition assays were grown on 5-Fluoroorotic acid plates (Ausubel et al. 1987) to lose the URA3-based plasmid, pSZ152 (Ausubel et al. 1987). Genomic DNA was isolated from four His$^+$/Ura$^-$ strains. Approximately 1 mg of this DNA was digested with XhoI, separated on 0.8% agarose gels and transferred to nylon membranes by the alkaline method (Ausubel et al. 1987). Filters were hybridized with $^{32}$P-labeled HIS3 sequences to identify candidate transposition events. One such event was cloned by screening a partial genomic library constructed from a His$^+$/Ura$^-$ strain by methods previously described (Zou et al. 1995). Flanking sequences from both sides of the Ty5-6p insertion were determined using oligonucleotides DVO200 (CATTACCCATATCATGCT) (SEQ ID NO:10) and DVO183 (CCTCGAGCAGCAAACCTCCGA) (SEQ ID NO:26).

Example 6
Chromosome Analysis of Ty5 Insertions

To investigate the chromosome distribution of the de novo Ty5-6p insertions, 148 individual His$^+$/Ura$^-$ colonies were recovered from transposition assays with ySZ135 (W303-1A carrying pSZ152). Chromosomes were prepared in low melting agarose plugs, separated in pulsed-field gels using standard conditions (Bio-Rad Laboratories, Hercules, Calif.), transferred to nylon membranes and hybridized with a $^{32}$P-labeled HIS3-specific probe.

Example 7
PCR Analysis

Unless otherwise specified, each PCR reaction included 50 ng of genomic DNA from ten His+ strains, representing ten independent Ty5 transposition events. Insertions near transcriptional silencers were identified and confirmed by two rounds of PCR. In strains with HMR-E mutations, the first round of PCR used primers that amplified all Ty5 insertions near HMR-E. This was accomplished using a Ty5-specific primer (DVO200, 5'-CATTACCCATATCATGCT-3') (SEQ ID NO:10) and two primers that amplified a 2.3 kb window flanking HMR-E (DVO211, 5'-TGGTAGAAGCAGTAGTAACT-3' (SEQ ID NO:11); DVO212,5'-ACCAGAGAGTGTAACAACAG-3') (SEQ ID NO:12). Since DNA from at least one of the ten strains in each reaction did not have an insertion near HMR-E, the presence of the 2.3 kb band served as a control for the PCR reactions. One of the PCR primers (DVO212) also matched sequences flanking HML-E, and therefore Ty5 insertions in one orientation were recovered at this silencer. The second round of PCR amplification used silencer-specific primers to precisely map sites of integration. For HMR-E, these were DVO211, DVO200 and DVO220 (5'-CTGTGTACAAGAGTAGTACC-3') (SEQ ID NO:13); for HML-E these were DVO247 (5'-CACGAGCTCATCTAGAGCC-3') (SEQ ID NO:14) and DVO220.

The amplifications were performed for 30 cycles using the following program: 94° C. for 1 min, 50° C. for 2 mins and 72° C. for 5 mins. Amplification was followed by a final extension step at 72° C. for 5 mins. To map insertions in strains with SIR1–SIR4 deletions, a similar two-round PCR strategy was used. The first round of PCR used primers to amplify insertions near HMR-E (DVO211; DVO212; DVO200), HML-E (DVO247; DVO212; DVO200), HML-1 (DVO251; 5'-TGCTGAAGTACGTGGTGAC-3' (SEQ ID NO:15); DVO252, 5' TTCTCGAAGTAAGCATCAAC-3' (SEQ ID NO:19; DVO200) and HMR-1 (DVO251; DVO253, 5'-AGCCCTATTCGCGTCGTG 3' (SEQ ID NO:16); DVO200). The second round used a single silencer specific primer (DVO211, HMR-E; DVO247, HML-E; DVO252, HML-1; DVO253, HMR-1) as well as two primers specific to Ty5 (DVO200; DVO220).

Example 8
Mapping Ty5 Insertions onto Chr III

Genomic DNA was isolated from W303-1A strains with a Ty5 insertion on chr III. For nine strains, sequences flanking the Ty5 insertion were determined by inverse PCR. Approximately 100 ng of genomic DNA was digested with the restriction enzyme MspI in 20 ml. The digestion products were then ligated in 50 μl at 15° C. overnight to promote self-ligation. The ligation mixture (2 μl) was amplified with the Ty5-6p LTR-specific oligonucleotides DVO219 (TACTGTCGGATCGGAGGTTT) (SEQ ID NO:17) and DVO220 (CTGTGTACAAGAGTAGTACC) (SEQ ID NO:13). For the remaining strains, sequences flanking the Ty5 insertions were amplified by standard PCR. LTR-specific primers (DVO219 or DVO220) were used in conjunction with oligonucleotides flanking the transcriptional silencer HMR-E, HMR-I, HML-E and HML-I, as well as chr III sub-telomeric X repeats. These latter oligonucleotides were: DVO211 (TGGTAGAAGCAGTAGTAACT) (SEQ ID NO:11) and DVO212 (ACCAGAGAGTGTAACAACAG) (SEQ ID NO:12) for HMR-E; DVO251 (TGCTGAAGTACGTGGTGAC) (SEQ ID NO:15) and DVO253 (AGCCCTATTCGCGTCGTG) (SEQ ID NO:16) for HMR-I; DVO247 (CACGAGCTCATCTAGAGCC) (SEQ ID NO:14) or DVO250 (GCCTCTCCTTCTAAGAAGAT) (SEQ ID NO:18) and DVO212 for HML-E; DVO251 and DVO252 (TTCTCGAAGTAAGCATCAAC) (SEQ ID NO:19) for HML-I. Note that DVO212 and DVO251 are complementary to sequences shared by HMR, HML and MAT. The oligonucleotides DVO213 [TAGAATATTTTTATGTTTAG (G/C)TGA(T/G) TTT] (SEQ ID NO:20) and DVO254 [AAA(C/A)TCA(C/G)CTAAACATAAAAATATTCTA) (SEQ ID NO:21) match the ACSs in both the left and right chr III sub-telomeric X repeats. Sequences flanking Ty5 insertions were determined with oligonucleotides DVO214 (CCCTCGAGCATTTACATAACATATAGAAAG) (SEQ ID NO:22) or DVO243 (CCTTGTCTAAAACATTACTG) (SEQ ID NO:23). Ty5 insertion sites were determined by comparing the flanking sequences to the *S. cerevisiae* genome database.

Example 9

Identification of Promoters Expressed in Heterochromatin

A functional, transpositionally active Ty5-6p element is placed under the regulatory control of a regulated promoter, e.g., GAL10, so that transcription and transposition can be controlled. A promoterless neomycin phosphotransferase gene (neo) is inserted into a unique ClaI site engineered into the Ty5-6p derivative between the end of the ORF and the 3' LTR. The neo gene confers G148 resistance to plant, animal and fungal (including yeast) cells. The neo coding sequence is cloned in the orientation opposite that of the Ty5-6p ORF, and carries an artificial intron that disrupts neo expression unless spliced from the retrotransposon mRNA. Neo gene expression, therefore, requires transposition by reverse transcription. Site-directed mutagenesis is used to remove the BamHI site naturally present in Ty5-6p without changing the encoded amino acid sequence of the Ty5-6p ORF. A unique BamHI site is then introduced immediately upstream of the translation start site of the neo coding sequence. This modified Ty5-6p derivative (termed Ty5-6pIA herein) is cloned into the appropriate vector for introduction into the host of choice (pRS426 for yeast, pBIN19 for plants, and so on as readily apparent to the ordinary skilled artisan). A genomic DNA library is constructed by partially digesting purified DNA with Sau3A or MboI and cloning into the engineered unique BamHI site of the modified Ty5-6pIA on the vector of choice. Transposition in the desired eukaryotic host cell, tissue or organism is selected. G418 resistant cells (or tissue or organisms) are selected; most carry the Ty5-6p derivative in silent chromatin (heterochromatin) and express the neo coding sequence from the heterologous Sau3A or MboI DNA fragment. Promoters which are resistant to silencing are then characterized from the antibiotic resistant cells into which the Ty5-6p derivative has been identified as transposed into silent chromatin.

Example 10

DNA Manipulations and Analysis

Yeast genomic DNA and chromosomes were prepared as described (Ausubel et al. 1987). Genomic DNA was digested with restriction enzymes and separated by agarose gel electrophoresis. Yeast chromosomes were separated by pulsed-field gel electrophoresis, and chromosome identity determined by their mobility (Louis et al. 1994). Gels containing genomic DNA or chromosomes were transferred to nylon membranes by alkaline transfer. Filters were hybridized with DNA fragments that had been radio-labeled by random-priming (Promega, Madison, Wis.). Hybridization probes included Ty5 internal sequences (probe A and B in FIG. 3A), the long terminal repeat (LTR) (FIG. 3A), as well as sequences flanking Ty5 insertions. The LTR was amplified from Ty55p with oligonucleotides DVO182 (5'-GGGTAATGTTTCAGT-3') (SEQ ID NO:5) and DVO116 (5'TAGTAAGTTTATTGGACC-3') (SQ ID NO:24). Sequence flanking the 5' end of Ty5-12p element was amplified with DVO200 (5'-CATTACCCATATCATGCT-3') (SEQ ID NO:10) and the reverse primer, which is complementary to the vector. DNA sequences were determined with the FMOL SEQUENCING KIT (Promega), or by the Nucleic Acid Facility of Iowa State University. Sequence analysis was performed using the GCG computer programs (Devereux et al. 1984). LTR sequences were identified from the complete nucleotide sequence of *S. cerevisiae* using the program BLAST (Altschul et al. 1990). Sequences were considered that had more than 65% nucleotide identity to the Ty5-1 left LTR.

REFERENCES

Altschul, S., Gish, W., Miller, W., Myers, E., and Lipman, D. (1990) *J. Molec. Biol.* 215:403–410

Ausubel, F. M., R. Brent, R. E. Kingston, D. D. Moore, J. G. Seidman, J. A. Smith, and K. Struhl. 1987. *Current Protocols in Molecular Biology*. Greene/Wiley Interscience, New York.

Atwood, A., J. Lin, and H. L. Levin. 1996. The retrotransposon Tf1 assembles VLPs that contain excess gag relative to integrase due to a regulated degradation process. *Mol. Cell. Biol.* 16:338–346.

Bell, S. P., R. Kobayashi, and B. Stillman. 1993. Yeast origin recognition complex functions in transcription silencing and DNA replication. *Science* 262:1844–1849.

Biessmann, H., J. M. Mason, K. Ferry, M. d'Hulst, K. Valgeirsdottir, K. L. Traverse, and M. L. Pardue. 1990. Addition of telomere-associated HeT DNA sequences "heals" broken chromosome ends in Drosophila. *Cell* 61:663–673.

Blackburn, E. 1992. *Annu. Rev. Biochem.* 61:113–129.

Boeke, J. D., D. J. Garfinkel, C. A. Style, and G. R. Fink. 1985. Ty elements transpose through an RNA intermediate. *Cell* 40:491–500.

Boeke, J. D., H. Xu, G. R. Fink. 1988. A general method for the chromosomal amplification of genes in yeast. *Science* 239:280–282.

Boeke, J. D., and S. B. Sandmeyer. 1991. Yeast transposable elements. In *The Molecular and Cellular Biology of the Yeast Saccharomyces* (ed. J. R. Broach, J. R. Pringle, and E. W. Jones), pp. 193–261. Cold Spring Harbor Laboratory Press, Cold Spring Harbor, N.Y.

Brand, A. H., L. Breeden, J. Abraham, R. Sternglanz, and K. Nasmyth. 1985. Characterization of a "silencer" in yeast: a DNA sequence with properties opposite to those of a transcriptional enhancer. *Cell* 41:41–48.

Brown, C. J., B. D. Hendrich, J. L. Rupert, R. G. Lafreniere, Y. Xing, J. Lawrence, Willard. 1992. The human XIST gene: analysis of a 17 kb inactive X-specific R that contains conserved repeats and is highly localized within the nucleus. *Cell* 71:527–542.

Brown, P., and H. Varmus. 1989. Retroviruses. In Mobile DNA (ed. D. E. Berg and M. M. Howe), pp. 53–108. American Society for Microbiology, Washington, D.C.

Bryan, T. M., A. Englezou, J. Gupta, S. Bacchetti, and R. R. Reddel. 1995. Telomere elongation in immortal human cells without detectable telomerase activity. *EMBO J.* 14:4240–4248.

Chalker, D. L., and S. B. Sandmeyer. 1990. Transfer RNA genes are genomic targets for de novo transposition of the yeast retrotransposon Ty3. *Genetics* 126:837–850.

Chalker, D. L., and S. B. Sandmeyer. 1992. Ty3 integrates within the region of RNA polymerase III transcription initiation. *Genes & Dev.* 6:117–128.

Chan, C. S. M. and Tye, G.-K. 1983. *Cell* 33:563–573.

Chapman, K. B., A. S. Bystrom, and J. D. Boeke. 1992. Initiator methionine tRNA is essential for Ty1 transposition in yeast. *Proc. Natl. Acad. Sci. USA* 89:3236–3240.

Craigie, R. 1992. Hotspots and warm spots: integration specificity of retroelements. *Trends Genet.* 8:187–190.

Curcio, M. J., and D. J. Garfinkel. 1991. Single-step selection for Ty1 element retrotransposition. *Proc. Natl. Acad. Sci. USA* 88:936–940.

Devereux, J., P. Haeberli, and O. Smithies. 1984. A comprehensive set of sequence analysis programs for the VAX. *Nucl. Acids Res.* 12:387–395.

Devine, S. E., and J. D. Boeke. 1995. Integration of the yeast retrotransposon Ty1 is targeted to regions upstream of genes transcribed by RNA polymerase III. *Genes & Dev* (in press).

Diffley, J. F. X., and B. Stillman. 1988. Purification of a yeast protein that binds to origins of DNA replication and a transcriptional silencer. *Proc. Natl. Acad. Sci. USA* 85:2120–2124.

Dujon, B., Alexandraki, D., Andre, B., Ansorge, W., Baladron, V., Vallesta, J. P., Banrevi, A., Bolle, P. A., Bolokin-Fukuhara, M., Bossier, P. and et al. (1994) *Nature* 369:371–378.

Foss, M., F. J. McNally, P. Laurenson, and J. Rine. 1993. Origin recognition complex (ORC) in transcriptional silencing and DNA replication in *S. cerevisiae. Science* 262:1838–1844.

Gottschling, D. E., O. M. Aparicio, B. L. Billington, and V. A. Zakian. 1990. Position effect at *S. cerevisiae* telomeres: reversible repression of Pol II transcription. *Cell* 63:751–762.

Gromodka, R., Gora, M., Zielenkiewicz, U., Slonimski, P. and Rytka, J. 1996 *Yeast* 12:583–591.

Haber, J. E. 1992. Mating-type gene switching in *Saccharomyces cerevisiae. Trends Genet.* 8:446–452.

Hardy, C. F., L. Sussel, and D. Shore. 1992. A RAP1-interacting protein involved in transcriptional silencing and telomere length regulation. *Genes & Dev.* 6:801–814.

Hecht, A., T. Laroche, S. Strahl-Bolsinger, S. M. Gasser, and M. Grunstein. 1995. Histone H3 and H4 N-termini interact with SIR3 and SIR4 proteins: a molecular model for the formation of heterochromatin in yeast. *Cell* 80:583–592.

Hull, M. W., J. Erickson, M. Johnston, and D. R. Engelke. 1994. tRNA genes as transcriptional repressor elements. *Mol. Cell. Biol.* 14:1266–1277.

Jacks, T. 1990. Translational suppression in gene expression in retroviruses and retrotransposons. *Curr. Top. Microbiol. Immunol.* 157:93–124.

Ji, H., D. P. Moore, M. A. Blomberg, L. T. Braiterman, D. F. Voytas, G. Natsoulis, and J. D. Boeke. 1993. Hotspots for unselected Ty1 transposition events on yeast chromosome III are near tRNA genes and LTR sequences. *Cell* 73:1007–1018.

Kalpana, G. V., S. Marmon, W. Wang, G. R. Crabtree, and S. P. Goff. 1994. Binding and stimulation of HIV-1 integrase by a human homolog of yeast transcription factor SNF5. *Science* 266:2002–2006.

Karpen, G. H., and A. C. Spradling. 1992. Analysis of subtelomeric heterochromatin in the Drosophila minichromosome Dp1187 by single P element insertional mutagenesis. *Genetics* 132:737–753.

Kayne, P. S., U. J. Kim, M. Han, J. R. Mullen, F. Yoshizaki, and M. Grunstein. 1988. Extremely conserved histone H4 N terminus is dispensable for growth but essential for repressing the silent mating loci in yeast. *Cell* 55:27–39.

Keeney, J. B., K. B. Chapman, V. Lauermann, D. F. Voytas, S. U. Astrom, U. von Pawel-Rammingen, A. Bystrom, and J. D. Boeke. 1995. Multiple Molecular Determinants for Retrotransposition in a Primer tRNA. *Mol. Cell. Biol.* 15:217–226.

Kikuchi, Y., Y. Ando, and T. Shiba. 1986. Unusual priming mechanism of RNA-directed DNA synthesis in copia retrovirus-like particles of Drosophila. *Nature* 323:824–826.

Kirchner, J., C. M. Connolly, and S. B. Sandmeyer. 1995. Requirement of RNA polymerase III transcription factors for in vitro position-specific integration of a retroviruslike element. *Science* 267:1488–1491.

Kurtz, S., and D. Shore. 1991. RAP1 protein activates and silences transcription of mating-type genes in yeast. *Genes & Dev.* 5:616–628.

Laurenson, P., and J. Rine. 1992. Silencers, silencing, and heritable transcriptional states. *Microbiol. Rev.* 56:543–560.

Levin, H. L., D. C. Weaver, and J. D. Boeke. 1990. Two related families of retrotransposons from *Schizosaccharomyces pombe. Mol. Cell. Biol.* 10:6791–6798.

Levis, R. W., R. Ganesan, K. Houtchens, L. A. Tolar, and F. M. Sheen. 1993. Transposons in place of telomeric repeats at a *Drosophila* telomere. *Cell* 75:1083–1093.

Longtine, M. S., S. Enomoto, S. L. Finstad, and J. Berman. 1993. Telomere-mediated plasmid segregation in *Saccharomyces cerevisiae* involves gene products required for transcriptional repression at silencers and telomeres. *Genetics* 133:171–182.

Loo, S., and J. Rine. 1994. Silencers and domains of generalized repression. *Science* 264:1768–1771.

Louis, E. (1995) *Yeast* 11:1553–1573.

Louis, E. J. and Haber, J. E. 1992. *Genetics* 131:559–574.

Louis, E. J., E. S. Naumova, A. Lee, G. Naumov, and J. E. Haber. 1994. The chromosome end in yeast: its mosaic nature and influence on recombinational dynamics. *Genetics* 136:789–802.

Lundblad, V., and E. H. Blackburn. 1993. An alternative pathway for yeast telomere maintenance rescues est1-senescence. *Cell* 73:347–360.

Micklem, G., A. Rowley, J. Harwood, K. Nasmyth, and J. F. Diffley. 1993. Yeast origin recognition complex is involved in DNA replication and transcriptional silencing. *Nature* 366:87–89.

P. Moretti, K. Freeman, L. Coodly, D. Shore. 1994. *Genes Dev.* 8:2257–2269.

Mount, S. M., and G. M. Rubin. 1985. Complete nucleotide sequence of the Drosophila transposable element copia: homology between copia and retroviral proteins. *Mol. Cell. Biol.* 5:1630–1638.

Mullen, J. R., P. S. Kayne, R. P. Moerschell, S. Tsunasawa, M. Gribskov, M. Colavito-Shepanski, M. Grunstein, F. Sherman, and R. Sternglanz. 1989. Identification and characterization of genes and mutants for an N-terminal acetyltransferase from yeast. *EMBO J.* 8:2067–2075.

Ochman, H., A. S. Gerber, and D. L. Hartl. 1988. Genetic applications of an inverse polymerase chain reaction. *Genetics* 120:621–623.

Oliver, S. G., Q. J. M. van der Aart, M. L. Agostoni-Carbone, M. Aigle, L. Alberghina, D. Alexandraki, G.

Antoine, R. Anwar, and et al. 1992. The complete DNA sequence of yeast chromosome III. *Nature* 357:38–46.

Pimpinelli, S., M. Berloco, L. Fanti, P. Dimitri, S. Bonaccorsi, E. Marchetti, R. Caizzi, C. Caggese, and M. Gatti. 1995. Transposable elements are stable structural components of *Drosophila melanogaster* heterochromatin. *Proc. Natl. Acad. Sci. USA* 92:3804–3808.

Rine, J., and I. Herskowitz. 1987. Four genes responsible for a position effect on expression from HML and HMR in *Saccharomyces cerevisiae. Genetics* 116:9–22.

Roth, S. 1995. Chromatin-mediated transcriptional repression in yeast. *Curr. Opin. Genet. Dev.* 5:168–173.

Rymond, B. C. and M. Rosbash. 1992. Yeast pre-mRNA splicing. In *The Molecular and Cellular Biology of the Yeast Saccharomyces* (ed. J. R. Broach, J. R. Pringle, and E. W. Jones), pp. 143–192. Cold Spring Harbor Laboratory Press, Cold Spring Harbor, N.Y.

Sandmeyer, S. B., L. J. Hansen, and D. L. Chalker. 1990. Integration specificity of retrotransposons and retroviruses. *Annu. Rev. Genet.* 24:491–518.

SanMiguel, P. et al. 1996. *Science* in press.

Sharon, G., T. J. Burkett, and D. J. Garfinkel. 1994. Efficient homologous recombination of Ty1 element cDNA when integration is blocked. *Mol. Cell. Biol.* 14:6540–6551.

Thompson, J. S., X. Ling, and M. Grunstein. 1994. Histone H3 amino terminus is required for telomeric and silent mating locus repression in yeast. *Nature* 369:245–247.

Voytas, D. F., and F. M. Ausubel. 1988. A copia-like transposable element family in *Arabidopsis thaliana. Nature* 336:242–244.

Voytas, D. F., and J. D. Boeke. 1992. Yeast retrotransposon revealed. *Nature* 358:717.

Voytas, D. F., and J. D. Boeke. 1993. Yeast retrotransposons and tRNAs. *Trends Genet.* 9:421–427.

Weinstock, K. G., M. F. Mastrangelo, T. J. Burkett, D. J. Garfinkel, and J. N. Strathern. 1990. Multimeric arrays of the yeast retrotransposon Ty1. *Mol. Cell. Biol.* 10:2882–2892.

Xiong, Y., and T. H. Eickbush. 1990. Origin and evolution of retroelements based upon their reverse transcriptase sequences. *EMBO J.* 9:3353–3362.

Yoshioka, K., H. Honma, M. Zushi, S. Kondo, S. Togashi, T. Miyake, and T. Shiba. 1990. Virus-like particle formation of *Drosophila copia* through autocatalytic processing. *EMBO J.* 9:535–541.

Zou, S., D. A. Wright, and D. F. Voytas. 1995. The Saccharomyces Ty5 retrotransposon family is associated with origins of DNA replication at the telomeres and the silent mating locus HMR. *Proc. Natl. Acad. Sci. USA* 92:920–924.

TABLE 1

The distribution of 87 independent de novo Ty5 transposition events among *S. cerevisiae* chromosomes.

| Chromosome(s) | Number of insertions | Density of insertions per kb |
|---|---|---|
| III | 26 | 1/12 |
| I/VI | 10 | 1/51 |
| IX | 5 | 1/88 |
| XI | 5 | 1/133 |
| II/X | 11 | 1/140 |
| VII/XV | 14 | 1/164 |
| IV | 7 | 1/234 |
| XVI/XIII | 8 | 1/244 |
| V/VIII | 1 | 1/1100 |

TABLE 2

Locations of de novo Ty5 transposition events on chr III

| Ty5 insertion number | Locus | Nucleotide position on chr III | Target site sequence | Distance to closest ACS |
|---|---|---|---|---|
| W2 | Left telomere | 625 | GAAAC | 413 |
| W84 | Left telomere | 798 | CTCAC | 240 |
| W77 | Left telomere | 853 | TATAC | 185 |
| W55 | Left telomere | 1842 ± 50 | ND | 850 ± 50 |
| W28 | HML-E | 10499 | ATTAC | 747 |
| W7 | HML-E | 11786 | TATTT | 531 |
| W144 | HML-E | 11797 | CCATG | 542 |
| Wii4 | HML-I | 13584 | GTTTG | 1104 |
| Wi34 | HML-I | 13783 | CATTT | 905 |
| W79 | HML-I | 13911 | TATAC | 788 |
| W68 | HML-I | 14164 | TGTTC | 535 |
| W147 | Ty1 hot spot | 147535 ± 50 | ND | ND |
| W9 | HMR-E | 290076 | AACGT | 1291 |
| W113 | HMR-E | 290843 | CTTAC | 525 |
| W76 | HMR-E | 291467 | AATTC | 87 |
| W66 | HMR-E | 291541 | GAAAG | 162 |
| W44 | HMR-I | 293675 | GAATT | 58 |
| W27 | HMR-I | 293674 | GGAAT | 57 |
| W51 | HMR-I | 293723 | GTTGG | 106 |

TABLE 3

The frequency of Ty5 transpouition near HML-E and HMR-E.

| HMR-E allele | Strain | Total Ty5 insertions | Insertions near HML-E (percent) | Insertions near HMR-E (percent) | Fold reduction in targeting to HML-E1 | Fold reduction in targeting to HMR-E[1] |
|---|---|---|---|---|---|---|
| A-E-B | ySZ202 | 908 | 20 (2.2%) | 17 (1.9%) | 1 | 1 |
| ΔA-E-B | ySZ225 | 884 | 14 (1.6%) | 6 (0.68%) | 1.4 | 2.8* |
| A-ΔE-B | ySZ227 | 828 | 21 (2.5%) | 4 (0.48%) | 0.87 | 3.9** |
| A-E-ΔB | ySZ226 | 788 | 8 (1.0%) | 8 (1.0%) | 2.2 | 1.8 |
| A-ΔE-ΔB | ySZ222 | 883 | 18 (2.0%) | 0 (<0.11%) | 1.1 | >17*** |
| ΔA-E-ΔB | ySZ228 | 672 | 6 (0.80%) | 0 (<0.15%) | 2.5* | >13*** |

TABLE 3-continued

The frequency of Ty5 transpouition near HML-E and HMR-E.

| HMR-E allele | Strain | Total Ty5 insertions | Insertions near HML-E (percent) | Insertions near HMR-E (percent) | Fold reduction in targeting to HML-E1 | Fold reduction in targeting to HMR-E[1] |
|---|---|---|---|---|---|---|
| ΔA-ΔE-B | ySZ224 | 754 | 6 (0.80%) | 0 (<0.13%) | 2.8* | >14*** |
| ΔA-ΔE-ΔB | ySZ221 | 954 | 8 (0.84%) | 0 (<0.10%) | 2.6* | >18*** |

[1]Marked numbers are significantly different from the wild type at *$P < 0.05$, $P < 0.01$ and *$P < 0.001$.

TABLE 4

The frequency of Ty5 transposition near the HM silencers in strains with deletions in SIR genes.

| SIR Genotype | Strain | Total Ty5 insertions | Insertions near HM silencers | Percentage of insertions near HM silencers[1] | Fold reduction in targeting to HM silencers[1] |
|---|---|---|---|---|---|
| wild type | ySZ201 | 200 | 12 | 6% | — |
| Δsir1 | ySZ198 | 200 | 5 | 2.5% | 2.4 |
| Δsir2 | ySZ208 | 210 | 3 | 1.4% | 4.3* |
| Δsir3 | ySZ212 | 340 | 2 | 0.59% | 10*** |
| Δsir4 | ySZ232 | 230 | 0 | <0.43% | >14*** |

[1]Marked numbers are significantly different from the wild type at *$P < 0.05$, $P < 0.01$ and *$P < 0.001$.

TABLE 5

Sequences of Ty5 target sites.

| Species | Insertion (chr) | Left target sequence | Right target sequence | Target nucleotide identity | LTR nucleotide identity[1] |
|---|---|---|---|---|---|
| S. cerevisiae | Ty5–1 (III) | TTTCA | TATCC | 3/5 | 86%, 89% |
| | Ty5–2 (III) | TTCCT | TAAAA | 1/5 | 73% |
| | Ty5–3 (III) | ATCGC | TTTGC | 3/5 | 55% |
| | Ty5–7 (XI) | CGTTG | TACCG | 1/5 | 82% |
| | Ty5–8 (VIII) | GTATA | ATATG | 3/5 | 77% |
| | Ty5–15 (VII) | TTTCA | CCCAA | 1/5 | 81% |
| | Ty5–16 (V) | GTTAT | GTTCT | 4/5 | 91% |
| | Ty5–17 (V) | GTTCT | TTACA | 2/5 | 73% |
| S. paradoxus | Ty5–6p (XI) | TCGTA | TCGTA | 5/5 | 100% |
| | Ty5–5p (III/XI) | TGTCA | CTATC | 0/5 | 100%, 98% |
| | Ty5–10p (III/XI) | AGTAT | TATAA | 2/5 | 98% |
| | Ty5–12p (III/XI) | AGTAT | TTTTC | 1/5 | 97% |
| | Ty5–14p (ND) | — | TGTCA | — | 98% |

[1]Values are derived from comparisons with the Ty5–6p right LTR. Multiple values refer to comparisons with the left and right LTRs, respectively.

We claim:

1. A nonnaturally occurring DNA molecule comprising a retrotransposon selected from the group consisting of Ty5-6p and derivatives thereof which retrotranspose.

2. The nonnaturally occurring DNA molecule of claim 1 wherein said retrotransposon is Ty5-6p and has a nucleotide sequence as given in SEQ ID NO:1.

3. A method of regulating lifespan of a yeast cell which expresses an HO endonuclease, said method comprising the steps of:
   (a) transforming or transfecting said host yeast cell to contain a nonnaturally occurring DNA molecule of claim 1, wherein the retrotransposon has been modified to insert an HO endonuclease recognition site;
   (b) incubating the transformed or transfected yeast host cell prepared in step (a) under conditions allowing the retrotransposon to insert itself into a telomeric region of the genome;
whereby insertions of the retrotransposon in the genome result in enzymatic cleavage at the HO endonuclease recognition site within the retrotransposon in the telomeric region of a chromosome within the genome of said yeast host cell, with the result that the lifespan of said cell is shortened.

4. The nonnaturally occurring DNA molecule of claim 1 wherein said retrotransposon is Ty5-6p into which a DNA segment heterologous to Ty5-6p has been inserted.

5. The nonnaturally occurring DNA molecule of claim 4 wherein transposition in a host cell galactose.

6. A method of directing heterologous DNA to a silent region, subtelomeric region or a telomeric region of a yeast host cell chromosome, said method comprising the steps of:
   (a) transforming or transfecting said yeast host cell to contain the nonnaturally occurring DNA molecule of claim 1;
   (b) incubating the transformed or transfected yeast host cell prepared in step (a) under conditions allowing the retrotransposon to insert itself into a chromosome of said yeast host cell wherein the heterologous DNA is directed to a silent region, subtelomeric region or telomeric region of a yeast host cell chromosome.

7. The method of claim 6 wherein said heterologous DNA is targeted to the telomeric region of a yeast host cell chromosome.

8. The method of claim 6 wherein the silent region is a mating type locus.

9. The method of claim 6 wherein said retrotransposon is a Ty5-6p into which a selectable marker has been incorporated.

10. The method of claim 9 wherein the selectable marker is a histidine biosynthetic gene.

11. A method of identifying regions of a genome bound in silent chromatin or regions of the genome in chromatin-like silent chromatin, in a yeast host cell, wherein genes in these regions are regulated by the silent chromatin, said method comprising the steps of:

(a) transforming or transfecting said yeast host cell to contain the nonnaturally occurring DNA molecule of claim 1;

(b) incubating the transformed or transfected yeast host cell prepared in step (a) under conditions allowing the retrotransposon to insert itself into a chromosome of said yeast host cell, wherein regions of a genome bound in silent chromatin or regions of the genome in chromatin-like silent chromatin, in a yeast host cell, wherein genes in these regions are regulated by the silent chromatin, are identified.

12. The method of claim 11 wherein said retrotransposon comprises a marker gene.

13. The method of claim 11 wherein said regions of the genome bound in silent chromatin or regions of the genome like silent chromatin comprise genes involved in senescence.

* * * * *

UNITED STATES PATENT AND TRADEMARK OFFICE
CERTIFICATE OF CORRECTION

PATENT NO. : 5,976,795

DATED : November 2, 1999

INVENTOR(S) : Voytas and Zou

Figure 11A:
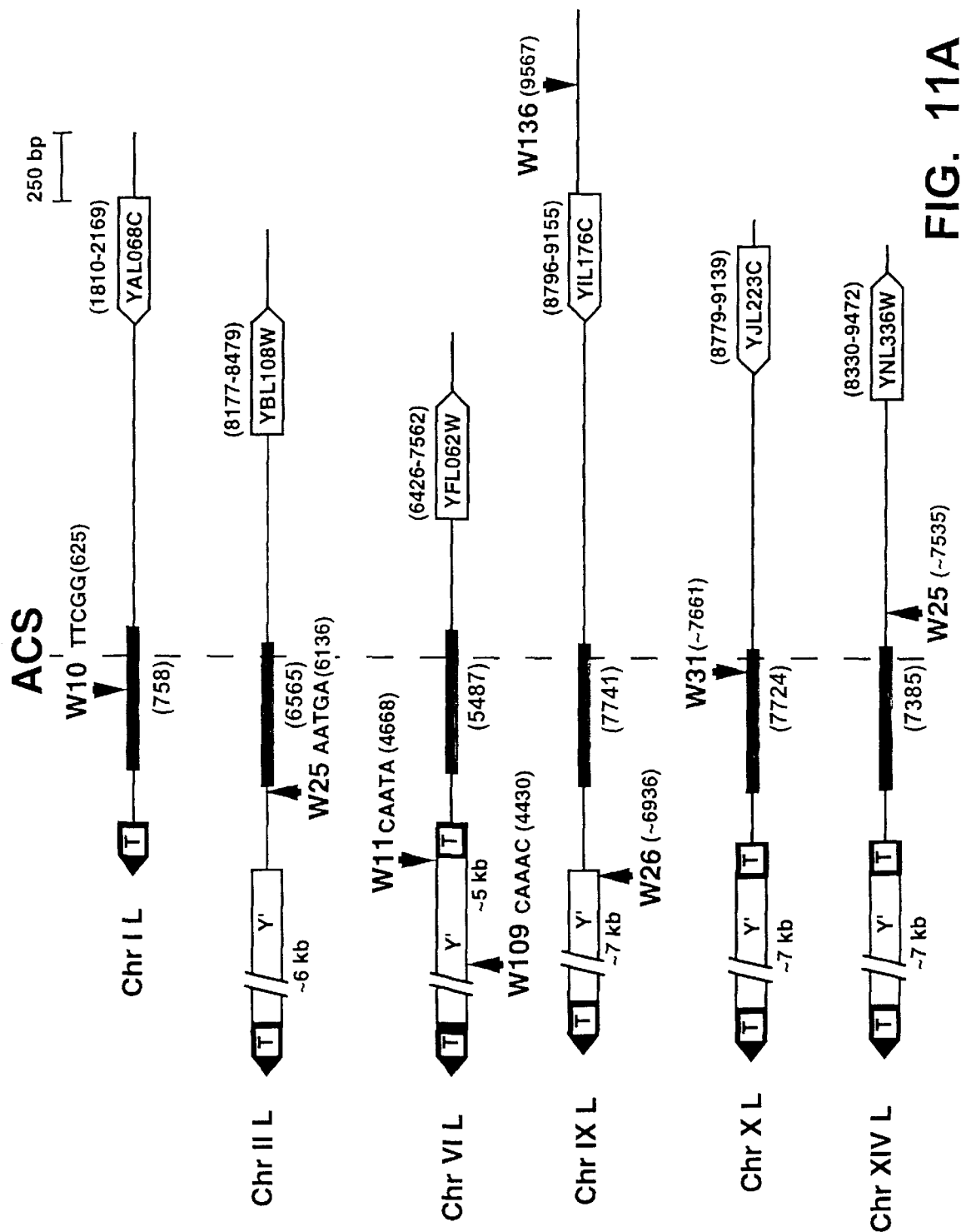
FIG. 11 shows the locations of de novo transposition events. Left and right arms of chromosomes are labeled as L and R, respectively. t indicates telomeric repeat sequences, and the narrow boxes indicate X repeats, which are aligned at the ACS sequences (autonomously replicating consensus sequences). The sizes of Y' elements are provided. Open boxes with arrowheads depict endogenous Ty5 LTRs, and open boxes with labels indicate open reading frames. The Ty5 insertions are labeled as W followed by numbers, referring to the strains from which they were isolated. Arrows pointing down indicate insertions in the same 5' to 3' orientation as the chromosome sequences. Arrows pointing up represent insertions in the opposite orientation. Numbers in parentheses designate base positions of open reading frames and Ty5 insertion sites. The base position of the ACS is provided adjacent to the dashed line, at the position of this sequence.
Figure 11B:
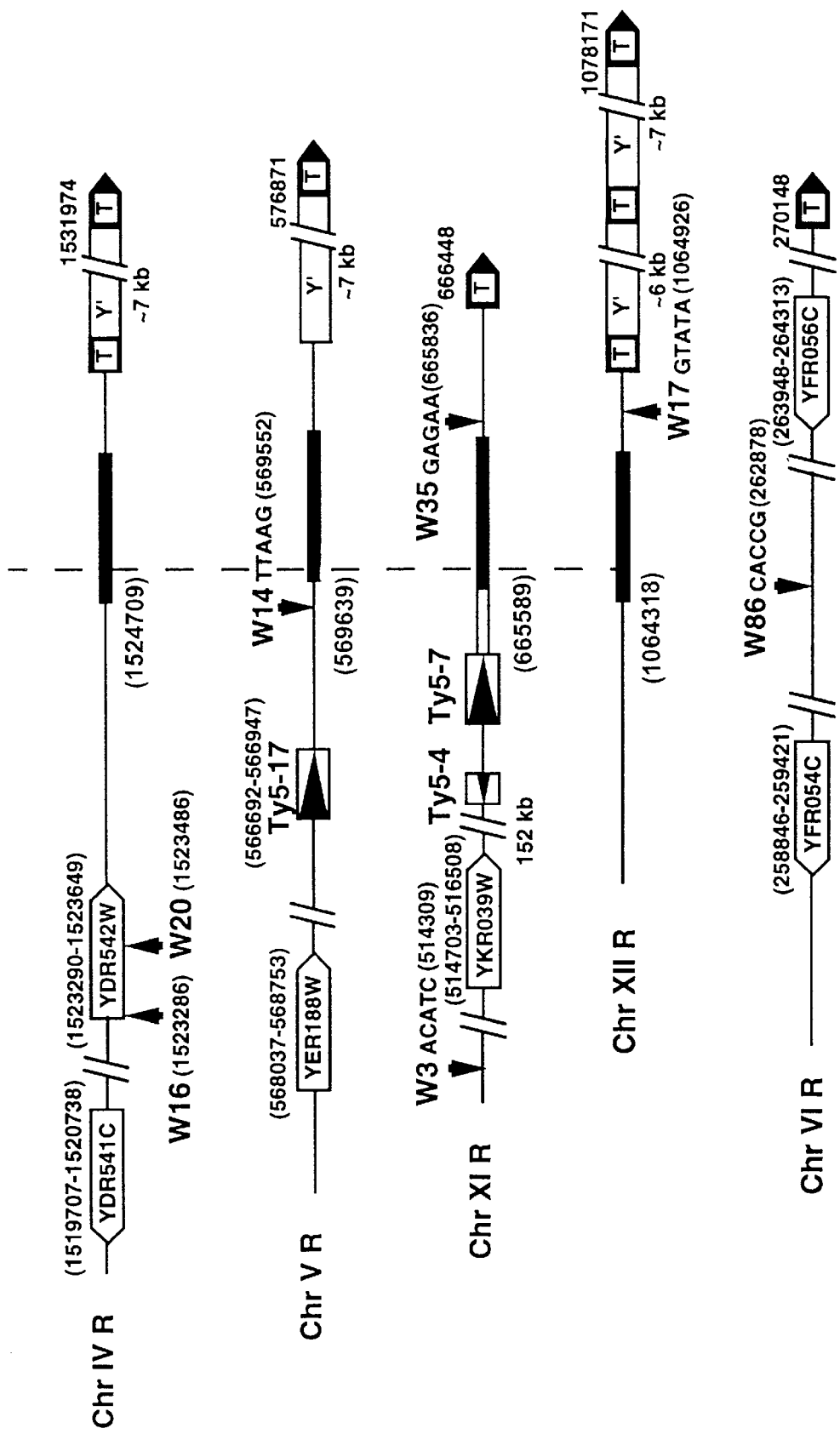

It is certified that error appears in the above-identified patent and that said Letters Patent is hereby corrected as shown below:

In Fig. 1B, under "Protease", the third line down, please delete "Ta1-1" and replace with --Ta1-3--.
In Fig. 6, in the top circle, the "B" in the box should be directly under the "ABF1" in the circle.
In Column 4, line 25, please delete "His$^{30}$" and replace with --His$^+$--.
In Column 4, line 57, please delete "Yα and Yα" and replace with --Yα and Ya--.
In Column 4, line 58, please delete "(a1, a2, a1, a2)" and replace with --(a1, a2, α1, α2)--.
In Column 5, line 15, please delete "Yα and Yα" and replace with --Yα and Ya--.
In Column 5, line 16, please delete "(a1, a2, a1, cc2)" and replace with --(a1, a2, α1, α2)--.
In Column 5, line 31, please delete "FIG. 11 shows" and replace with --FIGS. 11A and 11B show--.
In Column 5, line 59, please delete "FIG. 11." and replace with --FIGS. 11A and 11B.--.
In Column 7, line 66, please delete "5' LM" and replace with --5' LTR--.
In Column 10, line 4, please delete "pSZ1S2" and replace with --pSZ152--.
In Column 11, line 7, please delete "(ACS)" and replace with --(ACS or ARCS)--.
In Column 11, line 65, please delete "MRNA" and replace with --mRNA--.
In Column 13, line 57, please delete "Ty1transposition" and replace with --"Ty1 transposition--.
In Column 14, line 16, please delete "(FIG. 1)." and replace with --(FIGS. 11a and 11b)--.
In Column 15, line 5, please delete "M," and replace with --X1--.
In Column 18, line 37, please delete "and MATa" and replace with --and MATα--.
In Column 19, line 19, please delete "esti" and replace with --est1--.
In Column 19, line 66, please delete "our" and replace with --out--.
In Column 26, line 10, please delete "(SQ" and replace with --(SEQ--.
In Column 30, in Table 2, column 1, line 40, please delete "Wii4" and replace with --W114--.
In Column 30, in Table 2, column 1, line 41, please delete "Wi34" and replace with --W134--.
In Column 53, in the Sequence Listing, under "(2) INFORMATION FOR SEQ ID NO:3:", under
    "(i) SEQUENCE CHARACTERISTICS:", please delete "(A) LENGTH: 21 amino acids" and
    replace with --(A) LENGTH: 22 nucleotides or base pairs--.
In Column 53, in the Sequence Listing, under "(2) INFORMATION FOR SEQ ID NO:4:", under
    "(i) SEQUENCE CHARACTERISTICS:", please delete "(A) LENGTH: 22 amino acids" and
    replace with --(A) LENGTH: 23 nucleotides--.

UNITED STATES PATENT AND TRADEMARK OFFICE
CERTIFICATE OF CORRECTION

PATENT NO. : 5,976,795

DATED : November 2, 1999

INVENTOR(S) : Voytas and Zou

It is certified that error appears in the above-identified patent and that said Letters Patent is hereby corrected as shown below:

In Column 53, in the Sequence Listing, under "(2) INFORMATION FOR SEQ ID NO:5:", under
  "(i) SEQUENCE CHARACTERISTICS:", please delete "(A) LENGTH: 14 amino acids" and
  replace with --(A) LENGTH: 15 nucleotides--.
In Column 55, in the Sequence Listing, under "(2) INFORMATION FOR SEQ ID NO:6:", under
  "(i) SEQUENCE CHARACTERISTICS:", please delete "(A) LENGTH: 16 amino acids" and
  replace with --(A) LENGTH: 17 nucleotides--.
In Column 55, in the Sequence Listing, under "(2) INFORMATION FOR SEQ ID NO:7:", under
  "(i) SEQUENCE CHARACTERISTICS:", please delete "(A) LENGTH: 23 amino acids" and
  replace with --(A) LENGTH: 24 nucleotides--.
In Column 55, in the Sequence Listing, under "(2) INFORMATION FOR SEQ ID NO:8:", under
  "(i) SEQUENCE CHARACTERISTICS:", please delete "(A) LENGTH: 21 amino acids" and
  replace with --(A) LENGTH: 22 nucleotides--.
In Column 55, in the Sequence Listing, under "(2) INFORMATION FOR SEQ ID NO:9:", under
  "(i) SEQUENCE CHARACTERISTICS:", please delete "(A) LENGTH: 24 amino acids" and
  replace with --(A) LENGTH: 25 nucleotides--.
In Column 57, in the Sequence Listing, under "(2) INFORMATION FOR SEQ ID NO:10:", under
  "(i) SEQUENCE CHARACTERISTICS:", please delete "(A) LENGTH: 17 amino acids" and
  replace with --(A) LENGTH: 18 nucleotides--.
In Column 57, in the Sequence Listing, under "(2) INFORMATION FOR SEQ ID NO:11:", under
  "(i) SEQUENCE CHARACTERISTICS:", please delete "(A) LENGTH: 19 amino acids" and
  replace with --(A) LENGTH: 20 nucleotides--.
In Column 57, in the Sequence Listing, under "(2) INFORMATION FOR SEQ ID NO:12:", under
  "(i) SEQUENCE CHARACTERISTICS:", please delete "(A) LENGTH: 19 amino acids" and
  replace with --(A) LENGTH: 20 nucleotides--.
In Column 57, in the Sequence Listing, under "(2) INFORMATION FOR SEQ ID NO:13:", under
  "(i) SEQUENCE CHARACTERISTICS:", please delete "(A) LENGTH: 19 amino acids" and
  replace with --(A) LENGTH: 20 nucleotides--.

UNITED STATES PATENT AND TRADEMARK OFFICE
CERTIFICATE OF CORRECTION

PATENT NO.    : 5,976,795

DATED         : November 2, 1999

INVENTOR(S)   : Voytas and Zou

It is certified that error appears in the above-identified patent and that said Letters Patent is hereby corrected as shown below:

In Column 57, in the Sequence Listing, under "(2) INFORMATION FOR SEQ ID NO:14:", under
"(i) SEQUENCE CHARACTERISTICS:", please delete "(A) LENGTH: 18 amino acids" and
replace with --(A) LENGTH: 19 nucleotides--.

In Column 59, in the Sequence Listing, under "(2) INFORMATION FOR SEQ ID NO:15:", under
"(i) SEQUENCE CHARACTERISTICS:", please delete "(A) LENGTH: 18 amino acids" and
replace with --(A) LENGTH: 19 nucleotides--.

In Column 59, in the Sequence Listing, under "(2) INFORMATION FOR SEQ ID NO:16:", under
"(i) SEQUENCE CHARACTERISTICS:", please delete "(A) LENGTH: 17 amino acids" and
replace with --(A) LENGTH: 18 nucleotides--.

In Column 59, in the Sequence Listing, under "(2) INFORMATION FOR SEQ ID NO:17:", under
"(i) SEQUENCE CHARACTERISTICS:", please delete "(A) LENGTH: 19 amino acids" and
replace with --(A) LENGTH: 20 nucleotides--.

In Column 59, in the Sequence Listing, under "(2) INFORMATION FOR SEQ ID NO:18:", under
"(i) SEQUENCE CHARACTERISTICS:", please delete "(A) LENGTH: 19 amino acids" and
replace with --(A) LENGTH: 20 nucleotides--.

In Column 61, in the Sequence Listing, under "(2) INFORMATION FOR SEQ ID NO:19:", under
"(i) SEQUENCE CHARACTERISTICS:", please delete "(A) LENGTH: 19 amino acids" and
replace with --(A) LENGTH: 20 nucleotides--.

In Column 61, in the Sequence Listing, under "(2) INFORMATION FOR SEQ ID NO:20:", under
"(i) SEQUENCE CHARACTERISTICS:", please delete "(A) LENGTH: 27 amino acids" and
replace with --(A) LENGTH: 28 nucleotides--.

In Column 61, in the Sequence Listing, under "(2) INFORMATION FOR SEQ ID NO:21:", under
"(i) SEQUENCE CHARACTERISTICS:", please delete "(A) LENGTH: 27 amino acids" and
replace with --(A) LENGTH: 28 nucleotides--.

In Column 61, in the Sequence Listing, under "(2) INFORMATION FOR SEQ ID NO:22:", under
"(i) SEQUENCE CHARACTERISTICS:", please delete "(A) LENGTH: 29 amino acids" and
replace with --(A) LENGTH: 30 nucleotides--.

UNITED STATES PATENT AND TRADEMARK OFFICE
CERTIFICATE OF CORRECTION

PATENT NO. : 5,976,795

DATED : November 2, 1999

INVENTOR(S) : Voytas and Zou

It is certified that error appears in the above-identified patent and that said Letters Patent is hereby corrected as shown below:

In Column 61, in the Sequence Listing, under "(2) INFORMATION FOR SEQ ID NO:23:", under "(i) SEQUENCE CHARACTERISTICS:", please delete "(A) LENGTH: 19 amino acids" and replace with --(A) LENGTH: 20 nucleotides--.

In Column 63, in the Sequence Listing, under "(2) INFORMATION FOR SEQ ID NO:24:", under "(i) SEQUENCE CHARACTERISTICS:", please delete "(A) LENGTH: 17 amino acids" and replace with --(A) LENGTH: 18 nucleotides--.

In Column 63, in the Sequence Listing, under "(2) INFORMATION FOR SEQ ID NO:25:", under "(i) SEQUENCE CHARACTERISTICS:", please delete "(A) LENGTH: 19 amino acids" and replace with --(A) LENGTH: 20 nucleotides--.

In Column 63, in the Sequence Listing, under "(2) INFORMATION FOR SEQ ID NO:26:", under "(i) SEQUENCE CHARACTERISTICS:", please delete "(A) LENGTH: 21 amino acids" and replace with --(A) LENGTH: 22 nucleotides--.

In Column 63, in the Sequence Listing, under "(2) INFORMATION FOR SEQ ID NO:27:", under "(i) SEQUENCE CHARACTERISTICS:", please delete "(A) LENGTH: 12 amino acids" and replace with --(A) LENGTH: 13 nucleotides--.

In Column 65, in the Sequence Listing, under "(2) INFORMATION FOR SEQ ID NO:28:", under "(i) SEQUENCE CHARACTERISTICS:", please delete "(A) LENGTH: 12 amino acids" and replace with --(A) LENGTH: 13 nucleotides--.

In Column 65, in the Sequence Listing, under "(2) INFORMATION FOR SEQ ID NO:29:", under "(i) SEQUENCE CHARACTERISTICS:", please delete "(A) LENGTH: 11 amino acids" and replace with --(A) LENGTH: 12 nucleotides--.

In Column 65, in the Sequence Listing, under "(2) INFORMATION FOR SEQ ID NO:30:", under "(i) SEQUENCE CHARACTERISTICS:", please delete "(A) LENGTH: 13 amino acids" and replace with --(A) LENGTH: 14 nucleotides--.

In Column 65, in the Sequence Listing, under "(2) INFORMATION FOR SEQ ID NO:31:", under "(i) SEQUENCE CHARACTERISTICS:", please delete "(A) LENGTH: 11 amino acids" and replace with --(A) LENGTH: 12 nucleotides--.

UNITED STATES PATENT AND TRADEMARK OFFICE
CERTIFICATE OF CORRECTION

PATENT NO. : 5,976,795

DATED : November 2, 1999

INVENTOR(S) : Voytas and Zou

It is certified that error appears in the above-identified patent and that said Letters Patent is hereby corrected as shown below:

In Column 71, in the Sequence Listing, under "(2) INFORMATION FOR SEQ ID NO:40:", under
"(ix) FEATURE:", please delete "(B) LOCATION: 1..136" and replace with --(B) LOCATION: 1..137--.
In Column 74-75, in the Sequence Listing, under "(2) INFORMATION FOR SEQ ID NO:43:", under
"(ix) FEATURE:", please delete "(B) LOCATION: 1..130" and replace with --(B) LOCATION: 1..137--.
In Column 75, in the Sequence Listing, under "(2) INFORMATION FOR SEQ ID NO:44:", under
"(ix) FEATURE:", please delete "(B) LOCATION: 1..128" and replace with --(B) LOCATION: 1..130--.
In Column 77, in the Sequence Listing, under "(2) INFORMATION FOR SEQ ID NO:45:", under
"(ix) FEATURE:", please delete "(B) LOCATION: 1..130" and replace with --(B) LOCATION: 1..138--.
In Column 79, in the Sequence Listing, under "(2) INFORMATION FOR SEQ ID NO:48:", under
"(ix) FEATURE:", please delete "(B) LOCATION: 1..90" and replace with --(B) LOCATION: 1..190--.

Signed and Sealed this

Thirty-first Day of October, 2000

Attest:

Q. TODD DICKINSON

Attesting Officer

Director of Patents and Trademarks